(12) United States Patent
Dandekar et al.

(10) Patent No.: US 7,449,617 B2
(45) Date of Patent: Nov. 11, 2008

(54) PLANTS WITH ELEVATED LEVELS OF GALLIC ACID/POLYPHENOL OXIDASE AND METHODS OF GENERATING SUCH PLANTS

(75) Inventors: Abhaya Dandekar, Davis, CA (US); Ryann M. Muir, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/482,150

(22) Filed: Jul. 5, 2006

(65) Prior Publication Data

US 2007/0136835 A1 Jun. 14, 2007

Related U.S. Application Data

(63) Continuation-in-part of application No. PCT/US2004/043738, filed on Dec. 22, 2004.

(60) Provisional application No. 60/534,424, filed on Jan. 5, 2004.

(51) Int. Cl.
  *C12N 15/09* (2006.01)
  *C12N 15/82* (2006.01)
  *A01H 5/00* (2006.01)

(52) U.S. Cl. .................. 800/278; 800/298; 800/279; 435/320.1; 435/468; 435/419

(58) Field of Classification Search ....................... None
See application file for complete search history.

(56) References Cited

U.S. PATENT DOCUMENTS

| 6,448,476 B1 * | 9/2002 | Barry ........................ 800/300 |
| 6,653,530 B1 * | 11/2003 | Shewmaker et al. ........ 800/282 |
| 2003/0145348 A1 * | 7/2003 | Freund et al. ............... 800/278 |

* cited by examiner

*Primary Examiner*—Medina A. Ibrahim
(74) *Attorney, Agent, or Firm*—Morrison & Foerster LLP

(57) ABSTRACT

Gallic acid inhibits the synthesis by *A. flavus* of aflatoxin, a toxic carcinogen that can contaminate crops such as corn, peanuts and walnuts rendering them inedible. The present invention takes advantage of this inhibition to provide various methods and compositions useful for protecting crops from contamination. Gallic acid is also an intermediate in the production of hydrolyzable tannins, which may sequester protein in the rumen, prevent ammonia formation, and allow protein to be more efficiently absorbed in the post-ruminant digestive system. A second gene, polyphenol oxidase (PPO), also from walnut, may act to help sequester protein during ensiling, also protecting and improving nutritional value. The present invention includes non-naturally occurring plants that contain elevated levels of PPO or gallic acid as well as various methods of generating such plants. The present invention further provides methods of application of gallic acid to prevent contamination. In addition, the present invention provides certain genes and proteins that are be useful in making the non-naturally occurring plants.

18 Claims, 26 Drawing Sheets
(10 of 26 Drawing Sheet(s) Filed in Color)

Figure 1
A
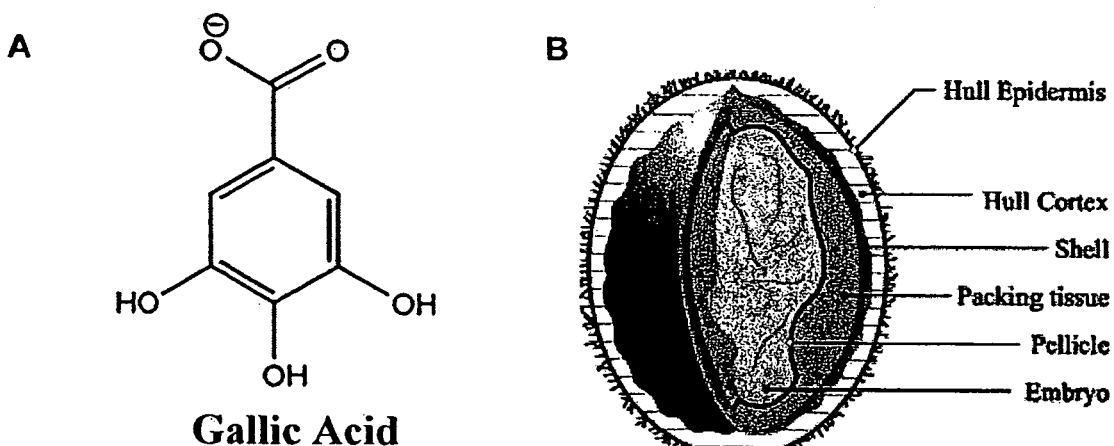
Gallic Acid
B
C
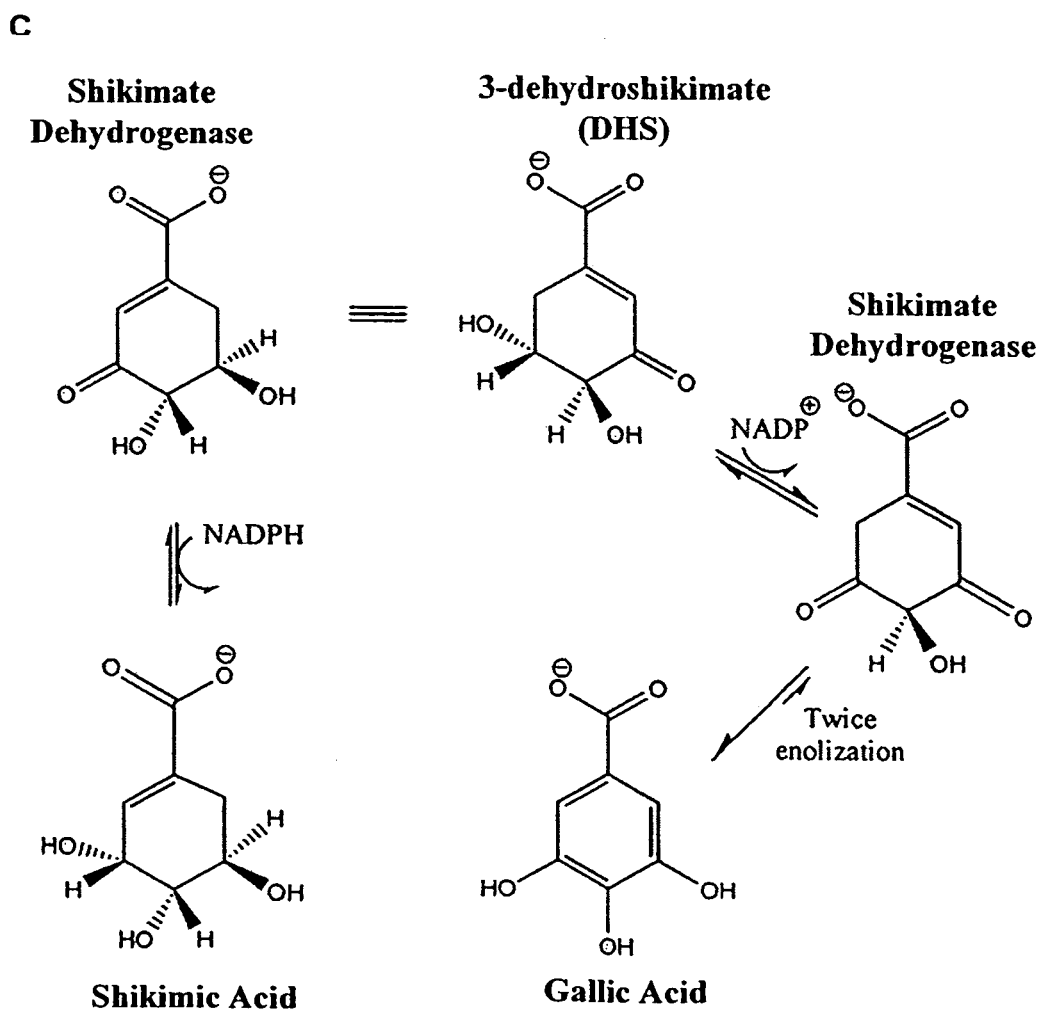

Figure 2
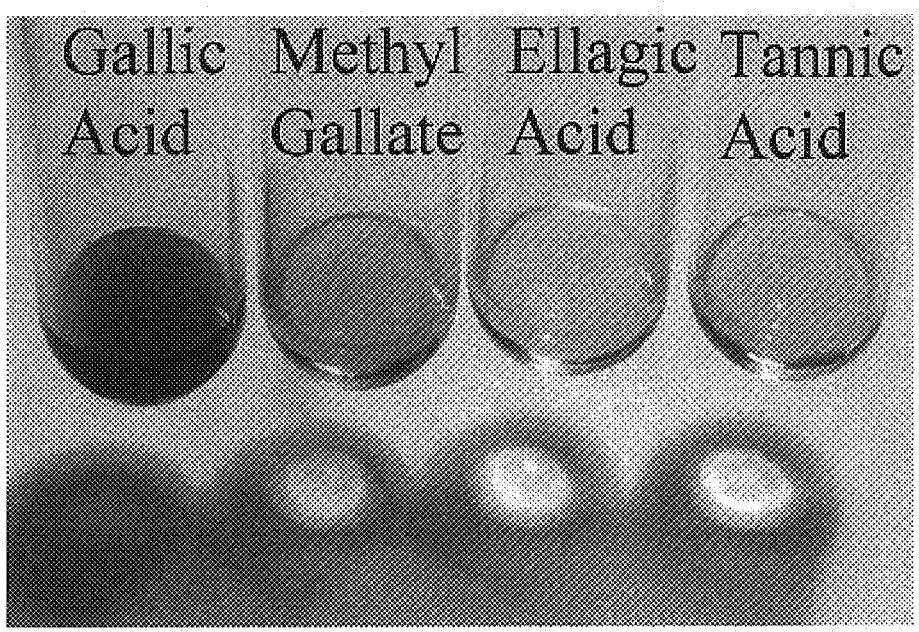
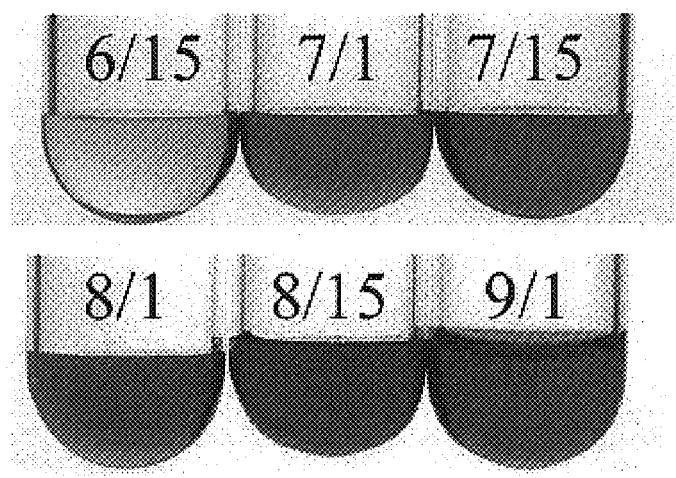

Figure 3
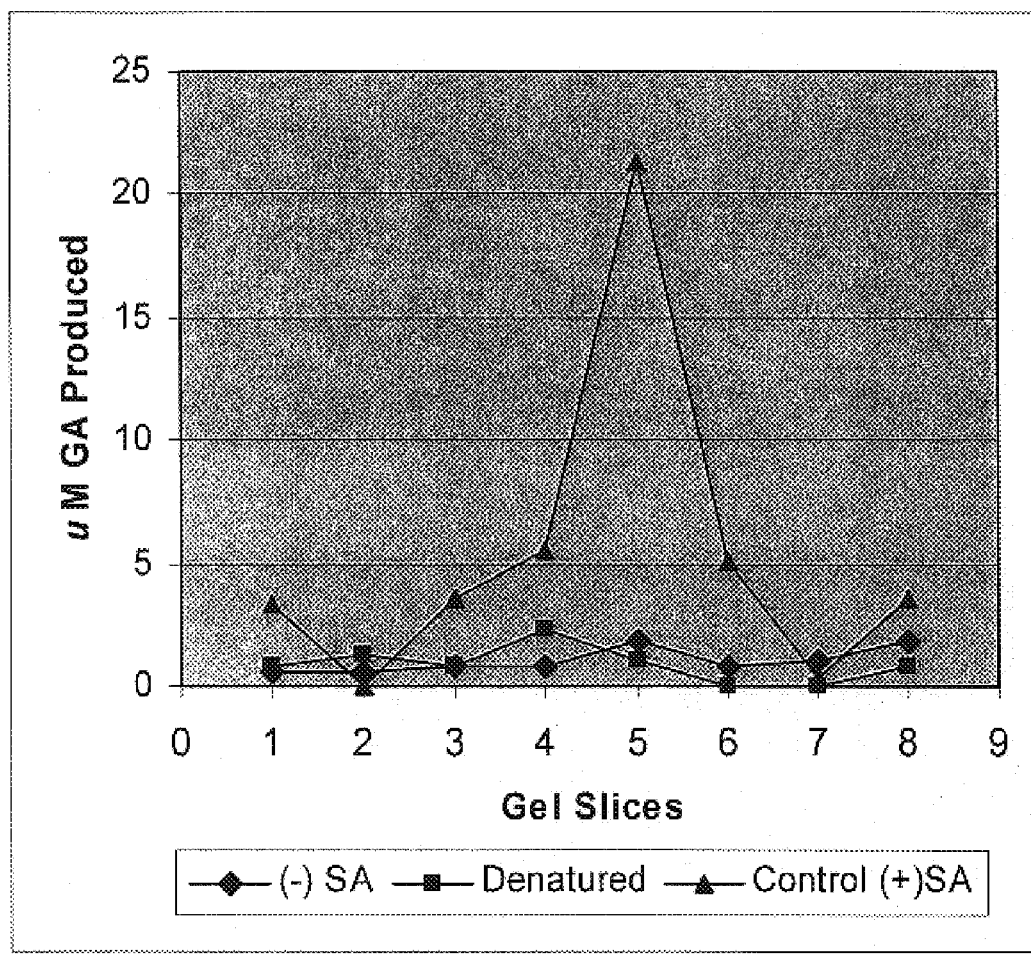
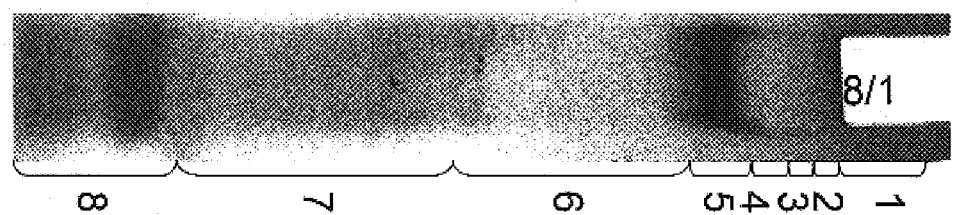

```
       G A G G A G K A L A Y G A K E K G A R V V I A N R T Y E R A R E L A D A V G G X   Majority
                    490               500              510              520
367   G A G G A G K A L A Y G A K E A G A R V V I A N R T Y D R A R E L A D T I G G D   J. regia cv Tulare
402   G A G G A G K A I A Y G A K E K G A R V V I A N R T Y E R A R E A I V V G A E   L. esculentum
383   G A G G A G K A L A Y G A K E K G A R V V I A N R T Y E R A R E L A D V V G G Q   N. tabacum
365   G A G G A G K A I A Y G A K E K G A R I V V A N R T Y E K A V S L A A V G G H   O. sativa
460   G A G G A G K A L A Y G A K E K G A K V V I A N R T Y E R A L E L A E A I G G K   A. thaliana
325                                                                                    P. sativum A L S L A E L S N F H P E D G M I L A N T T S I G M Q P K V D D T P I S K E A L   Majority
                    530               540              550              560
407   A L S L A D L D N F R E D G M L A N S T S I G M Q P K V D E T P P K H A L   J. regia cv Tulare
442   A L S L D E L S N F R E N D M L A N T T S I G M Q P K V D D T P S K E A L   L. esculentum
423   A L R L D E L S N F R E N D M L A N T T S I G M Q P K V D D T P F K E A L   N. tabacum
405   A L R L A E L E T R P E E C M L A N A T B L C M Y P N V D G T P P Q A L   O. sativa
500   A L B L T D L D N Y R E D G M V L A N T T M G M G P N V E E T P S K D A L   A. thaliana
325                                                                              P. sativum K H Y S L V F D A V Y T P K I T R L L R E A E E S G A K I V T G V E M F I G Q A   Majority
                    570               580              590              600
447   R S Y S L V F D A V Y T P K M T R L L R E A E E S G A K V T G L E M F I G Q A   J. regia cv Tulare
482   K H Y S L V F D A V Y T P K I T R L L R E A Q E S G A K V T G V E M F I G Q A   L. esculentum
463   R Y Y S L V F D A V Y T P K I T R L L R E A H G V K V T G V E M F I G Q A   N. tabacum
445   S F Y D V V F D A V Y A P K V T R L L R E A E E C G V K I V S G V E M F L R Q A   O. sativa
540   K H Y A L V F D A V Y T P R I T R L L R E A E S G A I T V S G S E M F V R Q A   A. thaliana
325                                                                                    P. sativum Y E Q F E R F T G L P A P K E L F - - - - - - - - - - - - - - - - - I M S T   Majority
                    610               620              630              640
487   Y E Q F E R F T G L P A P K E L F R K - - - - - - - - - - - - - - V M A N   J. regia cv Tulare
522   Y E Q Y E R F T G L P A P K E L F K N - - - - - - - - - - - - - - I M S T   L. esculentum
503   Y E Q Y E R F T G L A S S K G T F Q E N Y G W I L R A R S L S L F N A A L L V   N. tabacum
485   L G Q F E R F T N G I E G F D S                                               O. sativa
580   Y E Q F E R F I G L P A P K E L Y W Q - - - - - - - - - - - - - - I M S K   A. thaliana
325                                                                                P. sativum Y - - - - - - - - - - - - - - - - - - - - - -    (SEQ ID NO: 8) Majority
                    650               660
510   N                                                  (SEQ ID NO: 2) J. regia cv Tulare
545   Y                                                  (SEQ ID NO: 3) L. esculentum
543   F P P K S L H S C V I A M V L D S S A L P F V L R R N   (SEQ ID NO: 4) N. tabacum
500                                                      (SEQ ID NO: 5) O. sativa
603   Y                                                  (SEQ ID NO: 6) A. thaliana
325                                                      (SEQ ID NO: 7) P. sativum
```

Figure 6

GGATCCAACTCTAGTCTGTGCTCCTATAATGGCGGAATCGGTGGATAAGA
TGGTGATTAATATGAACAAGGCGAAACAAGGTGATGCTGACCTTGTAGAG
ATCCGATTGGATAGTTTGAAGAGCTTCAATCCTTCTAATGATCTCAAAACT
ATTATTAAAGCGTCTCCGTTGCCCACTCTATTCACTTACAGACCAAAATGG
GAAGGTG GTCAGTATGATGGTGATGAAAAGAAGCGATTGGATGCCCTTC
GATTAGCCATGGAGTTTGGAGCTGATTACATTGATGTTGAGCTCCAGGTT
GCCTGTGAGTTTAATGATTCCATTTATGGAAGGAAGCCCGAAAATTCCAA
AGTCATTGTATCTTCACAATTATCAAGACACTCCATCTGCGGAGGACCT
TGGCAACCTTG TGGCAAGAATACAAGCAACTGGTGCTGATATAGTGAA
GATTGCAACAACGGCATTGGAGATTGCTGATGTGGCACGCATTTTCCAAAT
AACTGTGCATTCTCAAGTTCCAATTATAGGAATTGTTATGGGTGAGAGAGG
TTTTATGTCGCGGATACTATGCCCAAAATTTGGTGGGTTTCTCACGTTTGGT
ACCATTGAGTCGGGAATAGTTTCTGCCCCTGGTCAACCAACAATGAAGGAT
CTTTTACATCTATACAACCTCAGACGGATAGGGCCAGATACAAAAGTGTTT
GGCATAATTGGGAAGCCTGTTCACCACAGCAAATCACCTATTTTATACAATG
AAGCATTCAAGTCAGTTTGTTTCAATGGAGTTTATATTCCTCTCTTGGTGGAT
GACATTGCAAATTTTCTTCAAACTTACTCATCCACAGATTTTGCTGGATTTAG
TTGTACAATTCCTCACAAGGAGGCCGCTCTAAAGTGCTGTGATGAGGTCGA
TCCAGTTGCGAAGTCAATAGGAGCTGTGA ATTGCATTATAAGGAGACCCAC
CGATGGGAAGTTAGTTGGTTACAATACTGATTATGTTGGTGCAATTTCTGC
TATTGAAGATGGACTGCGAGGTTCTCATAATAGTAGCAATACTGCTGATTC
ACCCTTAGCTGGTAAGCTGTTTGTGGTCATTGGTGCTGGAGGTGCTGGCAA
GGCGCTTGCTTATGGTGCAAAAGAAAAGGGAGCCAGGGTTGTGATTGCCAA
TCGCACTTATGATCGTGCCAGAGAACTTGCTGATACCATTGGTGGAGATGCT
TTATCTCTTGCCGATCTAGATAATTTCCACCCGGAGGATGGTATGATTCTTGC
AAACTCAACATCCATTGGAATGCAACCAAAAGTTGATGAAACGCCCATTCCT
AAGCATGCTCTGAGATCATACTCATTAGTTTTGATGCTGTTTACACCCCCAA
AATGACTAGACTTTTGAGGGAAGCAGAAGAATCTGGAGCCAAAATTGTTACA
GGGTTGGAGATGTTCATAGGACAGGCATATGAGCAGTTTGAGAGGTTCACTG
GGTTGCCTGCACCAAAGGAGCTATTTAGAAAAGTTATGGCCAATAACTAGA
AGCTT

SEQ ID NO: 1

Figure 7

DPTLVCAPIMAESVDKMVINMNKAKQGDADLVEIRLDSLKSFNPSNDLK
TIIKASPLPTLFTYRPKWEGGQYDGDEKKRLDALRLAMEFGADYIDVEL
QVACEFNDSIYGRKPENSKVIVSSHNYQDTPSAEDLGNLVARIQATGAD
IVKIATTALEIADVARIFQITVHSQVPIIGIVMGERGFMSRILCPKFGGFLTF
GTIESGIVSAPGQPTMKDLLHLYNLRRIGPDTKVFGIIGKPVHHSKSPILY
NEAFKSVCFNGVYIPLLVDDIANFLQTYSSTDFAGFSCTIPHKEAALKCC
DEVDPVAKSIGAVNCIIRRPTDGKLVGYNTDYVGAISAIEDGLRGSHNSS
NTADSPLAGKLFVVIGAGGAGKALAYGAKEKGARVVIANRTYDRARELA
DTIGGDALSLADLDNFHPEDGMILANSTSIGMQPKVDETPIPKHALRSYS
LVFDAVYTPKMTRLLREAEESGAKIVTGLEMFIGQAYEQFERFTGLPAPK
ELFRKVMANN*

SEQ ID NO: 2

Figure 10
A
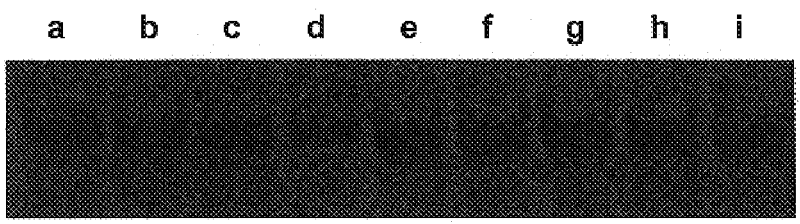
B
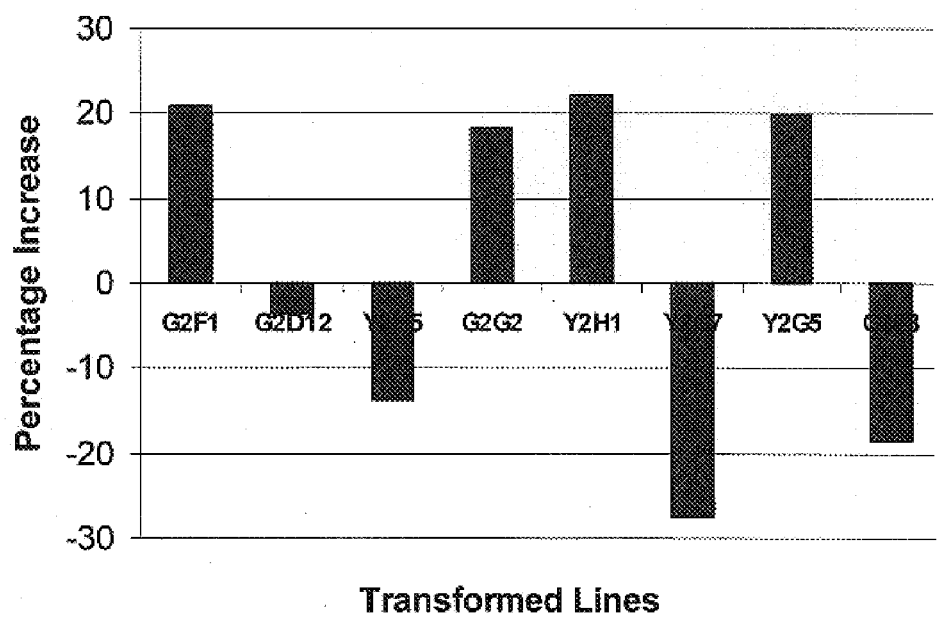

ATGGCTTCTCTCTTGGCTTCCTCCTCCCACCCTAGAAGCACCAACATGGTGGCTG
CCACCACGACCATTCGCACCCCTCTTTCCCTCCCTGTTTTCCTAGAAATACACA
AGTTTCTAAAGTTGGAAAGCAATACCACCACCTTACTACTAGAGTGGCATGCAGA
GCTACAAATGGTGACCAACAAAATATTAATAATGGACAAAATCCTCAAGGGAAG
TTCGATAGAAGAGATGTACTCCTTGGCCTCGGAGGCATGTATGGTGCTGCCAATC
TCTGCAATGACCCGTTTGCGCTGGCAGATCCGGTATCCGCGCCGGAATTAACAC
TGTGTAGCGAGGCAGACCTCCCAGCAGGCGCACTTCCAGTCAATTGCTGCCCAC
CTACATCCAAGAAGATCAAAGACTTTGTTTTACCTAGCCAAAACACTCCCTTACG
TGTTAGGCCTGCGGCTCATTTGGTTGACAACGATTACATAGCCAAATATAACAAA
GGCATTGAGCTCATGAAGTCCCTCCCGGCTGATGACCCGCGTAGTTTCACCCAA
CAAGCTAATGTCCACTGCGCCTACTGCGACGGGGCTTACACACAAGTCGGTTTTC
CAGACTTGAGCCTCCAAGTTCACGAATGTTGGCTCTTCTTTCCATTCCATCGCTAC
TACGTGTACTTCTTCGAGAAAATATTGGGCAAGTTGATTGGCGATCCCACCTTTG
CCTTGCCATTCTGGAACTGGGACTCCCCTCCTGGTATGCAATTGCCATCCTTGTA
TGCTGTCTCCAACTCAGCAATCTATGACCCTCTGCGCAACGCCAACCACCAGCC
ACCGACAATAATTGATCTTGACTACGGCGAGACCAGCGAGTCAACGACAACAAC
AGATCAAGTACCTAGCAACCTCAAAATCATGTACCGGCAGATGGTGTCCGGCGC
CAAGAACCCTACGCTATTTTCGGCAGCCTTATCGGGCTGGGGATGAACCTGA
CCCAGGTGCTGGCACAATCGAGAGCACTCCCCACAATAATATCCACCTATGGAC
CGGTGACGACACCCAACCTAATATCGAGAACATGGGGAACTTCTACTCGGCCGG
TAGAGATCCAATCTTTTTCGCTCACCATTCCAATGTGGACCGAATGTGGACCATA
TGGAAAACATTAGGAGGGAAACGAAAAGATATCACAGACCCAGATTGGTTGAAC
TCCTCATTTTTCTTCTATGATGAAAATGCAGATCCTGTTCGTGTTAAGGTTAAGGA
CTGCGTTGATAACACTAAGCTGAGATATGTTTATCAAGATGTGGAGATTCCATGG
CTAAAGACCAAGCCGACACCTCGTAAATCTAGGGTTAAGAAAGTAGCGAAAGCC
TTTCCAGCCGGACATGGTGGTGTAGCACAAGCGGCTGAAACATCGAGCGTTAAG
TTTCCGATTGTTTTGGACAAGGTGATAAGTACTGTTGTCGCTAGGCCCAAGAAAT
CGAGGAGCAAGAAAGAAAAGGACGACGAGGAAGAAGTTTTAGTGATTGAGGGT
ATTGAGGTTGAGAGAGATATTCCAGTGAAGTTTGATGTTTTATCAACGACGAGG
ATGACGCACCAACCGGGCCTGGAATTAACACGGAGTTCGCAGGAAGCTTTGTCA
GCGTGCCGCAGCAGAAGCAGACGAAGAAGAAGAAAACTTACCTGAGGATAGGA
ATCTCTGACTTGTTGGAAGACTTGGGAGCTGAAGATGATGACTCCGTGGTGGTGA
CTTTGGTACCCCGGTTCGGGAAAGGGAAGGCCATCATTGGTGGGATCAAGATTG
TGCTTATCGGTTGA

SEQ ID NO:9

Figure 24

MASLLASSSHPRSTNMVAATTTIRTPSFPPCFPRNTQVSKVGKQYHHLTTRVACRAT
NGDQQNINNGQNPQGKFDRRDVLLGLGGMYGAANLCNDPFALADPVSAPELTLCSE
ADLPAGALPVNCCPPTSKKIKDFVLPSQNTPLRVRPAAHLVDNDYIAKYNKGIELMKS
LPADDPRSFTQQANVHCAYCDGAYTQVGFPDLSLQVHECWLFFPFHRYYVYFFEKIL
GKLIGDPTFALPFWNWDSPPGMQLPSLYAVSNSAIYDPLRNANHQPPTIIDLDYGETS
ESTTTTDQVPSNLKIMYRQMVSGAKNPTLFFGSPYRAGDEPDPGAGTIESTPHNNIHL
WTGDDTQPNIENMGNFYSAGRDPIFFAHHSNVDRMWTIWKTLGGKRKDITDPDWLN
SSFFFYDENADPVRVKVKDCVDNTKLRYVYQDVEIPWLKTKPTPRKSRVKKVAKAFP
AGHGGVAQAAETSSVKFPIVLDKVISTVVARPKKSRSKKEKDDEEEVLVIEGIEVERDI
PVKFDVFINDEDDAPTGPGINTEFAGSFVSVPQQKQTKKKKTYLRIGISDLLEDLGAE
DDDSVVVTLVPRFGKGKAIIGGIKIVLIG

SEQ ID NO:10

SEQUENCE LISTING

```
<160> NUMBER OF SEQ ID NOS: 66

<210> SEQ ID NO 1
<211> LENGTH: 1540
<212> TYPE: DNA
<213> ORGANISM: Juglans regia

<400> SEQUENCE: 1
ggatccaact ctagtctgtg ctcctataat ggcggaatcg gtggataaga tggtgattaa      60
tatgaacaag gcgaaacaag gtgatgctga ccttgtagag atccgattgg atagtttgaa     120
gagcttcaat ccttctaatg atctcaaaac tattattaaa gcgtctccgt tgcccactct     180
attcacttac agaccaaaat gggaaggtgg tcagtatgat ggtgatgaaa agaagcgatt     240
ggatgccctt cgattagcca tggagtttgg agctgattac attgatgttg agctccaggt     300
tgcctgtgag tttaatgatt ccatttatgg aaggaagccc gaaaattcca aagtcattgt     360
```

```
atcttctcac aattatcaag acactccatc tgcggaggac cttggcaacc ttgtggcaag      420
aatacaagca actggtgctg atatagtgaa gattgcaaca acggcattgg agattgctga      480
tgtggcacgc atttccaaa taactgtgca ttctcaagtt ccaattatag gaattgttat      540
gggtgagaga ggttttatgt cgcggatact atgcccaaaa tttggtgggt ttctcacgtt      600
tggtaccatt gagtcgggaa tagtttctgc ccctggtcaa ccaacaatga aggatctttt      660
acatctatac aacctcagac ggatagggcc agatacaaaa gtgtttggca taattgggaa      720
gcctgttcac cacagcaaat cacctatttt atacaatgaa gcattcaagt cagtttgttt      780
caatggagtt tatattcctc tcttggtgga tgacattgca aattttcttc aaacttactc      840
atccacagat tttgctggat ttagttgtac aattcctcac aaggaggccg ctctaaagtg      900
ctgtgatgag gtcgatccag ttgcgaagtc aataggagct gtgaattgca ttataaggag      960
acccaccgat gggaagttag ttggttacaa tactgattat gttggtgcaa tttctgctat     1020
tgaagatgga ctgcgaggtt ctcataatag tagcaatact gctgattcac ccttagctgg     1080
taagctgttt gtggtcattg gtgctggagg tgctggcaag gcgcttgctt atggtgcaaa     1140
agaaaaggga gccagggttg tgattgccaa tcgcacttat gatcgtgcca gagaacttgc     1200
tgataccatt ggtggagatg ctttatctct tgccgatcta gataatttcc acccggagga     1260
tggtatgatt cttgcaaact caacatccat tggaatgcaa ccaaaagttg atgaaacgcc     1320
cattcctaag catgctctga gatcatactc attagttttt gatgctgttt acaccccccaa     1380 aatgactaga cttttgaggg aagcagaaga atctggagcc aaaattgtta cagggttgga     1440
gatgttcata ggacaggcat atgagcagtt tgagaggttc actgggttgc ctgcaccaaa     1500
ggagctattt agaaaagtta tggccaataa ctagaagctt                           1540

<210> SEQ ID NO 2
<211> LENGTH: 510
<212> TYPE: PRT
<213> ORGANISM: Juglans regia

<400> SEQUENCE: 2

Asp Pro Thr Leu Val Cys Ala Pro Ile Met Ala Glu Ser Val Asp Lys
 1               5                  10                  15

Met Val Ile Asn Met Asn Lys Ala Lys Gln Gly Asp Ala Asp Leu Val
            20                  25                  30

Glu Ile Arg Leu Asp Ser Leu Lys Ser Phe Asn Pro Ser Asn Asp Leu
        35                  40                  45

Lys Thr Ile Ile Lys Ala Ser Pro Leu Pro Thr Leu Phe Thr Tyr Arg
    50                  55                  60

Pro Lys Trp Glu Gly Gly Gln Tyr Asp Gly Asp Glu Lys Lys Arg Leu
65                  70                  75                  80

Asp Ala Leu Arg Leu Ala Met Glu Phe Gly Ala Asp Tyr Ile Asp Val
                85                  90                  95

Glu Leu Gln Val Ala Cys Glu Phe Asn Asp Ser Ile Tyr Gly Arg Lys
            100                 105                 110

Pro Glu Asn Ser Lys Val Ile Val Ser Ser His Asn Tyr Gln Asp Thr
        115                 120                 125

Pro Ser Ala Glu Asp Leu Gly Asn Leu Val Ala Arg Ile Gln Ala Thr
    130                 135                 140

Gly Ala Asp Ile Val Lys Ile Ala Thr Thr Ala Leu Glu Ile Ala Asp
145                 150                 155                 160
```

```
Val Ala Arg Ile Phe Gln Ile Thr Val His Ser Gln Val Pro Ile Ile
                165                 170                 175
Gly Ile Val Met Gly Glu Arg Gly Phe Met Ser Arg Ile Leu Cys Pro
            180                 185                 190
Lys Phe Gly Phe Leu Thr Phe Gly Thr Ile Glu Ser Gly Ile Val
        195                 200                 205
Ser Ala Pro Gly Gln Pro Thr Met Lys Asp Leu Leu His Leu Tyr Asn
    210                 215                 220
Leu Arg Arg Ile Gly Pro Asp Thr Lys Val Phe Gly Ile Ile Gly Lys
225                 230                 235                 240
Pro Val His His Ser Lys Ser Pro Ile Leu Tyr Asn Glu Ala Phe Lys
                245                 250                 255
Ser Val Cys Phe Asn Gly Val Tyr Ile Pro Leu Leu Val Asp Asp Ile
            260                 265                 270
Ala Asn Phe Leu Gln Thr Tyr Ser Ser Thr Asp Phe Ala Gly Phe Ser
        275                 280                 285
Cys Thr Ile Pro His Lys Glu Ala Ala Leu Lys Cys Cys Asp Glu Val
    290                 295                 300
Asp Pro Val Ala Lys Ser Ile Gly Ala Val Asn Cys Ile Ile Arg Arg
305                 310                 315                 320
Pro Thr Asp Gly Lys Leu Val Gly Tyr Asn Thr Asp Tyr Val Gly Ala
                325                 330                 335
Ile Ser Ala Ile Glu Asp Gly Leu Arg Gly Ser His Asn Ser Ser Asn
            340                 345                 350
Thr Ala Asp Ser Pro Leu Ala Gly Lys Leu Phe Val Val Ile Gly Ala
        355                 360                 365
Gly Gly Ala Gly Lys Ala Leu Ala Tyr Gly Ala Lys Glu Lys Gly Ala
    370                 375                 380
Arg Val Val Ile Ala Asn Arg Thr Tyr Asp Arg Ala Arg Glu Leu Ala
385                 390                 395                 400
Asp Thr Ile Gly Gly Asp Ala Leu Ser Leu Ala Asp Leu Asp Asn Phe
                405                 410                 415
His Pro Glu Asp Gly Met Ile Leu Ala Asn Ser Thr Ser Ile Gly Met
            420                 425                 430
Gln Pro Lys Val Asp Glu Thr Pro Ile Pro Lys His Ala Leu Arg Ser
        435                 440                 445
Tyr Ser Leu Val Phe Asp Ala Val Tyr Thr Pro Lys Met Thr Arg Leu
    450                 455                 460
Leu Arg Glu Ala Glu Glu Ser Gly Ala Lys Ile Val Thr Gly Leu Glu
465                 470                 475                 480
Met Phe Ile Gly Gln Ala Tyr Glu Gln Phe Glu Arg Phe Thr Gly Leu
                485                 490                 495
Pro Ala Pro Lys Glu Leu Phe Arg Lys Val Met Ala Asn Asn
            500                 505                 510

<210> SEQ ID NO 3
<211> LENGTH: 545
<212> TYPE: PRT
<213> ORGANISM: Lycopersicon esculentum

<400> SEQUENCE: 3

Met Glu Leu Val Val Asp Ser Gly Val Lys Lys Met Glu Gly Glu Ala
1               5                   10                  15
Met Arg Lys Asn Gln Thr Leu Ile Cys Ala Pro Ile Met Ala Asp Ser
            20                  25                  30
```

-continued

```
Val Asp Gln Met Leu Ile Leu Met Gln Lys Ala Lys Ile Ser Gly Ala
     35                  40                  45
Asp Leu Val Glu Val Arg Val Asp Ser Leu Lys Ser Phe Asn Pro Arg
 50                  55                  60
Pro Asp Ile Asp Thr Leu Ile Lys Gln Cys Pro Leu Pro Thr Leu Phe
 65                  70                  75                  80
Thr Tyr Ser Tyr Val Leu Gly Val Gly Gln Gly Ile Leu Leu Ile Arg
                 85                  90                  95
Tyr Tyr Lys Gly Ile Gly Pro Thr Trp Glu Gly Gln Tyr Ala Gly
             100                 105                 110
Asp Glu Lys Ser Arg Leu Asp Ala Leu Arg Leu Ala Met Glu Leu Gly
             115                 120                 125
Ala Asp Tyr Ile Asp Val Glu Leu Lys Ala Ile Gly Glu Phe Asn Asn
 130                 135                 140
Ala Leu His Gly Asn Lys Ser Ala Lys Cys Lys Leu Ile Val Ser Ser
145                 150                 155                 160
His Asn Tyr Glu Ser Thr Pro Ser Ala Glu Asp Leu Gly Asn Leu Val
                 165                 170                 175
Ala Arg Ile Gln Ala Ser Gly Ala Asp Ile Val Lys Phe Ala Thr Thr
             180                 185                 190
Ala Gln Asp Ile Thr Asp Val Ala Arg Val Phe Gln Ile Thr Val His
             195                 200                 205
Ser Gln Val Pro Ile Ile Ala Met Val Met Gly Glu Lys Gly Leu Met
 210                 215                 220
Ser Arg Ile Leu Cys Pro Lys Phe Gly Gly Tyr Leu Thr Phe Gly Thr
225                 230                 235                 240
Leu Glu Val Gly Lys Val Ser Ala Pro Gly Gln Pro Thr Val Glu Asp
                 245                 250                 255
Leu Leu Asn Leu Tyr Asn Phe Arg Gln Leu Gly Pro Asp Thr Lys Ile
             260                 265                 270
Phe Gly Ile Ile Gly Lys Pro Val Ser His Ser Lys Ser Pro Leu Leu
             275                 280                 285
Tyr Asn Glu Ser Phe Arg Ser Val Gly Phe Asn Gly Val Phe Met His
 290                 295                 300
Leu Leu Val Asp Asp Ile Ala Asn Phe Phe Arg Thr Tyr Ser Ser Leu
305                 310                 315                 320
Asp Phe Ala Gly Phe Ser Cys Thr Ile Pro His Lys Glu Ala Ala Leu
                 325                 330                 335
Asp Cys Cys Ala Glu Ile Asp Pro Thr Ala Lys Ala Ile Gly Ala Val
             340                 345                 350
Asn Cys Ile Ile Arg Arg Pro Asp Gly Lys Leu Phe Gly Cys Asn Thr
             355                 360                 365
Asp Tyr Ile Gly Ala Ile Ser Ala Ile Glu Glu Gly Leu Gln Gly Ser
 370                 375                 380
Gln Pro Ser Ile Ser Gly Ser Pro Leu Ala Gly Lys Leu Phe Val Val
385                 390                 395                 400
Ile Gly Ala Gly Gly Ala Gly Lys Ala Ile Ala Tyr Gly Ala Lys Glu
                 405                 410                 415
Lys Gly Ala Arg Val Val Ile Ala Asn Arg Thr Tyr Glu Arg Ala Arg
             420                 425                 430
Glu Leu Ala Ile Val Val Gly Ala Glu Ala Leu Ser Leu Asp Glu Leu
             435                 440                 445
```

```
Ser Asn Phe His Pro Glu Asn Asp Met Ile Leu Ala Asn Thr Thr Ser
    450                 455                 460

Ile Gly Met Gln Pro Lys Val Asp Asp Thr Pro Ile Ser Lys Glu Ala
465                 470                 475                 480

Leu Lys His Tyr Ser Leu Val Phe Asp Ala Val Tyr Thr Pro Lys Ile
                485                 490                 495

Thr Arg Leu Leu Arg Glu Ala Gln Glu Ser Gly Ala Lys Ile Val Thr
            500                 505                 510

Gly Val Glu Met Phe Ile Gly Gln Ala Tyr Glu Gln Tyr Glu Arg Phe
        515                 520                 525

Thr Gly Leu Pro Ala Pro Lys Glu Leu Phe Lys Asn Ile Met Ser Thr
    530                 535                 540

Tyr
545

<210> SEQ ID NO 4
<211> LENGTH: 569
<212> TYPE: PRT
<213> ORGANISM: Nicotiana tabacum

<400> SEQUENCE: 4

Met Glu Leu Val Val Asp Ser Gly Val Arg Lys Met Glu Gly Glu Ala
1               5                   10                  15

Met Thr Arg Asn Glu Thr Leu Ile Cys Ala Pro Ile Met Ala Asp Thr
            20                  25                  30

Val Asp Gln Met Leu Asn Leu Met Gln Lys Ala Lys Ile Ser Gly Ala
        35                  40                  45

Asp Leu Val Glu Val Arg Leu Asp Ser Leu Lys Ser Phe Asn Pro Gln
    50                  55                  60

Ser Asp Ile Asp Thr Ile Ile Lys Gln Ser Pro Leu Pro Thr Leu Phe
65                  70                  75                  80

Thr Tyr Arg Pro Thr Trp Glu Gly Gly Gln Tyr Ala Gly Asp Glu Val
                85                  90                  95

Ser Arg Leu Asp Ala Leu Arg Val Ala Met Glu Leu Gly Ala Asp Tyr
            100                 105                 110

Ile Asp Val Glu Leu Lys Ala Ile Asp Glu Phe Asn Thr Ala Leu His
        115                 120                 125

Gly Asn Lys Ser Ala Lys Cys Lys Val Ile Val Ser Ser His Asn Tyr
    130                 135                 140

Asp Asn Thr Pro Ser Ser Glu Glu Leu Gly Asn Leu Val Ala Arg Ile
145                 150                 155                 160

Gln Ala Ser Gly Ala Asp Ile Val Lys Phe Ala Thr Thr Ala Leu Asp
                165                 170                 175

Ile Met Asp Val Ala Arg Val Phe Gln Ile Thr Val His Ser Gln Val
            180                 185                 190

Pro Ile Ile Ala Met Val Met Gly Glu Lys Gly Leu Met Ser Arg Ile
        195                 200                 205

Leu Cys Pro Lys Phe Gly Gly Tyr Leu Thr Phe Gly Thr Leu Glu Val
    210                 215                 220

Gly Lys Val Ser Ala Pro Gly Gln Pro Thr Ile Lys Asp Leu Leu Asn
225                 230                 235                 240

Ile Tyr Asn Phe Arg Gln Leu Gly Pro Asp Thr Arg Ile Phe Gly Ile
                245                 250                 255

Ile Gly Lys Pro Val Ser His Ser Lys Ser Pro Leu Leu Tyr Asn Glu
            260                 265                 270
```

```
Ala Phe Arg Ser Val Gly Phe Asn Gly Val Tyr Met Pro Leu Leu Val
            275                 280                 285

Asp Asp Val Ala Asn Phe Phe Arg Thr Tyr Ser Ser Leu Asp Phe Ala
290                 295                 300

Gly Ser Ala Val Thr Ile Pro His Lys Glu Ala Ile Val Asp Cys Cys
305                 310                 315                 320

Asp Glu Leu Asn Pro Thr Ala Lys Val Ile Gly Ala Val Asn Cys Val
            325                 330                 335

Val Ser Arg Leu Asp Gly Lys Leu Phe Gly Cys Asn Thr Asp Tyr Val
            340                 345                 350

Gly Ala Ile Ser Ala Ile Glu Glu Ala Leu Gln Gly Ser Gln Pro Ser
            355                 360                 365

Met Ser Gly Ser Pro Leu Ala Gly Lys Leu Phe Val Ile Gly Ala
            370                 375                 380

Gly Gly Ala Gly Lys Ala Leu Ala Tyr Gly Ala Lys Glu Lys Gly Ala
385                 390                 395                 400

Arg Val Val Ile Ala Asn Arg Thr Tyr Glu Arg Ala Arg Glu Leu Ala
            405                 410                 415

Asp Val Val Gly Gly Gln Ala Leu Ser Leu Asp Glu Leu Ser Asn Phe
            420                 425                 430

His Pro Glu Asn Asp Met Ile Leu Ala Asn Thr Thr Ser Ile Gly Met
            435                 440                 445

Gln Pro Lys Val Asp Asp Thr Pro Ile Phe Lys Glu Ala Leu Arg Tyr
            450                 455                 460

Tyr Ser Leu Val Phe Asp Ala Val Tyr Thr Pro Lys Ile Thr Arg Leu
465                 470                 475                 480

Leu Arg Glu Ala His Glu Ser Gly Val Lys Ile Val Thr Gly Val Glu
            485                 490                 495

Met Phe Ile Gly Gln Ala Tyr Glu Gln Tyr Glu Arg Phe Thr Gly Leu
            500                 505                 510

Ala Ser Ser Lys Gly Thr Phe Gln Glu Asn Tyr Gly Trp Ile Leu Arg
            515                 520                 525

Ala Arg Ser Leu Ser Leu Phe Asn Ala Ala Leu Leu Val Thr Phe Pro
            530                 535                 540

Pro Lys Ser Leu His Ser Cys Val Ile Ala Met Val Leu Asp Ser Ser
545                 550                 555                 560

Ala Leu Pro Phe Val Leu Arg Arg Asn
            565

<210> SEQ ID NO 5
<211> LENGTH: 500
<212> TYPE: PRT
<213> ORGANISM: Oryza sativa

<400> SEQUENCE: 5

Met Thr Leu Leu Cys Val Pro Leu Val Ala Arg Thr Val Glu Ala Met
1               5                   10                  15

Arg Ala Asp Ala Ala Ala Ala Ala Gly Ala Asp Leu Val Glu
            20                  25                  30

Ile Arg Leu Asp Phe Ile Gly Ser Lys Phe Arg Pro Arg Glu Asp Leu
            35                  40                  45

Pro Arg Leu Leu Arg Gly Cys Pro Leu Pro Ala Ile Val Thr Tyr Arg
        50                  55                  60

Pro Asn Trp Glu Gly Gly Gln Tyr Glu Gly Asp Asp Ala Thr Arg Phe
```

-continued

```
                65                  70                  75                  80
Glu Ala Leu Arg Leu Ala Met Glu Leu Gly Val Asn Tyr Val Asp Ile
                    85                  90                  95
Glu Leu Lys Val Ala Asp Lys Phe Ile Ser Phe Ile Tyr Gly Ser Lys
                    100                 105                 110
Pro Glu Lys Cys Lys Leu Ile Val Ser Ala His Asn Tyr Glu Ser Thr
                    115                 120                 125
Pro Ser Cys Glu Glu Leu Ala Asp Leu Val Ala Arg Ile Gln Ala Val
                    130                 135                 140
Gly Ala Asp Ile Val Lys Ile Ala Thr Thr Ala Asn Asp Ile Val Asp
145                 150                 155                 160
Val Ser Gln Met Phe Gln Val Met Val His Cys Gln Val Pro Met Ile
                    165                 170                 175
Gly Leu Val Met Gly Glu Lys Gly Leu Met Ser Arg Val Leu Ser Pro
                    180                 185                 190
Lys Phe Gly Gly Tyr Leu Thr Phe Gly Ser Leu Asp Ala Thr Lys Val
                    195                 200                 205
Ser Ala Pro Gly Gln Pro Thr Val Glu Glu Leu Ile Asp Ile Tyr Asp
                    210                 215                 220
Ile Arg Arg Ile Gly Pro Asp Thr Lys Val Leu Gly Val Ile Ala Asn
225                 230                 235                 240
Pro Val Lys Gln Ser Lys Ser Pro Val Leu His Asn Thr Cys Leu Gln
                    245                 250                 255
Ser Val Gly Tyr Asn Ala Val Tyr Leu Pro Leu Leu Ala Asp Asn Ile
                    260                 265                 270
Ala Arg Phe Leu Ser Thr Tyr Ser Ser Pro Asp Phe Ser Gly Phe Ser
                    275                 280                 285
Cys Ser Leu Pro Phe Lys Val Asp Ala Val Gln Cys Cys His Glu His
                    290                 295                 300
Asp Pro Val Ala Lys Ser Ile Gly Ala Ile Ser Thr Ile Ile Arg Arg
305                 310                 315                 320
Pro Asp Gly Lys Leu Leu Gly Tyr Asn Asn Asp Tyr Ile Gly Ala Ile
                    325                 330                 335
Cys Ala Ile Glu Asp Gly Ile Gly Pro Gly Ser Lys Asn Ala Ala
                    340                 345                 350
Val Thr Pro Leu Ala Gly Arg Leu Val Val Val Gly Ala Gly Gly
                    355                 360                 365
Ala Gly Lys Ala Ile Ala Tyr Gly Ala Lys Glu Lys Gly Ala Arg Ile
                    370                 375                 380
Val Val Ala Asn Arg Thr Tyr Glu Lys Ala Val Ser Leu Ala Ala Ala
385                 390                 395                 400
Val Gly Gly His Ala Leu Arg Leu Ala Glu Leu Glu Thr Phe Arg Pro
                    405                 410                 415
Glu Glu Gly Met Ile Leu Ala Asn Ala Thr Ser Leu Gly Met Tyr Pro
                    420                 425                 430
Asn Val Asp Gly Thr Pro Ile Pro Lys Gln Ala Leu Ser Phe Tyr Asp
                    435                 440                 445
Val Val Phe Asp Ala Val Tyr Ala Pro Lys Val Thr Arg Leu Leu Arg
                    450                 455                 460
Glu Ala Glu Glu Cys Gly Val Lys Val Val Ser Gly Val Glu Met Phe
465                 470                 475                 480
Leu Arg Gln Ala Leu Gly Gln Phe Glu Arg Phe Thr Asn Gly Ile Glu
                    485                 490                 495
```

```
Gly Phe Asp Ser
            500

<210> SEQ ID NO 6
<211> LENGTH: 603
<212> TYPE: PRT
<213> ORGANISM: Arabidopsis thaliana

<400> SEQUENCE: 6

Met Ala Ala Ser Ser Thr Asn Ala Arg Leu Thr Asn Pro Pro Arg Leu
 1               5                  10                  15

Leu Ser Lys Pro Arg Leu Ser Pro Thr Ser Val Ala Asn Leu Arg Phe
            20                  25                  30

Pro Ala Ala Asp Phe Ser Thr Arg Phe Phe Ala Asp Ser Ser Ser Pro
        35                  40                  45

Arg Leu Arg Ser Val Pro Phe Pro Val Val Phe Ser Asp Gln Arg Arg
    50                  55                  60

Arg Arg Ser Met Glu Pro Ser Asn Val Tyr Val Ala Ser Asn Ser Thr
65                  70                  75                  80

Glu Met Glu Ile Gly Ser His Asp Ile Val Lys Asn Pro Ser Leu Ile
                85                  90                  95

Cys Ala Pro Val Met Ala Asp Ser Ile Asp Lys Met Val Ile Glu Thr
            100                 105                 110

Ser Lys Ala His Glu Leu Gly Ala Asp Leu Val Glu Ile Arg Leu Asp
        115                 120                 125

Trp Leu Lys Asp Phe Asn Pro Leu Glu Asp Leu Lys Thr Ile Ile Lys
    130                 135                 140

Lys Ser Pro Leu Pro Thr Leu Phe Thr Tyr Arg Pro Lys Trp Glu Gly
145                 150                 155                 160

Gly Gln Tyr Glu Gly Asp Glu Asn Glu Arg Arg Asp Val Leu Arg Leu
                165                 170                 175

Ala Met Glu Leu Gly Ala Asp Tyr Ile Asp Val Glu Leu Gln Val Ala
            180                 185                 190

Ser Glu Phe Ile Lys Ser Ile Asp Gly Lys Lys Pro Gly Lys Phe Lys
        195                 200                 205

Val Ile Val Ser Ser His Asn Tyr Gln Asn Thr Pro Ser Val Glu Asp
    210                 215                 220

Leu Asp Gly Leu Val Ala Arg Ile Gln Gln Thr Gly Ala Asp Ile Val
225                 230                 235                 240

Lys Ile Ala Thr Thr Ala Val Asp Ile Ala Asp Val Ala Arg Met Phe
                245                 250                 255

His Ile Ser Lys Ala Gln Val Pro Thr Ile Gly Leu Val Met Gly
            260                 265                 270

Glu Arg Gly Leu Met Ser Arg Ile Leu Cys Ser Lys Phe Gly Gly Tyr
        275                 280                 285

Leu Thr Phe Gly Thr Leu Asp Ser Ser Lys Val Ser Ala Pro Gly Gln
    290                 295                 300

Pro Thr Ile Lys Asp Leu Leu Asp Leu Tyr Asn Phe Arg Arg Ile Gly
305                 310                 315                 320

Pro Asp Thr Lys Val Tyr Gly Ile Ile Gly Lys Pro Val Ser His Ser
                325                 330                 335

Lys Ser Pro Ile Val His Asn Gln Ala Phe Lys Ser Val Asp Phe Asn
            340                 345                 350

Gly Val Tyr Val His Leu Leu Val Asp Asn Leu Val Ser Phe Leu Gln
```

```
                    355                 360                 365
Ala Tyr Ser Ser Ser Asp Phe Ala Gly Phe Ser Cys Thr Ile Pro His
    370                 375                 380

Lys Glu Ala Ala Leu Gln Cys Cys Asp Glu Val Asp Pro Leu Ala Lys
385                 390                 395                 400

Ser Ile Gly Ala Val Asn Thr Ile Leu Arg Arg Lys Ser Asp Gly Lys
                405                 410                 415

Leu Leu Gly Tyr Asn Thr Asp Cys Ile Gly Ser Ile Ser Ala Ile Glu
            420                 425                 430

Asp Gly Leu Arg Ser Ser Gly Asp Pro Ser Ser Val Pro Ser Ser Ser
        435                 440                 445

Ser Pro Leu Ala Ser Lys Thr Val Val Ile Gly Ala Gly Gly Ala
    450                 455                 460

Gly Lys Ala Leu Ala Tyr Gly Ala Lys Glu Lys Gly Ala Lys Val Val
465                 470                 475                 480

Ile Ala Asn Arg Thr Tyr Glu Arg Ala Leu Glu Leu Ala Glu Ala Ile
                485                 490                 495

Gly Gly Lys Ala Leu Ser Leu Thr Asp Leu Asp Asn Tyr His Pro Glu
            500                 505                 510

Asp Gly Met Val Leu Ala Asn Thr Thr Ser Met Gly Met Gln Pro Asn
        515                 520                 525

Val Glu Glu Thr Pro Ile Ser Lys Asp Ala Leu Lys His Tyr Ala Leu
    530                 535                 540

Val Phe Asp Ala Val Tyr Thr Pro Arg Ile Thr Arg Leu Leu Arg Glu
545                 550                 555                 560

Ala Glu Glu Ser Gly Ala Ile Thr Val Ser Gly Ser Glu Met Phe Val
                565                 570                 575

Arg Gln Ala Tyr Glu Gln Phe Glu Ile Phe Thr Gly Leu Pro Ala Pro
            580                 585                 590

Lys Glu Leu Tyr Trp Gln Ile Met Ser Lys Tyr
        595                 600

<210> SEQ ID NO 7
<211> LENGTH: 325
<212> TYPE: PRT
<213> ORGANISM: Pisum sativum
<220> FEATURE:
<221> NAME/KEY: VARIANT
<222> LOCATION: 319, 323
<223> OTHER INFORMATION: Xaa = Any Amino Acid

<400> SEQUENCE: 7

Met Lys Asn Ala Thr Leu Ile Cys Val Pro Ile Met Gly Glu Thr Val
1               5                   10                  15

Glu Lys Met Val Val Asp Ile Gln Lys Ala Lys Leu Asn Gly Ala Asp
                20                  25                  30

Leu Val Glu Ile Arg Leu Asp Ser Leu Ser Thr Phe Asn Pro His Gln
            35                  40                  45

Asp Leu Asn Thr Phe Ile Gln Gln His His Ser Leu Pro Phe Leu Phe
        50                  55                  60

Thr Tyr Arg Pro Ile Trp Glu Gly Gly Lys Tyr Asp Gly Asp Glu Asn
65                  70                  75                  80

Arg Arg Leu Asp Ala Leu Arg Leu Ala Val Glu Leu Gly Ala Asp Tyr
                85                  90                  95

Val Asp Ile Glu Leu Lys Val Ala His Glu Phe Tyr Asp Ser Ile Arg
            100                 105                 110
```

```
Gly Lys Met Phe Asn Lys Thr Lys Val Ile Val Ser Ser His Asn Tyr
            115                 120                 125

Gln Tyr Thr Pro Ser Val Glu Asp Leu Gly Asp Leu Val Ala Arg Ile
        130                 135                 140

Gln Ala Thr Gly Ala Asp Ile Val Lys Ile Ala Thr Thr Ala Val Glu
145                 150                 155                 160

Ile Thr Asp Val Ala Arg Met Phe Gln Ile Leu Val His Ser Gln Val
                165                 170                 175

Pro Phe Ile Gly Leu Val Met Gly Asp Arg Gly Leu Val Ser Arg Val
            180                 185                 190

Leu Cys Ala Lys Phe Gly Gly Tyr Leu Thr Phe Gly Thr Leu Glu Ser
        195                 200                 205

Gly Val Val Ser Ala Pro Gly Gln Pro Thr Ile Lys Asp Leu Leu His
210                 215                 220

Leu Tyr Asn Phe Arg Gln Leu Gly Pro Glu Thr Lys Val Tyr Gly Ile
225                 230                 235                 240

Ile Gly Lys Pro Val Ser His Ser Lys Ser Pro Ile Leu Phe Asn Glu
                245                 250                 255

Ala Phe Lys Thr Val Gly Phe Asn Gly Val Phe Val Phe Leu Leu Val
            260                 265                 270

Asp Asp Leu Ala Asn Phe Leu Arg Thr Tyr Ser Ser Thr Asp Phe Val
        275                 280                 285

Gly Phe Ser Val Thr Ile Pro His Lys Glu Ser Ala Leu Lys Cys Cys
        290                 295                 300

Asp Glu Val Asp Pro Val Ala Lys Ser Ile Gly Ala Val Asn Xaa Ile
305                 310                 315                 320

Val Arg Xaa Pro Thr
            325

<210> SEQ ID NO 8
<211> LENGTH: 508
<212> TYPE: PRT
<213> ORGANISM: Artificial Sequence
<220> FEATURE:
<223> OTHER INFORMATION: Majority sequence
<220> FEATURE:
<221> NAME/KEY: VARIANT
<222> LOCATION: 353, 406
<223> OTHER INFORMATION: Xaa = Any Amino Acid

<400> SEQUENCE: 8

Ser Lys Asn Pro Thr Leu Ile Cys Ala Pro Ile Met Ala Asp Ser Val
1               5                   10                  15

Asp Lys Met Val Ile Leu Met Gln Lys Ala Lys Ile Ser Gly Ala Asp
            20                  25                  30

Leu Val Glu Ile Arg Leu Asp Ser Leu Lys Ser Phe Asn Pro Arg Glu
        35                  40                  45

Asp Leu Asp Thr Ile Ile Lys Gln Ser Pro Leu Pro Thr Leu Phe Thr
    50                  55                  60

Tyr Arg Pro Thr Trp Glu Gly Gly Gln Tyr Gly Asp Glu Asn Ser
65                  70                  75                  80

Arg Leu Asp Ala Leu Arg Leu Ala Met Glu Leu Gly Ala Asp Tyr Ile
                85                  90                  95

Asp Val Glu Leu Lys Val Ala Asp Glu Phe Asn Asp Ser Ile His Gly
            100                 105                 110

Asn Lys Pro Ala Lys Cys Lys Val Ile Val Ser Ser His Asn Tyr Gln
```

```
            115                 120                 125
Ser Thr Pro Ser Ala Glu Asp Leu Gly Asn Leu Val Ala Arg Ile Gln
    130                 135                 140

Ala Thr Gly Ala Asp Ile Val Lys Ile Ala Thr Thr Ala Val Asp Ile
145                 150                 155                 160

Ala Asp Val Ala Arg Met Phe Gln Ile Thr Val His Ser Gln Val Pro
                165                 170                 175

Ile Ile Gly Leu Val Met Gly Glu Lys Gly Leu Met Ser Arg Ile Leu
            180                 185                 190

Cys Pro Lys Phe Gly Tyr Leu Thr Phe Gly Thr Leu Glu Ser Gly
        195                 200                 205

Lys Val Ser Ala Pro Gly Gln Pro Thr Ile Lys Asp Leu Leu Asp Leu
    210                 215                 220

Tyr Asn Phe Arg Gln Leu Gly Pro Asp Thr Lys Val Phe Gly Ile Ile
225                 230                 235                 240

Gly Lys Pro Val Ser His Ser Lys Ser Pro Ile Leu Tyr Asn Glu Ala
                245                 250                 255

Phe Lys Ser Val Gly Phe Asn Gly Val Tyr Val Pro Leu Leu Val Asp
            260                 265                 270

Asp Ile Ala Asn Phe Leu Arg Thr Tyr Ser Ser Leu Asp Phe Ala Gly
        275                 280                 285

Phe Ser Cys Thr Ile Pro His Lys Glu Ala Ala Leu Asp Cys Cys Asp
    290                 295                 300

Glu Val Asp Pro Val Ala Lys Ser Ile Gly Ala Val Asn Cys Ile Ile
305                 310                 315                 320

Arg Arg Pro Asp Gly Lys Leu Leu Gly Tyr Asn Thr Asp Tyr Ile Gly
                325                 330                 335

Ala Ile Ser Ala Ile Glu Asp Gly Leu Gln Gly Pro Ser Ser Pro Ser
            340                 345                 350

Xaa Ser Gly Ser Pro Leu Ala Gly Lys Leu Phe Val Val Ile Gly Ala
        355                 360                 365

Gly Gly Ala Gly Lys Ala Leu Ala Tyr Gly Ala Lys Glu Lys Gly Ala
    370                 375                 380

Arg Val Val Ile Ala Asn Arg Thr Tyr Glu Arg Ala Arg Glu Leu Ala
385                 390                 395                 400

Asp Ala Val Gly Gly Xaa Ala Leu Ser Leu Ala Glu Leu Ser Asn Phe
                405                 410                 415

His Pro Glu Asp Gly Met Ile Leu Ala Asn Thr Thr Ser Ile Gly Met
            420                 425                 430

Gln Pro Lys Val Asp Asp Thr Pro Ile Ser Lys Glu Ala Leu Lys His
        435                 440                 445

Tyr Ser Leu Val Phe Asp Ala Val Tyr Thr Pro Lys Ile Thr Arg Leu
    450                 455                 460

Leu Arg Glu Ala Glu Glu Ser Gly Ala Lys Ile Val Thr Gly Val Glu
465                 470                 475                 480

Met Phe Ile Gly Gln Ala Tyr Glu Gln Phe Glu Arg Phe Thr Gly Leu
                485                 490                 495

Pro Ala Pro Lys Glu Leu Phe Ile Met Ser Thr Tyr
            500                 505

<210> SEQ ID NO 9
<211> LENGTH: 1812
<212> TYPE: DNA
<213> ORGANISM: Juglans regia
```

<400> SEQUENCE: 9

```
atggcttctc tcttggcttc ctcctcccac cctagaagca ccaacatggt ggctgccacc      60
acgaccattc gcacccctc tttccctccc tgttttccta gaaatacaca agtttctaaa      120
gttggaaagc aataccacca ccttactact agagtggcat gcagagctac aaatggtgac      180
caacaaaata ttaataatgg acaaaatcct caagggaagt tcgatagaag agatgtactc      240
cttggcctcg gaggcatgta tggtgctgcc aatctctgca atgacccgtt tgcgctggca      300
gatccggtat ccgcgccgga attaacactg tgtagcgagg cagacctccc agcaggcgca      360
cttccagtca attgctgccc acctacatcc aagaagatca aagactttgt tttacctagc      420
caaaacactc ccttacgtgt taggcctgcg gctcatttgg ttgacaacga ttacatagcc      480
aaatataaca aaggcattga gctcatgaag tccctcccgg ctgatgaccc gcgtagtttc      540
acccaacaag ctaatgtcca ctgcgcctac tgcgacgggg cttacacaca gtcggttt      600
ccagacttga gcctccaagt tcacgaatgt tggctcttct ttccattcca tcgctactac      660
gtgtacttct tcgagaaaat attgggcaag ttgattggcg atcccacctt tgccttgcca      720
ttctggaact gggactcccc tcctggtatg caattgccat ccttgtatgc tgtctccaac      780
tcagcaatct atgaccctct gcgcaacgcc aaccaccagc caccgacaat aattgatctt      840
gactacggcg agaccagcga gtcaacgaca acaacagatc aagtacctag caacctcaaa      900
atcatgtacc ggcagatggt gtccggcgcc aagaaccta cgctattttt cggcagccct      960
tatcgggctg gggatgaacc tgacccaggt gctggcacaa tcgagagcac tccccacaat     1020
aatatccacc tatggaccgg tgacgacacc caacctaata tcgagaacat ggggaacttc     1080
tactcggccg gtagagatcc aatctttttc gctcaccatt ccaatgtgga ccgaatgtgg     1140
accatatgga aaacattagg agggaaacga aaagatatca cagacccaga ttggttgaac     1200
tcctcatttt tcttctatga tgaaaatgca gatcctgttc gtgttaaggt taaggactgc     1260
gttgataaca ctaagctgag atatgtttat caagatgtgg agattccatg gctaaagacc     1320
aagccgacac ctcgtaaatc tagggttaag aaagtagcga aagcctttcc agccggacat     1380
ggtggtgtag cacaagcggc tgaaacatcg agcgttaagt ttccgattgt tttggacaag     1440
gtgataagta ctgttgtcgc taggcccaag aaatcgagga gcaagaaaga aaaggacgac     1500
gaggaagaag ttttagtgat tgagggtatt gaggttgaga gagatattcc agtgaagttt     1560
gatgttttta tcaacgacga ggatgacgca ccaaccgggc ctggaattaa cacggagttc     1620
gcaggaagct ttgtcagcgt gccgcagcag aagcagacga agaagaagaa aacttacctg     1680
aggataggaa tctctgactt gttggaagac ttggagctg aagatgatga ctccgtggtg     1740
gtgactttgg taccccggtt cgggaaaggg aaggccatca ttggtgggat caagattgtg     1800
cttatcggtt ga                                                         1812
```

<210> SEQ ID NO 10
<211> LENGTH: 603
<212> TYPE: PRT
<213> ORGANISM: Juglans regia

<400> SEQUENCE: 10

```
Met Ala Ser Leu Leu Ala Ser Ser Ser His Pro Arg Ser Thr Asn Met
  1               5                  10                  15

Val Ala Ala Thr Thr Thr Ile Arg Thr Pro Ser Phe Pro Pro Cys Phe
             20                  25                  30
```

-continued

```
Pro Arg Asn Thr Gln Val Ser Lys Val Gly Lys Gln Tyr His His Leu
         35                  40                  45
Thr Thr Arg Val Ala Cys Arg Ala Thr Asn Gly Asp Gln Gln Asn Ile
     50                  55                  60
Asn Asn Gly Gln Asn Pro Gln Gly Lys Phe Asp Arg Arg Asp Val Leu
 65                  70                  75                  80
Leu Gly Leu Gly Gly Met Tyr Gly Ala Ala Asn Leu Cys Asn Asp Pro
                 85                  90                  95
Phe Ala Leu Ala Asp Pro Val Ser Ala Pro Glu Leu Thr Leu Cys Ser
             100                 105                 110
Glu Ala Asp Leu Pro Ala Gly Ala Leu Pro Val Asn Cys Cys Pro Pro
             115                 120                 125
Thr Ser Lys Lys Ile Lys Asp Phe Val Leu Pro Ser Gln Asn Thr Pro
         130                 135                 140
Leu Arg Val Arg Pro Ala Ala His Leu Val Asp Asn Asp Tyr Ile Ala
145                 150                 155                 160
Lys Tyr Asn Lys Gly Ile Glu Leu Met Lys Ser Leu Pro Ala Asp Asp
                165                 170                 175
Pro Arg Ser Phe Thr Gln Gln Ala Asn Val His Cys Ala Tyr Cys Asp
             180                 185                 190
Gly Ala Tyr Thr Gln Val Gly Phe Pro Asp Leu Ser Leu Gln Val His
         195                 200                 205
Glu Cys Trp Leu Phe Phe Pro Phe His Arg Tyr Tyr Val Tyr Phe Phe
         210                 215                 220
Glu Lys Ile Leu Gly Lys Leu Ile Gly Asp Pro Thr Phe Ala Leu Pro
225                 230                 235                 240
Phe Trp Asn Trp Asp Ser Pro Pro Gly Met Gln Leu Pro Ser Leu Tyr
                245                 250                 255
Ala Val Ser Asn Ser Ala Ile Tyr Asp Pro Leu Arg Asn Ala Asn His
             260                 265                 270
Gln Pro Pro Thr Ile Ile Asp Leu Asp Tyr Gly Glu Thr Ser Glu Ser
         275                 280                 285
Thr Thr Thr Thr Asp Gln Val Pro Ser Asn Leu Lys Ile Met Tyr Arg
     290                 295                 300
Gln Met Val Ser Gly Ala Lys Asn Pro Thr Leu Phe Phe Gly Ser Pro
305                 310                 315                 320
Tyr Arg Ala Gly Asp Glu Pro Asp Pro Gly Ala Gly Thr Ile Glu Ser
                325                 330                 335
Thr Pro His Asn Asn Ile His Leu Trp Thr Gly Asp Asp Thr Gln Pro
             340                 345                 350
Asn Ile Glu Asn Met Gly Asn Phe Tyr Ser Ala Gly Arg Asp Pro Ile
         355                 360                 365
Phe Phe Ala His His Ser Asn Val Asp Arg Met Trp Thr Ile Trp Lys
     370                 375                 380
Thr Leu Gly Gly Lys Arg Lys Asp Ile Thr Asp Pro Asp Trp Leu Asn
385                 390                 395                 400
Ser Ser Phe Phe Phe Tyr Asp Glu Asn Ala Asp Pro Val Arg Val Lys
                405                 410                 415
Val Lys Asp Cys Val Asp Asn Thr Lys Leu Arg Tyr Tyr Gln Asp
             420                 425                 430
Val Glu Ile Pro Trp Leu Lys Thr Lys Pro Thr Pro Arg Lys Ser Arg
         435                 440                 445
Val Lys Lys Val Ala Lys Ala Phe Pro Ala Gly His Gly Gly Val Ala
```

```
              450                 455                 460
Gln Ala Ala Glu Thr Ser Ser Val Lys Phe Pro Ile Val Leu Asp Lys
465                 470                 475                 480

Val Ile Ser Thr Val Ala Arg Pro Lys Lys Ser Arg Ser Lys Lys
                485                 490                 495

Glu Lys Asp Asp Glu Glu Val Leu Val Ile Glu Gly Ile Glu Val
                500                 505                 510

Glu Arg Asp Ile Pro Val Lys Phe Asp Val Phe Ile Asn Asp Glu Asp
                515                 520                 525

Asp Ala Pro Thr Gly Pro Gly Ile Asn Thr Glu Phe Ala Gly Ser Phe
530                 535                 540

Val Ser Val Pro Gln Gln Lys Gln Thr Lys Lys Lys Thr Tyr Leu
545                 550                 555                 560

Arg Ile Gly Ile Ser Asp Leu Leu Glu Asp Leu Gly Ala Glu Asp Asp
                565                 570                 575

Asp Ser Val Val Val Thr Leu Val Pro Arg Phe Gly Lys Gly Lys Ala
                580                 585                 590

Ile Ile Gly Gly Ile Lys Ile Val Leu Ile Gly
                595                 600
```

<210> SEQ ID NO 11
<211> LENGTH: 228
<212> TYPE: PRT
<213> ORGANISM: Escherichia coli

<400> SEQUENCE: 11

```
Ile Ile Val Ser Leu Met Ala Lys Asp Ile Ala Ser Val Lys Ser Glu
1               5                   10                  15

Ala Leu Ala Tyr Arg Glu Ala Asp Phe Asp Ile Leu Glu Trp Arg Val
                20                  25                  30

Asp His Tyr Ala Asp Leu Ser Asn Val Glu Ser Val Met Ala Ala Ala
                35                  40                  45

Lys Ile Leu Arg Glu Thr Met Pro Glu Lys Pro Leu Leu Phe Thr Phe
50                  55                  60

Arg Ser Ala Lys Glu Gly Gly Glu Gln Ala Ile Ser Thr Glu Ala Tyr
65                  70                  75                  80

Ile Ala Leu Asn Arg Ala Ala Ile Asp Ser Gly Leu Val Asp Met Ile
                85                  90                  95

Asp Leu Glu Leu Phe Thr Gly Asp Asp Gln Val Lys Glu Thr Val Ala
                100                 105                 110

Tyr Ala His Ala His Asp Val Lys Val Val Met Ser Asn His Asp Phe
                115                 120                 125

His Lys Thr Pro Glu Ala Glu Glu Ile Ile Ala Arg Leu Arg Lys Met
                130                 135                 140

Gln Ser Phe Asp Ala Asp Ile Pro Lys Ile Ala Leu Met Pro Gln Ser
145                 150                 155                 160

Thr Ser Asp Val Leu Thr Leu Leu Ala Ala Thr Leu Glu Met Gln Glu
                165                 170                 175

Gln Tyr Ala Asp Arg Pro Ile Ile Thr Met Ser Met Ala Lys Thr Gly
                180                 185                 190

Val Ile Ser Arg Leu Ala Gly Glu Val Phe Gly Ser Ala Ala Thr Phe
                195                 200                 205

Gly Ala Val Lys Lys Ala Ser Ala Pro Gly Gln Ile Ser Val Asn Asp
210                 215                 220
```

```
Leu Arg Thr Val
225

<210> SEQ ID NO 12
<211> LENGTH: 235
<212> TYPE: PRT
<213> ORGANISM: Salmonella typhi

<400> SEQUENCE: 12

Ile Ile Val Ser Leu Met Gly Arg Asp Ile Asn Ser Val Lys Ala Glu
  1               5                  10                  15

Ala Leu Ala Tyr Arg Glu Ala Thr Phe Asp Ile Leu Glu Trp Arg Val
             20                  25                  30

Asp His Phe Met Asp Ile Ala Ser Thr Gln Ser Val Leu Thr Ala Ala
         35                  40                  45

Arg Val Ile Arg Asp Ala Met Pro Asp Ile Pro Leu Leu Phe Thr Phe
     50                  55                  60

Arg Ser Ala Lys Glu Gly Gly Glu Gln Thr Ile Thr Thr Gln His Tyr
 65                  70                  75                  80

Leu Thr Leu Asn Arg Ala Ala Ile Asp Ser Gly Leu Val Asp Met Ile
                 85                  90                  95

Asp Leu Glu Leu Phe Thr Gly Asp Ala Asp Val Lys Ala Thr Val Asp
            100                 105                 110

Tyr Ala His Ala His Asn Val Tyr Val Met Ser Asn His Asp Phe
        115                 120                 125

His Gln Thr Pro Ser Ala Glu Glu Met Val Leu Arg Leu Arg Lys Met
    130                 135                 140

Gln Ala Leu Gly Ala Asp Ile Pro Lys Ile Ala Val Met Pro Gln Ser
145                 150                 155                 160

Lys His Asp Val Leu Thr Leu Thr Ala Thr Leu Glu Met Gln Gln
                165                 170                 175

His Tyr Ala Asp Arg Pro Val Ile Thr Met Ser Met Ala Lys Glu Gly
            180                 185                 190

Val Ile Ser Arg Leu Ala Gly Glu Val Phe Gly Ser Ala Ala Thr Phe
        195                 200                 205

Gly Ala Val Lys Gln Ala Ser Ala Pro Gly Gln Ile Ala Val Asn Asp
    210                 215                 220

Leu Arg Ser Val Leu Met Ile Leu His Asn Ala
225                 230                 235

<210> SEQ ID NO 13
<211> LENGTH: 218
<212> TYPE: PRT
<213> ORGANISM: Nicotiana tabacum

<400> SEQUENCE: 13

Ile Cys Ala Pro Ile Met Ala Asp Thr Val Asp Gln Met Leu Asn Leu
  1               5                  10                  15

Met Gln Lys Ala Lys Ile Ser Gly Ala Asp Leu Val Glu Val Arg Leu
             20                  25                  30

Asp Ser Leu Lys Ser Phe Asn Pro Gln Ser Asp Ile Asp Thr Ile Ile
         35                  40                  45

Lys Gln Ser Pro Leu Pro Thr Leu Phe Thr Tyr Arg Pro Thr Trp Glu
     50                  55                  60

Gly Gly Gln Tyr Ala Gly Asp Glu Val Ser Arg Leu Asp Ala Leu Arg
 65                  70                  75                  80
```

-continued

Val Ala Met Glu Leu Gly Ala Asp Tyr Ile Asp Val Glu Leu Lys Ala
                85                  90                  95

Ile Asp Glu Phe Asn Thr Ala Leu His Gly Asn Lys Ser Ala Lys Cys
            100                 105                 110

Lys Val Ile Val Ser Ser His Asn Tyr Asp Asn Thr Pro Ser Ser Glu
        115                 120                 125

Glu Leu Gly Asn Leu Val Ala Arg Ile Gln Ala Ser Gly Ala Asp Ile
    130                 135                 140

Val Lys Phe Ala Thr Thr Ala Leu Asp Ile Met Asp Val Ala Arg Val
145                 150                 155                 160

Phe Gln Ile Thr Val His Ser Gln Val Pro Ile Ile Ala Met Val Met
                165                 170                 175

Gly Glu Lys Gly Leu Met Ser Arg Ile Leu Cys Pro Lys Phe Gly Gly
            180                 185                 190

Tyr Leu Thr Phe Gly Thr Leu Glu Val Gly Lys Val Ser Ala Pro Gly
        195                 200                 205

Gln Pro Thr Ile Lys Asp Leu Leu Asn Ile
    210                 215

<210> SEQ ID NO 14
<211> LENGTH: 237
<212> TYPE: PRT
<213> ORGANISM: Lycopersicon esculentum

<400> SEQUENCE: 14

Ile Cys Ala Pro Ile Met Ala Asp Ser Val Asp Gln Met Leu Ile Leu
1               5                   10                  15

Met Gln Lys Ala Lys Ile Ser Gly Ala Asp Leu Val Glu Val Arg Val
            20                  25                  30

Asp Ser Leu Lys Ser Phe Asn Pro Arg Pro Asp Ile Asp Thr Leu Ile
        35                  40                  45

Lys Gln Cys Pro Leu Pro Thr Leu Phe Thr Tyr Ser Tyr Val Leu Gly
    50                  55                  60

Val Gly Gln Gly Ile Leu Leu Ile Arg Tyr Tyr Lys Gly Ile Gly Pro
65                  70                  75                  80

Thr Trp Glu Gly Gly Gln Tyr Ala Gly Asp Glu Lys Ser Arg Leu Asp
                85                  90                  95

Ala Leu Arg Leu Ala Met Glu Leu Gly Ala Asp Tyr Ile Asp Val Glu
            100                 105                 110

Leu Lys Ala Ile Gly Glu Phe Asn Asn Ala Leu His Gly Asn Lys Ser
        115                 120                 125

Ala Lys Cys Lys Leu Ile Val Ser Ser His Asn Tyr Glu Ser Thr Pro
    130                 135                 140

Ser Ala Glu Asp Leu Gly Asn Leu Val Ala Arg Ile Gln Ala Ser Gly
145                 150                 155                 160

Ala Asp Ile Val Lys Phe Ala Thr Thr Ala Gln Asp Ile Thr Asp Val
                165                 170                 175

Ala Arg Val Phe Gln Ile Thr Val His Ser Gln Val Pro Ile Ile Ala
            180                 185                 190

Met Val Met Gly Glu Lys Gly Leu Met Ser Arg Ile Leu Cys Pro Lys
        195                 200                 205

Phe Gly Gly Tyr Leu Thr Phe Gly Thr Leu Glu Val Gly Lys Val Ser
    210                 215                 220

Ala Pro Gly Gln Pro Thr Val Glu Asp Leu Leu Asn Leu
225                 230                 235

<210> SEQ ID NO 15
<211> LENGTH: 208
<212> TYPE: PRT
<213> ORGANISM: Arabidopsis thaliana

<400> SEQUENCE: 15

```
Ile Cys Ala Pro Val Met Ala Asp Ser Ile Asp Lys Met Val Ile Glu
 1               5                  10                  15

Thr Ser Lys Ala His Glu Leu Gly Ala Asp Leu Val Glu Ile Arg Leu
            20                  25                  30

Asp Trp Leu Lys Asp Phe Asn Pro Leu Glu Asp Leu Lys Thr Ile Ile
        35                  40                  45

Tyr Arg Pro Lys Trp Glu Gly Gly Gln Tyr Glu Gly Asp Glu Asn Glu
    50                  55                  60

Arg Arg Asp Val Leu Arg Leu Ala Met Glu Leu Gly Ala Asp Tyr Ile
65                  70                  75                  80

Asp Val Glu Leu Gln Val Ala Ser Glu Phe Ile Lys Ser Ile Asp Gly
                85                  90                  95

Lys Lys Pro Gly Lys Phe Lys Val Ile Val Ser Ser His Asn Tyr Gln
           100                 105                 110

Asn Thr Pro Ser Val Glu Asp Leu Asp Gly Leu Val Ala Arg Ile Gln
       115                 120                 125

Gln Thr Gly Ala Asp Ile Val Lys Ile Ala Thr Thr Ala Val Asp Ile
   130                 135                 140

Ala Asp Val Ala Arg Met Phe His Ile Thr Ser Lys Ala Gln Val Pro
145                 150                 155                 160

Thr Ile Gly Leu Val Met Gly Glu Arg Gly Leu Met Ser Arg Ile Leu
                165                 170                 175

Cys Ser Lys Phe Gly Gly Tyr Leu Thr Phe Gly Thr Leu Asp Ser Ser
            180                 185                 190

Lys Val Ser Ala Pro Gly Gln Pro Thr Ile Lys Asp Leu Leu Asp Leu
        195                 200                 205
```

<210> SEQ ID NO 16
<211> LENGTH: 218
<212> TYPE: PRT
<213> ORGANISM: Juglans regia

<400> SEQUENCE: 16

```
Val Cys Ala Pro Ile Met Ala Glu Ser Val Asp Lys Met Val Ile Asn
 1               5                  10                  15

Met Asn Lys Ala Lys Gln Gly Asp Ala Asp Leu Val Glu Ile Arg Leu
            20                  25                  30

Asp Ser Leu Lys Ser Phe Asn Pro Ser Asn Asp Leu Lys Thr Ile Ile
        35                  40                  45

Lys Ala Ser Pro Leu Pro Thr Leu Phe Thr Tyr Arg Pro Lys Trp Glu
    50                  55                  60

Gly Gly Gln Tyr Asp Gly Asp Glu Lys Lys Arg Leu Asp Ala Leu Arg
65                  70                  75                  80

Leu Ala Met Glu Phe Gly Ala Asp Tyr Ile Asp Val Glu Leu Gln Val
                85                  90                  95

Ala Cys Glu Phe Asn Asp Ser Ile Tyr Gly Arg Lys Pro Glu Asn Ser
           100                 105                 110

Lys Val Ile Val Ser Ser His Asn Tyr Gln Asp Thr Pro Ser Ala Glu
       115                 120                 125
```

```
Asp Leu Gly Asn Leu Val Ala Arg Ile Gln Ala Thr Gly Ala Asp Ile
        130                 135                 140

Val Lys Ile Ala Thr Thr Ala Leu Glu Ile Ala Asp Val Ala Arg Ile
145                 150                 155                 160

Phe Gln Ile Thr Val His Ser Gln Val Pro Ile Ile Gly Ile Val Met
                165                 170                 175

Gly Glu Arg Gly Phe Met Ser Arg Ile Leu Cys Pro Lys Phe Gly Gly
            180                 185                 190

Phe Leu Thr Phe Gly Thr Ile Glu Ser Gly Ile Val Ser Ala Pro Gly
        195                 200                 205

Gln Pro Thr Met Lys Asp Leu Leu His Leu
    210                 215
```

<210> SEQ ID NO 17
<211> LENGTH: 212
<212> TYPE: PRT
<213> ORGANISM: Methanococcus jannaschii

<400> SEQUENCE: 17

```
Ile Cys Leu Pro Val Val Glu Asp Ser Val Glu Lys Ala Ile Lys Thr
1               5                   10                  15

Ala Glu Lys Tyr Leu Glu Ile Ala Asp Ile Val Glu Phe Arg Ile Asp
            20                  25                  30

Met Leu Lys Glu Val Ser Glu Asp Ile Glu Lys Phe Ala Lys Tyr
        35                  40                  45

Pro Cys Ile Ile Thr Val Arg Ala Asp Trp Glu Gly Gly Tyr Trp Lys
    50                  55                  60

Gly Asn Asn Glu Glu Arg Leu Asn Leu Ile Lys Lys Ala Ile Glu Cys
65                  70                  75                  80

Asn Ala Lys Phe Val Asp Ile Glu Leu Arg Glu Glu Lys Asn Lys Glu
                85                  90                  95

Leu Val Lys Phe Arg Asp Glu Ile Gly Ser Lys Thr Lys Ile Ile Ile
            100                 105                 110

Ser Tyr His Asp Phe Glu Lys Thr Pro Ser Lys Glu Lys Leu Val Glu
        115                 120                 125

Ile Val Glu Lys Ala Leu Ser Ile Gly Asp Ile Ala Lys Phe Ala Thr
    130                 135                 140

Met Ala Asn Ser Lys Glu Asp Val Leu Asn Ile Leu Glu Val Ile Asn
145                 150                 155                 160

Lys Tyr Pro Gly Lys Ile Ile Gly Ile Gly Met Gly Glu Lys Gly Lys
                165                 170                 175

Leu Thr Arg Ile Leu Gly Val Tyr Phe Gly Ser Ile Leu Thr Phe Ala
            180                 185                 190

Ser Tyr Lys Gly Lys Ser Ser Ala Pro Gly Gln Val Asp Ile Asp Thr
        195                 200                 205

Leu Lys Glu Ile
    210
```

<210> SEQ ID NO 18
<211> LENGTH: 229
<212> TYPE: PRT
<213> ORGANISM: Staphylococcus aureus

<400> SEQUENCE: 18

```
Val Val Ala Thr Ile Thr Pro Gln Leu Tyr Ile Glu Glu Thr Leu Ile
1               5                   10                  15
```

-continued

```
Gln Lys Ile Asn His Arg Ile Asp Ala Ile Asp Val Leu Glu Leu Arg
            20                  25                  30

Ile Asp Gln Phe Glu Asn Val Thr Val Asp Gln Val Ala Glu Met Ile
        35                  40                  45

Thr Lys Leu Lys Val Met Gln Asp Ser Phe Lys Leu Leu Val Thr Tyr
 50                  55                  60

Arg Thr Lys Leu Gln Gly Gly Tyr Gly Gln Phe Thr Asn Asp Ser Tyr
 65                  70                  75                  80

Leu Asn Leu Ile Ser Asp Leu Ala Asn Ile Asn Gly Ile Asp Met Ile
                85                  90                  95

Asp Ile Glu Trp Gln Ala Asp Ile Asp Ile Glu Lys His Gln Arg Ile
            100                 105                 110

Ile Thr His Leu Gln Gln Tyr Asn Lys Glu Val Ile Ile Ser His His
            115                 120                 125

Asn Phe Glu Ser Thr Pro Pro Leu Asp Glu Leu Gln Phe Ile Phe Phe
        130                 135                 140

Lys Met Gln Lys Phe Asn Pro Glu Tyr Val Lys Leu Ala Val Met Pro
145                 150                 155                 160

His Asn Lys Asn Asp Val Leu Asn Leu Leu Gln Ala Met Ser Thr Phe
                165                 170                 175

Ser Asp Thr Met Asp Cys Lys Val Val Gly Ile Ser Met Ser Lys Leu
            180                 185                 190

Gly Leu Ile Ser Arg Thr Ala Gln Gly Val Phe Gly Gly Ala Leu Thr
        195                 200                 205

Tyr Gly Cys Ile Gly Glu Pro Gln Ala Pro Gly Gln Ile Asp Val Thr
    210                 215                 220

Asp Leu Lys Ala Gln
225

<210> SEQ ID NO 19
<211> LENGTH: 221
<212> TYPE: PRT
<213> ORGANISM: Saccharomyces cerevisiae

<400> SEQUENCE: 19

Ala Phe Val Cys Leu Thr Phe Asp Asp Leu Thr Glu Gln Thr Glu Asn
 1               5                  10                  15

Leu Thr Pro Ile Cys Tyr Gly Cys Glu Ala Val Glu Val Arg Val Asp
            20                  25                  30

His Leu Ala Asn Tyr Ser Ala Asp Phe Val Ser Lys Gln Leu Ser Ile
        35                  40                  45

Leu Arg Lys Ala Thr Asp Ser Ile Pro Ile Ile Phe Thr Val Arg Thr
 50                  55                  60

Met Lys Gln Gly Gly Asn Phe Pro Asp Glu Glu Phe Lys Thr Leu Arg
 65                  70                  75                  80

Glu Leu Tyr Asp Ile Ala Leu Lys Asn Gly Val Glu Phe Leu Asp Leu
                85                  90                  95

Glu Leu Thr Leu Pro Thr Asp Ile Gln Tyr Glu Val Ile Asn Lys Arg
            100                 105                 110

Gly Asn Thr Lys Ile Ile Gly Ser His His Asp Phe Gln Gly Leu Tyr
        115                 120                 125

Ser Trp Asp Asp Ala Glu Trp Glu Asn Arg Phe Asn Gln Ala Leu Thr
    130                 135                 140

Leu Asp Val Asp Val Val Lys Phe Val Gly Thr Ala Val Asn Phe Glu
```

```
                145                 150                 155                 160
Asp Asn Leu Arg Leu Glu His Phe Arg Asp Thr His Lys Asn Lys Pro
                    165                 170                 175

Leu Ile Ala Val Asn Met Thr Ser Lys Gly Ser Ile Ser Arg Val Leu
                180                 185                 190

Asn Asn Val Leu Thr Pro Val Thr Ser Asp Leu Leu Pro Asn Ser Ala
            195                 200                 205

Ala Pro Gly Gln Leu Thr Val Ala Gln Ile Asn Lys Met
        210                 215                 220
```

<210> SEQ ID NO 20
<211> LENGTH: 204
<212> TYPE: PRT
<213> ORGANISM: Chlamydia trachomatis

<400> SEQUENCE: 20

```
Leu Cys Thr Thr Ile Ser Gly Pro Ser Phe Leu Glu Ala Lys Lys Gln
  1               5                  10                  15

Ile Leu Arg Ser Leu Lys Glu Cys His Cys Phe Glu Met Arg Val Asp
                20                  25                  30

Leu Leu Ser Val Ser Cys Leu Glu Leu Lys Lys Leu Met Glu Leu Ala
            35                  40                  45

Pro Ile Ser Ile Leu Ala Trp Lys Lys Pro Glu Ser Cys Ser Gln Ala
        50                  55                  60

Asp Trp Ile Asp Lys Met Gln Ser Leu Ala Glu Leu Asn Pro Asn Tyr
 65                  70                  75                  80

Leu Asp Leu Glu Lys Asp Phe Pro Glu Glu Asp Met Ile Arg Ile Arg
                85                  90                  95

Gln Leu His Pro Gln Ile Lys Ile Ile Arg Ser Leu His Thr Ser Glu
               100                 105                 110

His Thr Asp Ile Ile Gln Leu Tyr Ala His Met Arg Ser Ser Ala Ala
           115                 120                 125

Asp Tyr Tyr Lys Phe Ala Val Ser Ser Ser Thr Thr Asp Leu Leu
       130                 135                 140

Asp Ile Cys His Gln Lys Arg Ser Leu Pro Glu Asn Thr Thr Val Val
145                 150                 155                 160

Cys Leu Gly Gly Met Gly Arg Pro Ser Arg Ile Leu Ser Pro Ile Leu
                165                 170                 175

Gln Asn Pro Phe Thr Tyr Ala Arg Ser Thr Gly Ser Ser Pro Val Ala
            180                 185                 190

Pro Gly Gln Phe Ser Leu Lys His His Tyr Phe Tyr
        195                 200
```

<210> SEQ ID NO 21
<211> LENGTH: 235
<212> TYPE: PRT
<213> ORGANISM: Neurospora crassa

<400> SEQUENCE: 21

```
Tyr Ala Leu Ala Leu Pro Val Ser Ala Leu Leu Asp Lys Gly Val Asp
  1               5                  10                  15

Ile Gln Glu Leu Asp Val Gly Val Asp Ala Ile Glu Ile Ile Val Asp
                20                  25                  30

Asp Leu Ala Thr Ser Glu Ser Gly Pro Thr Ser Pro Leu Gly Leu Ala
            35                  40                  45

Pro His Arg Ala Ser Glu Ile Ser Arg Val Val Gly Glu Ile Arg Arg
```

```
            50                  55                  60
Asp Thr Val Ile Pro Ile Ile Leu His Val Val Phe Pro Glu Arg Ala
 65                  70                  75                  80

Leu Tyr Glu Glu Ala Leu Leu Ala Leu Tyr Met Thr Tyr Leu Asn His
                 85                  90                  95

Ala Leu Arg Leu Ala Pro Asp Tyr Leu Thr Val Asp Leu Gly Leu Asp
            100                 105                 110

Ser Gly Leu Leu Gly Gln Leu Thr Val Gln Gly Thr Lys Val
            115                 120                 125

Ile Gly Asn Lys Gln Leu Ala Glu Val Asn Ser Pro Arg Trp Gly Asp
        130                 135                 140

Pro Ser Trp Leu Gln Ala Tyr Glu Lys Ala Gln Asn Thr Gly Cys Asp
145                 150                 155                 160

Leu Val Arg Leu Thr Arg Pro Ala Ser Asn Pro Arg Asp Asn Thr Asp
                165                 170                 175

Ile Arg Gln Phe His Val Ala Val Glu Ala Val Gly Gly Pro Arg Leu
            180                 185                 190

Pro Phe Ile Ala Tyr Asn Thr Gly Arg Leu Gly Arg Thr Ser Met Cys
        195                 200                 205

Phe Asn Glu Ile Leu Thr Pro Val Thr Pro Val Pro Thr Lys Glu Asp
        210                 215                 220

Ala Ile Gly Leu Arg Asn Pro Ala His Arg Tyr
225                 230                 235

<210> SEQ ID NO 22
<211> LENGTH: 277
<212> TYPE: PRT
<213> ORGANISM: Streptococcus pneumoniae

<400> SEQUENCE: 22

Arg Leu Ala Ala Val Val Ala Asn Pro Ile Lys His Ser Ile Ser Pro
  1               5                  10                  15

Phe Ile His Asn Arg Ala Phe Glu Ala Thr Ala Thr Asn Gly Ala Tyr
             20                  25                  30

Val Ala Trp Glu Ile Glu Ala Ser Asp Leu Val Glu Thr Val Ala Asn
         35                  40                  45

Ile Arg Arg Tyr Gln Met Phe Gly Ile Asn Leu Ser Met Pro Tyr Lys
     50                  55                  60

Glu Gln Val Ile Pro Tyr Leu Asp Lys Leu Ser Asp Glu Ala Arg Leu
 65                  70                  75                  80

Ile Gly Ala Val Asn Thr Val Asn Glu Asn Gly Asn Leu Ile Gly
                 85                  90                  95

Tyr Asn Thr Asp Gly Lys Gly Phe Lys Cys Leu Pro Ser Phe Thr
             100                 105                 110

Ile Ser Gly Lys Lys Met Thr Leu Leu Gly Ala Gly Ala Ala Lys
         115                 120                 125

Ser Ile Leu Ala Gln Ala Ile Leu Asp Gly Val Ser Gln Ile Ser Val
130                 135                 140

Phe Val Arg Ser Val Ser Met Glu Lys Thr Arg Pro Tyr Leu Asp Lys
145                 150                 155                 160

Leu Gln Glu Gln Thr Gly Phe Lys Val Asp Leu Cys Ala Leu Glu Tyr
                165                 170                 175

Val Ser Glu Leu Gln Ala Arg Ile Ala Glu Ser Asp Leu Leu Val Asn
            180                 185                 190
```

```
Ala Thr Ser Val Gly Met Asp Gly Gln Ser Ser Pro Val Pro Glu Asn
        195                 200                 205

Ile Val Leu Pro Glu Thr Leu Leu Val Ala Asp Ile Ile Tyr Gln Pro
210                 215                 220

Phe Glu Thr Pro Phe Leu Lys Trp Ala Arg Ser Gln Gly Asn Pro Ala
225                 230                 235                 240

Val Asn Gly Leu Gly Met Leu Leu Tyr Gln Ala Ala Glu Ala Phe Gln
                245                 250                 255

Leu Trp Ile Gly Lys Glu Met Pro Thr Glu Glu Ile Trp Gln Ser Leu
                260                 265                 270

Thr Glu Lys Tyr Gln
        275
```

<210> SEQ ID NO 23
<211> LENGTH: 282
<212> TYPE: PRT
<213> ORGANISM: Escherichia coli

<400> SEQUENCE: 23

```
Tyr Glu Leu Ile Gly Leu Met Ala Tyr Pro Ile Arg His Ser Leu Ser
1               5                   10                  15

Pro Glu Met Gln Asn Lys Ala Leu Glu Lys Ala Gly Leu Pro Phe Thr
                20                  25                  30

Tyr Met Ala Phe Glu Val Asp Asn Asp Ser Phe Pro Gly Ala Ile Glu
            35                  40                  45

Gly Leu Lys Ala Leu Lys Met Arg Gly Thr Gly Val Ser Met Pro Asn
50                  55                  60

Lys Gln Leu Ala Cys Glu Tyr Val Asp Glu Leu Thr Pro Ala Ala Lys
65                  70                  75                  80

Leu Val Gly Ala Ile Asn Thr Ile Val Asn Asp Gly Tyr Leu Arg
                85                  90                  95

Gly Tyr Asn Thr Asp Gly Thr Gly His Ile Arg Ala Ile Lys Glu Ser
                100                 105                 110

Gly Phe Asp Ile Lys Gly Lys Thr Met Val Leu Leu Gly Ala Gly Gly
            115                 120                 125

Ala Ser Thr Ala Ile Gly Ala Gln Gly Ala Ile Glu Gly Leu Lys Glu
            130                 135                 140

Ile Lys Leu Phe Asn Arg Arg Asp Glu Phe Phe Asp Lys Ala Leu Ala
145                 150                 155                 160

Phe Ala Gln Arg Val Asn Glu Asn Thr Asp Cys Val Val Thr Val Thr
                165                 170                 175

Asp Leu Ala Asp Gln Gln Ala Phe Ala Glu Ala Leu Ala Ser Ala Asp
            180                 185                 190

Ile Leu Thr Asn Gly Thr Lys Val Gly Met Lys Pro Leu Glu Asn Glu
            195                 200                 205

Ser Leu Val Asn Asp Ile Ser Leu Leu His Pro Gly Leu Leu Val Thr
210                 215                 220

Glu Cys Val Tyr Asn Pro His Met Thr Lys Leu Leu Gln Gln Ala Gln
225                 230                 235                 240

Gln Ala Gly Cys Lys Thr Ile Asp Gly Tyr Gly Met Leu Leu Trp Gln
                245                 250                 255

Gly Ala Glu Gln Phe Thr Leu Trp Thr Gly Lys Asp Phe Pro Leu Glu
            260                 265                 270

Tyr Val Lys Gln Val Met Gly Phe Gly Ala
275                 280
```

<210> SEQ ID NO 24
<211> LENGTH: 279
<212> TYPE: PRT
<213> ORGANISM: Juglans regia

<400> SEQUENCE: 24

Thr Lys Val Phe Gly Ile Ile Gly Lys Pro Val His His Ser Lys Ser
1               5                   10                  15

Pro Ile Leu Tyr Asn Glu Ala Phe Lys Ser Val Cys Phe Asn Gly Val
            20                  25                  30

Tyr Ile Pro Leu Leu Val Asp Asp Ile Ala Asn Phe Leu Gln Thr Tyr
        35                  40                  45

Ser Ser Thr Asp Phe Ala Gly Phe Ser Cys Thr Ile Pro His Lys Glu
50                  55                  60

Ala Ala Leu Lys Cys Cys Asp Glu Val Asp Pro Val Ala Lys Ser Ile
65                  70                  75                  80

Gly Ala Val Asn Cys Ile Ile Arg Arg Pro Thr Asp Gly Lys Leu Val
                85                  90                  95

Gly Tyr Asn Thr Asp Tyr Val Gly Ala Ile Ser Ala Ile Glu Asp Gly
            100                 105                 110

Leu Arg Gly Ser His Asn Ser Ser Asn Thr Ala Asp Ser Pro Leu Ala
        115                 120                 125

Gly Lys Leu Phe Val Val Ile Gly Ala Gly Gly Ala Gly Lys Ala Leu
130                 135                 140

Ala Tyr Gly Ala Lys Glu Lys Gly Ala Arg Val Val Ile Ala Asn Arg
145                 150                 155                 160

Thr Tyr Asp Arg Ala Arg Glu Leu Ala Asp Thr Ile Gly Gly Asp Ala
                165                 170                 175

Leu Ser Leu Ala Asp Leu Asp Asn Phe His Pro Glu Asp Gly Met Ile
            180                 185                 190

Leu Ala Asn Ser Thr Ser Ile Gly Met Gln Pro Lys Val Asp Glu Thr
        195                 200                 205

Pro Ile Pro Lys His Ala Leu Arg Ser Tyr Ser Leu Val Phe Asp Ala
210                 215                 220

Val Tyr Thr Pro Lys Met Thr Arg Leu Leu Arg Glu Ala Glu Glu Ser
225                 230                 235                 240

Gly Ala Lys Ile Val Thr Gly Leu Glu Met Phe Ile Gly Gln Ala Tyr
                245                 250                 255

Glu Gln Phe Glu Arg Phe Thr Gly Leu Pro Ala Pro Lys Glu Leu Phe
            260                 265                 270

Arg Lys Val Met Ala Asn Asn
        275

<210> SEQ ID NO 25
<211> LENGTH: 276
<212> TYPE: PRT
<213> ORGANISM: Lycopersicon esculentum

<400> SEQUENCE: 25

Thr Lys Ile Phe Gly Ile Ile Gly Lys Pro Val Ser His Ser Lys Ser
1               5                   10                  15

Pro Leu Leu Tyr Asn Glu Ser Phe Arg Ser Val Gly Phe Asn Gly Val
            20                  25                  30

Phe Met His Leu Leu Val Asp Asp Ile Ala Asn Phe Phe Arg Thr Tyr
        35                  40                  45

```
Ser Ser Leu Asp Phe Ala Gly Phe Ser Cys Thr Ile Pro His Lys Glu
    50                  55                  60

Ala Ala Leu Asp Cys Cys Ala Glu Ile Asp Pro Thr Ala Lys Ala Ile
65                  70                  75                  80

Gly Ala Val Asn Cys Ile Ile Arg Arg Pro Asp Gly Lys Leu Phe Gly
                85                  90                  95

Cys Asn Thr Asp Tyr Ile Gly Ala Ile Ser Ala Ile Glu Glu Gly Leu
            100                 105                 110

Gln Gly Ser Gln Pro Ser Ile Ser Gly Ser Pro Leu Ala Gly Lys Leu
        115                 120                 125

Phe Val Val Ile Gly Ala Gly Ala Gly Lys Ala Ile Ala Tyr Gly
    130                 135                 140

Ala Lys Glu Lys Gly Ala Arg Val Val Ile Ala Asn Arg Thr Tyr Glu
145                 150                 155                 160

Arg Ala Arg Glu Leu Ala Ile Val Val Gly Ala Glu Ala Leu Ser Leu
                165                 170                 175

Asp Glu Leu Ser Asn Phe His Pro Glu Asn Asp Met Ile Leu Ala Asn
            180                 185                 190

Thr Thr Ser Ile Gly Met Gln Pro Lys Val Asp Asp Thr Pro Ile Ser
        195                 200                 205

Lys Glu Ala Leu Lys His Tyr Ser Leu Val Phe Asp Ala Val Tyr Thr
210                 215                 220

Pro Lys Ile Thr Arg Leu Leu Arg Glu Ala Gln Glu Ser Gly Ala Lys
225                 230                 235                 240

Ile Val Thr Gly Val Glu Met Phe Ile Gly Gln Ala Tyr Glu Gln Tyr
                245                 250                 255

Glu Arg Phe Thr Gly Leu Pro Ala Pro Lys Glu Leu Phe Lys Asn Ile
            260                 265                 270

Met Ser Thr Tyr
        275

<210> SEQ ID NO 26
<211> LENGTH: 281
<212> TYPE: PRT
<213> ORGANISM: Arabidopsis thaliana

<400> SEQUENCE: 26

Thr Lys Val Tyr Gly Ile Ile Gly Lys Pro Val Ser His Ser Lys Ser
1               5                   10                  15

Pro Ile Val His Asn Gln Ala Phe Lys Ser Val Asp Phe Asn Gly Val
                20                  25                  30

Tyr Val His Leu Leu Val Asp Asn Leu Val Ser Phe Leu Gln Ala Tyr
            35                  40                  45

Ser Ser Ser Asp Phe Ala Gly Phe Ser Cys Thr Ile Pro His Lys Glu
    50                  55                  60

Ala Ala Leu Gln Cys Cys Asp Glu Val Asp Pro Leu Ala Lys Ser Ile
65                  70                  75                  80

Gly Ala Val Asn Thr Ile Leu Arg Arg Lys Ser Asp Gly Lys Leu Leu
                85                  90                  95

Gly Tyr Asn Thr Asp Cys Ile Gly Ser Ile Ser Ala Ile Glu Asp Gly
            100                 105                 110

Leu Arg Ser Ser Gly Asp Pro Ser Val Pro Ser Ser Ser Pro
        115                 120                 125

Leu Ala Ser Lys Thr Val Val Val Ile Gly Ala Gly Gly Ala Gly Lys
```

-continued

```
               130                 135                 140
Ala Leu Ala Tyr Gly Ala Lys Glu Lys Gly Ala Lys Val Val Ile Ala
145                 150                 155                 160

Asn Arg Thr Tyr Glu Arg Ala Leu Glu Leu Ala Glu Ala Ile Gly Gly
                165                 170                 175

Lys Ala Leu Ser Leu Thr Asp Leu Asp Asn Tyr His Pro Glu Asp Gly
            180                 185                 190

Met Val Leu Ala Asn Thr Thr Ser Met Gly Met Gln Pro Asn Val Glu
        195                 200                 205

Glu Thr Pro Ile Ser Lys Asp Ala Leu Lys His Tyr Ala Leu Val Phe
    210                 215                 220

Asp Ala Val Tyr Thr Pro Arg Ile Thr Arg Leu Leu Arg Glu Ala Glu
225                 230                 235                 240

Glu Ser Gly Ala Ile Thr Val Ser Gly Ser Glu Met Phe Val Arg Gln
                245                 250                 255

Ala Tyr Glu Gln Phe Glu Ile Phe Thr Gly Leu Pro Ala Pro Lys Glu
            260                 265                 270

Leu Tyr Trp Gln Ile Met Ser Lys Tyr
        275                 280
```

<210> SEQ ID NO 27
<211> LENGTH: 253
<212> TYPE: PRT
<213> ORGANISM: Thermotoga maritime

<400> SEQUENCE: 27

```
Met Lys Phe Cys Ile Ile Gly Tyr Pro Val Arg His Ser Ile Ser Pro
1               5                   10                  15

Arg Leu Tyr Asn Glu Tyr Phe Lys Arg Ala Gly Met Asn His Ser Tyr
                20                  25                  30

Gly Met Glu Glu Ile Pro Pro Glu Ser Phe Asp Thr Glu Ile Arg Arg
            35                  40                  45

Ile Leu Glu Glu Tyr Asp Gly Phe Asn Ala Thr Ile Pro His Lys Glu
        50                  55                  60

Arg Val Met Arg Tyr Val Glu Pro Ser Glu Asp Ala Gln Arg Ile Lys
65                  70                  75                  80

Ala Val Asn Cys Val Phe Arg Gly Lys Gly Tyr Asn Thr Asp Trp Val
                85                  90                  95

Gly Val Val Lys Ser Leu Glu Gly Val Glu Val Lys Glu Pro Val Val
            100                 105                 110

Val Val Gly Ala Gly Gly Ala Ala Arg Ala Val Ile Tyr Ala Leu Leu
        115                 120                 125

Gln Met Gly Val Lys Asp Ile Trp Val Val Asn Arg Thr Ile Glu Arg
    130                 135                 140

Ala Lys Ala Leu Asp Phe Pro Val Lys Ile Phe Ser Leu Asp Gln Leu
145                 150                 155                 160

Asp Glu Val Val Lys Lys Ala Lys Ser Leu Phe Asn Thr Thr Ser Val
                165                 170                 175

Gly Met Lys Gly Glu Glu Leu Pro Val Ser Asp Ser Leu Lys Asn
            180                 185                 190

Leu Ser Leu Val Tyr Asp Val Ile Tyr Phe Asp Thr Pro Leu Val Val
        195                 200                 205

Lys Ala Arg Lys Leu Gly Val Lys His Ile Ile Lys Gly Asn Leu Met
    210                 215                 220
```

```
Phe Tyr Tyr Gln Ala Met Glu Asn Leu Lys Ile Trp Gly Ile Tyr Asp
225                 230                 235                 240

Glu Glu Val Phe Lys Glu Val Phe Gly Glu Val Leu Lys
                245                 250
```

<210> SEQ ID NO 28
<211> LENGTH: 268
<212> TYPE: PRT
<213> ORGANISM: Staphylococcus aureus

<400> SEQUENCE: 28

```
Met Lys Phe Ala Val Ile Gly Asn Pro Ile Ser His Ser Leu Ser Pro
1               5                   10                  15

Val Met His Arg Ala Asn Phe Asn Ser Leu Gly Leu Asp Asp Thr Tyr
                20                  25                  30

Glu Ala Leu Asn Ile Pro Ile Glu Asp Phe His Leu Ile Lys Glu Ile
            35                  40                  45

Ile Ser Lys Lys Glu Leu Asp Gly Phe Asn Ile Thr Ile Pro His Lys
50                  55                  60

Glu Arg Ile Ile Pro Tyr Leu Asp Tyr Val Asp Glu Gln Ala Ile Asn
65                  70                  75                  80

Ala Gly Ala Val Asn Thr Val Leu Ile Lys Asp Gly Lys Trp Ile Gly
                85                  90                  95

Tyr Asn Thr Asp Gly Ile Gly Tyr Val Lys Gly Leu His Ser Val Tyr
            100                 105                 110

Pro Asp Leu Glu Asn Ala Tyr Ile Leu Ile Gly Ala Gly Gly Ala
        115                 120                 125

Ser Lys Gly Ile Ala Tyr Glu Leu Ala Lys Phe Val Lys Pro Lys Leu
130                 135                 140

Thr Val Ala Asn Arg Thr Met Ala Arg Phe Glu Ser Trp Asn Leu Asn
145                 150                 155                 160

Ile Asn Gln Ile Ser Leu Ala Asp Ala Glu Lys Tyr Leu Ala Glu Phe
                165                 170                 175

Asp Ile Val Ile Asn Thr Thr Pro Ala Gly Met Ala Gly Asn Asn Glu
            180                 185                 190

Ser Ile Ile Asn Leu Lys His Leu Ser Pro Asn Thr Leu Met Ser Asp
        195                 200                 205

Ile Val Tyr Ile Pro Tyr Lys Thr Pro Ile Leu Glu Glu Ala Glu Arg
210                 215                 220

Lys Gly Asn His Ile Tyr Asn Gly Leu Asp Met Phe Val Tyr Gln Gly
225                 230                 235                 240

Ala Glu Ser Phe Lys Ile Trp Thr Asn Lys Asp Ala Asp Ile Asn Ser
                245                 250                 255

Met Lys Thr Ala Val Leu Gln Gln Leu Lys Gly Glu
            260                 265
```

<210> SEQ ID NO 29
<211> LENGTH: 264
<212> TYPE: PRT
<213> ORGANISM: Aquifex aeolicus

<400> SEQUENCE: 29

```
Thr Gln Leu Tyr Gly Val Ile Gly Phe Pro Val Lys His Ser Leu Ser
1               5                   10                  15

Pro Val Phe Gln Asn Ala Leu Ile Arg Tyr Ala Gly Leu Asn Ala Val
                20                  25                  30
```

```
Tyr Leu Ala Phe Glu Ile Asn Pro Glu Glu Leu Lys Lys Ala Phe Glu
            35                  40                  45

Gly Phe Lys Ala Leu Lys Val Lys Gly Ile Asn Val Thr Val Pro Phe
 50                  55                  60

Lys Glu Glu Ile Ile Pro Leu Leu Asp Tyr Val Glu Asp Thr Ala Lys
 65                  70                  75                  80

Glu Ile Gly Ala Val Asn Thr Val Lys Phe Glu Asn Gly Lys Ala Tyr
                 85                  90                  95

Gly Tyr Asn Thr Asp Trp Ile Gly Phe Leu Lys Ser Leu Lys Ser Leu
            100                 105                 110

Ile Pro Glu Val Lys Glu Lys Ser Ile Leu Val Leu Gly Ala Gly Gly
            115                 120                 125

Ala Ser Arg Ala Val Ile Tyr Ala Leu Val Lys Glu Gly Ala Lys Val
130                 135                 140

Phe Leu Trp Asn Arg Thr Lys Glu Lys Ala Ile Lys Leu Ala Gln Lys
145                 150                 155                 160

Phe Pro Leu Glu Val Val Asn Ser Pro Glu Glu Val Ile Asp Lys Val
                165                 170                 175

Gln Val Ile Val Asn Thr Thr Ser Val Gly Leu Lys Asp Lys Asp Pro
            180                 185                 190

Glu Ile Phe Asn Tyr Asp Leu Ile Lys Lys Asp His Val Val Val Asp
            195                 200                 205

Ile Ile Tyr Lys Glu Thr Lys Leu Leu Lys Ala Lys Glu Lys Gly
            210                 215                 220

Ala Lys Leu Phe Asp Gly Leu Pro Met Leu Leu Trp Gln Gly Ile Glu
225                 230                 235                 240

Ala Phe Lys Ile Trp Asn Gly Cys Glu Val Pro Tyr Ser Val Ala Glu
                245                 250                 255

Arg Ser Val Arg Asp Leu Arg Gly
            260

<210> SEQ ID NO 30
<211> LENGTH: 277
<212> TYPE: PRT
<213> ORGANISM: Methanococcus jannaschii

<400> SEQUENCE: 30

Thr Lys Val Ile Gly Leu Ile Gly His Pro Val Glu His Ser Phe Ser
 1               5                  10                  15

Pro Ile Met His Asn Ala Ala Phe Lys Asp Lys Gly Leu Asn Tyr Val
                 20                  25                  30

Tyr Val Ala Phe Asp Val Leu Pro Glu Asn Leu Lys Tyr Val Ile Asp
            35                  40                  45

Gly Ala Lys Ala Leu Gly Ile Val Gly Phe Asn Val Thr Ile Pro His
 50                  55                  60

Lys Ile Glu Ile Met Lys Tyr Leu Asp Glu Ile Asp Lys Asp Ala Gln
 65                  70                  75                  80

Leu Ile Gly Ala Val Asn Thr Ile Lys Ile Glu Asp Gly Lys Ala Ile
                 85                  90                  95

Gly Tyr Asn Thr Asp Gly Ile Gly Ala Arg Met Ala Leu Glu Glu Glu
            100                 105                 110

Ile Gly Arg Val Lys Asp Lys Asn Ile Val Ile Tyr Gly Ala Gly Gly
            115                 120                 125

Ala Ala Arg Ala Val Ala Phe Glu Leu Ala Lys Asp Asn Asn Ile Ile
130                 135                 140
```

Ile Ala Asn Arg Thr Val Glu Lys Ala Glu Ala Leu Ala Lys Glu Ile
145                 150                 155                 160

Ala Glu Lys Leu Asn Lys Lys Phe Gly Glu Val Lys Phe Ser Gly
            165                 170                 175

Leu Asp Val Asp Leu Asp Gly Val Asp Ile Ile Ile Asn Ala Thr Pro
            180                 185                 190

Ile Gly Met Tyr Pro Asn Ile Asp Val Glu Pro Ile Val Lys Ala Glu
            195                 200                 205

Lys Leu Arg Glu Asp Met Val Val Met Asp Leu Ile Tyr Asn Pro Leu
        210                 215                 220

Glu Thr Val Leu Leu Lys Glu Ala Lys Lys Val Asn Ala Lys Thr Ile
225                 230                 235                 240

Asn Gly Leu Gly Met Leu Ile Tyr Gln Gly Ala Val Ala Phe Lys Ile
                245                 250                 255

Trp Thr Gly Val Glu Pro Asn Ile Glu Val Met Lys Asn Ala Ile Ile
            260                 265                 270

Asp Lys Ile Thr Lys
        275

<210> SEQ ID NO 31
<211> LENGTH: 277
<212> TYPE: PRT
<213> ORGANISM: Bacillus subtilis

<400> SEQUENCE: 31

Lys Lys Leu Tyr Gly Val Ile Gly Asn Pro Ile Gly His Ser Met Ser
1               5                   10                  15

Pro Asp Ile His Asn Ala Ser Leu Lys Asp Leu Gly Leu Asp Gly His
            20                  25                  30

Tyr His Ala Phe Lys Val Glu Glu Asn Asp Leu Glu Asp Ala Val Lys
        35                  40                  45

Gly Ile Arg Ala Leu Gly Val Gln Gly Ile Asn Val Thr Val Pro His
    50                  55                  60

Lys Val Ser Ile Met Asp Tyr Leu Asp His Ile Asp Glu Ser Ala Lys
65                  70                  75                  80

Val Leu Gly Ala Val Asn Thr Val Arg Arg Glu Gly Asp Lys Leu Val
                85                  90                  95

Gly Tyr Asn Thr Asp Gly Glu Gly Phe Val Lys Ser Leu Met Lys Val
            100                 105                 110

Leu Asp Lys Pro Ile Ser Glu Leu Ser Phe Leu Met Ile Gly Ala Gly
        115                 120                 125

Gly Ala Ala Arg Ala Ile Phe Thr Thr Phe Val Arg Asn Thr Pro Lys
130                 135                 140

Lys Phe Asp Ile Cys Asn Arg Thr Leu Glu Lys Ala Lys Arg Leu Thr
145                 150                 155                 160

Glu Ala Thr Pro Ser Phe His Asn Lys Glu Val Leu Ser Ile Lys Glu
                165                 170                 175

Ala Glu Glu Arg Leu Glu Gln Tyr Asp Val Ile His Thr Thr Ser
            180                 185                 190

Val Gly Met Tyr Pro Asn Val Asp Asp Val Pro Leu Ser Leu Gln Arg
        195                 200                 205

Ala Ala Ser Ser Ala Val Val Cys Asp Ile Val Tyr Asn Pro Ile Gln
    210                 215                 220

Thr Ala Leu Leu Lys Glu Ala Ser Gln Lys Gly Leu Lys Thr Leu Asp

-continued

```
                225                 230                 235                 240
Gly Val Gly Met Phe Val Glu Gln Ala Ala Leu Ser Phe Gln Leu Trp
                    245                 250                 255

Thr Gly Gln Glu Pro Asn Ile Glu Lys Met Arg Ser Ile Val Ile Gly
                260                 265                 270

Lys Leu Gly Gly Thr
        275

<210> SEQ ID NO 32
<211> LENGTH: 272
<212> TYPE: PRT
<213> ORGANISM: Escherichia coli

<400> SEQUENCE: 32

Met Glu Thr Tyr Ala Val Phe Gly Asn Pro Ile Ala His Ser Lys Ser
  1               5                  10                  15

Pro Phe Ile His Gln Gln Phe Ala Gln Gln Leu Asn Ile Glu His Pro
             20                  25                  30

Tyr Gly Arg Val Leu Ala Pro Ile Asn Asp Phe Ile Asn Thr Leu Asn
         35                  40                  45

Ala Phe Phe Ser Ala Gly Gly Lys Gly Ala Asn Val Thr Val Pro Phe
     50                  55                  60

Lys Glu Glu Ala Phe Ala Arg Ala Asp Glu Leu Thr Glu Arg Ala Ala
 65                  70                  75                  80

Leu Ala Gly Ala Val Asn Thr Leu Met Arg Leu Glu Asp Gly Arg Leu
                 85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125

Gly Ala Ser Arg Gly Val Leu Leu Pro Leu Leu Ser Leu Asp Cys Ala
    130                 135                 140

Val Thr Ile Thr Asn Arg Thr Val Ser Arg Ala Glu Glu Leu Ala Lys
145                 150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
    210                 215                 220

Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln Leu Gln Glu Glu Leu Ser Ala
            260                 265                 270

<210> SEQ ID NO 33
<211> LENGTH: 274
<212> TYPE: PRT
<213> ORGANISM: Pseudomonas aeruginosa

<400> SEQUENCE: 33

Met Asp Arg Tyr Cys Val Phe Gly Asn Pro Ile Gly His Ser Lys Ser
```

```
                1               5                  10                 15
Pro Leu Ile His Arg Leu Phe Ala Glu Gln Thr Gly Glu Ala Leu Val
                    20                  25                  30

Tyr Asp Ala Gln Leu Ala Pro Leu Asp Asp Phe Pro Gly Phe Ala Arg
                    35                  40                  45

Arg Phe Phe Glu Gln Gly Lys Gly Ala Asn Val Thr Val Pro Phe Lys
                50                  55                  60

Glu Glu Ala Tyr Arg Leu Val Asp Glu Leu Ser Glu Arg Ala Thr Arg
 65                 70                  75                  80

Ala Gly Ala Val Asn Thr Leu Ile Arg Leu Ala Asp Gly Arg Leu Arg
                    85                  90                  95

Gly Asp Asn Thr Asp Gly Ala Gly Leu Leu Arg Asp Leu Thr Ala Asn
                100                 105                 110

Ala Gly Val Glu Leu Arg Gly Lys Arg Val Leu Leu Gly Ala Gly
                115                 120                 125

Gly Ala Val Arg Gly Val Leu Glu Pro Phe Leu Gly Glu Cys Pro Ala
                130                 135                 140

Glu Leu Leu Ile Ala Asn Arg Thr Ala Arg Lys Ala Val Asp Leu Ala
145                 150                 155                 160

Glu Arg Phe Ala Asp Leu Gly Ala Val His Gly Cys Gly Phe Ala Glu
                165                 170                 175

Val Glu Gly Pro Phe Asp Leu Ile Val Asn Gly Thr Ser Ala Ser Leu
                180                 185                 190

Ala Gly Asp Val Pro Pro Leu Ala Gln Ser Val Ile Glu Pro Gly Arg
                195                 200                 205

Thr Val Cys Tyr Asp Met Met Tyr Ala Lys Glu Pro Thr Ala Phe Asn
                210                 215                 220

Arg Trp Ala Ala Glu Arg Gly Ala Ala Arg Thr Leu Asp Gly Leu Gly
225                 230                 235                 240

Met Leu Val Glu Gln Ala Glu Ala Phe Phe Leu Trp Arg Gly Val
                245                 250                 255

Arg Pro Ala Ser Ala Pro Val Leu Glu Thr Leu Arg Arg Gln Leu Ala
                260                 265                 270

Thr Val

<210> SEQ ID NO 34
<211> LENGTH: 272
<212> TYPE: PRT
<213> ORGANISM: Haemophilus influenzae

<400> SEQUENCE: 34

Met Asp Leu Tyr Ala Val Trp Gly Asn Pro Ile Ala Gln Ser Lys Ser
 1               5                  10                  15

Pro Leu Ile Gln Asn Lys Leu Ala Ala Gln Thr His Gln Thr Met Glu
                    20                  25                  30

Tyr Ile Ala Lys Leu Gly Asp Leu Asp Ala Phe Glu Gln Gln Leu Leu
                    35                  40                  45

Ala Phe Phe Glu Glu Gly Ala Lys Gly Cys Asn Ile Thr Ser Pro Phe
                50                  55                  60

Lys Glu Arg Ala Tyr Gln Leu Ala Asp Glu Tyr Ser Gln Arg Ala Lys
 65                 70                  75                  80

Leu Ala Glu Ala Cys Asn Thr Leu Lys Lys Leu Asp Asp Gly Lys Leu
                    85                  90                  95

Tyr Ala Asp Asn Thr Asp Gly Ile Gly Leu Val Thr Asp Leu Gln Arg
```

-continued

```
                100                 105                 110
Leu Asn Trp Leu Arg Pro Asn Gln His Val Leu Ile Leu Gly Ala Gly
            115                 120                 125

Gly Ala Thr Lys Gly Val Leu Leu Pro Leu Leu Gln Ala Gln Gln Asn
    130                 135                 140

Ile Val Leu Ala Asn Arg Thr Phe Ser Lys Thr Lys Glu Leu Ala Glu
145                 150                 155                 160

Arg Phe Gln Pro Tyr Gly Asn Ile Gln Ala Val Ser Met Asp Ser Ile
                165                 170                 175

Pro Leu Gln Thr Tyr Asp Leu Val Ile Asn Ala Thr Ser Ala Gly Leu
            180                 185                 190

Ser Gly Gly Thr Ala Ser Val Asp Ala Glu Ile Leu Lys Leu Gly Ser
        195                 200                 205

Ala Phe Tyr Asp Met Gln Tyr Ala Lys Gly Thr Asp Thr Pro Phe Ile
    210                 215                 220

Ala Leu Cys Lys Ser Leu Gly Leu Thr Asn Val Ser Asp Gly Phe Gly
225                 230                 235                 240

Met Leu Val Ala Gln Ala Ala His Ser Phe His Leu Trp Arg Gly Val
                245                 250                 255

Met Pro Asp Phe Val Ser Val Tyr Glu Gln Leu Lys Lys Ala Met Leu
            260                 265                 270

<210> SEQ ID NO 35
<211> LENGTH: 274
<212> TYPE: PRT
<213> ORGANISM: Nicotiana tabacum

<400> SEQUENCE: 35

Pro Asp Thr Arg Ile Phe Gly Ile Ile Gly Lys Pro Val Ser His Ser
1               5                   10                  15

Lys Ser Pro Leu Leu Tyr Asn Glu Ala Phe Arg Ser Val Gly Phe Asn
            20                  25                  30

Gly Val Tyr Met Pro Leu Leu Val Asp Asp Val Ala Asn Phe Phe Arg
        35                  40                  45

Thr Tyr Ser Ser Leu Asp Phe Ala Gly Ser Ala Val Thr Ile Pro His
    50                  55                  60

Lys Glu Ala Ile Val Asp Cys Cys Asp Glu Leu Asn Pro Thr Ala Lys
65                  70                  75                  80

Val Ile Gly Ala Val Asn Cys Val Val Ser Arg Leu Asp Gly Lys Leu
                85                  90                  95

Phe Gly Cys Asn Thr Asp Tyr Val Gly Ala Ile Ser Ala Ile Glu Glu
            100                 105                 110

Ala Leu Gln Gly Ser Gln Pro Ser Met Ser Gly Ser Pro Leu Ala Gly
        115                 120                 125

Lys Leu Phe Val Val Ile Gly Ala Gly Ala Gly Lys Ala Leu Ala
    130                 135                 140

Tyr Gly Ala Lys Glu Lys Gly Ala Arg Val Val Ile Ala Asn Arg Thr
145                 150                 155                 160

Tyr Glu Arg Ala Arg Glu Leu Ala Asp Val Val Gly Gly Gln Ala Leu
                165                 170                 175

Ser Leu Asp Glu Leu Ser Asn Phe His Pro Glu Asn Asp Met Ile Leu
            180                 185                 190

Ala Asn Thr Thr Ser Ile Gly Met Gln Pro Lys Val Asp Asp Thr Pro
        195                 200                 205
```

-continued

Ile Phe Lys Glu Ala Leu Arg Tyr Tyr Ser Leu Val Phe Asp Ala Val
210                 215                 220

Tyr Thr Pro Lys Ile Thr Arg Leu Leu Arg Glu Ala His Glu Ser Gly
225                 230                 235                 240

Val Lys Ile Val Thr Gly Val Glu Met Phe Ile Gly Gln Ala Tyr Glu
            245                 250                 255

Gln Tyr Glu Arg Phe Thr Gly Leu Ala Ser Ser Lys Gly Thr Phe Gln
            260                 265                 270

Glu Asn

<210> SEQ ID NO 36
<211> LENGTH: 273
<212> TYPE: PRT
<213> ORGANISM: Lycopersicon esculentum

<400> SEQUENCE: 36

Pro Asp Thr Lys Ile Phe Gly Ile Ile Gly Lys Pro Val Ser His Ser
1               5                   10                  15

Lys Ser Pro Leu Leu Tyr Asn Glu Ser Phe Arg Ser Val Gly Phe Asn
            20                  25                  30

Gly Val Phe Met His Leu Leu Val Asp Asp Ile Ala Asn Phe Phe Arg
        35                  40                  45

Thr Tyr Ser Ser Leu Asp Phe Ala Gly Phe Ser Cys Thr Ile Pro His
50                  55                  60

Lys Glu Ala Ala Leu Asp Cys Cys Ala Glu Ile Asp Pro Thr Ala Lys
65                  70                  75                  80

Ala Ile Gly Ala Val Asn Cys Ile Ile Arg Arg Pro Asp Gly Lys Leu
                85                  90                  95

Phe Gly Cys Asn Thr Asp Tyr Ile Gly Ala Ile Ser Ala Ile Glu Glu
            100                 105                 110

Gly Leu Gln Gly Ser Gln Pro Ser Ile Ser Gly Ser Pro Leu Ala Gly
        115                 120                 125

Lys Leu Phe Val Val Ile Gly Ala Gly Ala Gly Lys Ala Ile Ala
130                 135                 140

Tyr Gly Ala Lys Glu Lys Gly Ala Arg Val Val Ile Ala Asn Arg Thr
145                 150                 155                 160

Tyr Glu Arg Ala Arg Glu Leu Ala Ile Val Val Gly Ala Glu Ala Leu
                165                 170                 175

Ser Leu Asp Glu Leu Ser Asn Phe His Pro Glu Asn Asp Met Ile Leu
            180                 185                 190

Ala Asn Thr Thr Ser Ile Gly Met Gln Pro Lys Val Asp Asp Thr Pro
        195                 200                 205

Ile Ser Lys Glu Ala Leu Lys His Tyr Ser Leu Val Phe Asp Ala Val
210                 215                 220

Tyr Thr Pro Lys Ile Thr Arg Leu Leu Arg Glu Ala Gln Glu Ser Gly
225                 230                 235                 240

Ala Lys Ile Val Thr Gly Val Glu Met Phe Ile Gly Gln Ala Tyr Glu
                245                 250                 255

Gln Tyr Glu Arg Phe Thr Gly Leu Pro Ala Pro Lys Glu Leu Phe Lys
            260                 265                 270

Asn

<210> SEQ ID NO 37
<211> LENGTH: 278
<212> TYPE: PRT

<213> ORGANISM: Arabidopsis thaliana

<400> SEQUENCE: 37

Pro Asp Thr Lys Val Tyr Gly Ile Ile Gly Lys Pro Val Ser His Ser
1               5                   10                  15

Lys Ser Pro Ile Val His Asn Gln Ala Phe Lys Ser Val Asp Phe Asn
            20                  25                  30

Gly Val Tyr Val His Leu Leu Val Asp Asn Leu Val Ser Phe Leu Gln
        35                  40                  45

Ala Tyr Ser Ser Ser Asp Phe Ala Gly Phe Ser Cys Thr Ile Pro His
    50                  55                  60

Lys Glu Ala Ala Leu Gln Cys Cys Asp Glu Val Asp Pro Leu Ala Lys
65                  70                  75                  80

Ser Ile Gly Ala Val Asn Thr Ile Leu Arg Arg Lys Ser Asp Gly Lys
                85                  90                  95

Leu Leu Gly Tyr Asn Thr Asp Cys Ile Gly Ser Ile Ser Ala Ile Glu
            100                 105                 110

Asp Gly Leu Arg Ser Ser Gly Asp Pro Ser Ser Val Pro Ser Ser Ser
        115                 120                 125

Ser Pro Leu Ala Ser Lys Thr Val Val Ile Gly Ala Gly Gly Ala
    130                 135                 140

Gly Lys Ala Leu Ala Tyr Gly Ala Lys Glu Lys Gly Ala Lys Val Val
145                 150                 155                 160

Ile Ala Asn Arg Thr Tyr Glu Arg Ala Leu Glu Leu Ala Glu Ala Ile
                165                 170                 175

Gly Gly Lys Ala Leu Ser Leu Thr Asp Leu Asp Asn Tyr His Pro Glu
            180                 185                 190

Asp Gly Met Val Leu Ala Asn Thr Thr Ser Met Gly Met Gln Pro Asn
        195                 200                 205

Val Glu Glu Thr Pro Ile Ser Lys Asp Ala Leu Lys His Tyr Ala Leu
    210                 215                 220

Val Phe Asp Ala Val Tyr Thr Pro Arg Ile Thr Arg Leu Leu Arg Glu
225                 230                 235                 240

Ala Glu Glu Ser Gly Ala Ile Thr Val Ser Gly Ser Glu Met Phe Val
                245                 250                 255

Arg Gln Ala Tyr Glu Gln Phe Glu Ile Phe Thr Gly Leu Pro Ala Pro
            260                 265                 270

Lys Glu Leu Tyr Trp Gln
        275

<210> SEQ ID NO 38
<211> LENGTH: 277
<212> TYPE: PRT
<213> ORGANISM: Juglans regia

<400> SEQUENCE: 38

Pro Asp Thr Lys Val Phe Gly Ile Ile Gly Lys Pro Val His His Ser
1               5                   10                  15

Lys Ser Pro Ile Leu Tyr Asn Glu Ala Phe Lys Ser Val Cys Phe Asn
            20                  25                  30

Gly Val Tyr Ile Pro Leu Leu Val Asp Asp Ile Ala Asn Phe Leu Gln
        35                  40                  45

Thr Tyr Ser Ser Thr Asp Phe Ala Gly Phe Ser Cys Thr Ile Pro His
    50                  55                  60

Lys Glu Ala Ala Leu Lys Cys Cys Asp Glu Val Asp Pro Val Ala Lys

```
                65                  70                  75                  80
Ser Ile Gly Ala Val Asn Cys Ile Ile Arg Arg Pro Thr Asp Gly Lys
                    85                  90                  95

Leu Val Gly Tyr Asn Thr Asp Tyr Val Gly Ala Ile Ser Ala Ile Glu
                100                 105                 110

Asp Gly Leu Arg Gly Ser His Asn Ser Ser Asn Thr Ala Asp Ser Pro
            115                 120                 125

Leu Ala Gly Lys Leu Phe Val Val Ile Gly Ala Gly Ala Gly Lys
    130                 135                 140

Ala Leu Ala Tyr Gly Ala Lys Glu Lys Gly Ala Arg Val Val Ile Ala
145                 150                 155                 160

Asn Arg Thr Tyr Asp Arg Ala Arg Glu Leu Ala Asp Thr Ile Gly Gly
                165                 170                 175

Asp Ala Leu Ser Leu Ala Asp Leu Asp Asn Phe His Pro Glu Asp Gly
                180                 185                 190

Met Ile Leu Ala Asn Ser Thr Ser Ile Gly Met Gln Pro Lys Val Asp
            195                 200                 205

Glu Thr Pro Ile Pro Lys His Ala Leu Arg Ser Tyr Ser Leu Val Phe
210                 215                 220

Asp Ala Val Tyr Thr Pro Lys Met Thr Arg Leu Leu Arg Glu Ala Glu
225                 230                 235                 240

Glu Ser Gly Ala Lys Ile Val Thr Gly Leu Glu Met Phe Ile Gly Gln
                245                 250                 255

Ala Tyr Glu Gln Phe Glu Arg Phe Thr Gly Leu Pro Ala Pro Lys Glu
                260                 265                 270

Leu Phe Arg Lys Val
            275

<210> SEQ ID NO 39
<211> LENGTH: 247
<212> TYPE: PRT
<213> ORGANISM: Thermotoga maritime

<400> SEQUENCE: 39

Met Lys Phe Cys Ile Ile Gly Tyr Pro Val Arg His Ser Ile Ser Pro
1               5                   10                  15

Arg Leu Tyr Asn Glu Tyr Phe Lys Arg Ala Gly Met Asn His Ser Tyr
                20                  25                  30

Gly Met Glu Glu Ile Pro Pro Glu Ser Phe Asp Thr Glu Ile Arg Arg
            35                  40                  45

Ile Leu Glu Glu Tyr Asp Gly Phe Asn Ala Thr Ile Pro His Lys Glu
    50                  55                  60

Arg Val Met Arg Tyr Val Glu Pro Ser Glu Asp Ala Gln Arg Ile Lys
65                  70                  75                  80

Ala Val Asn Cys Val Phe Arg Gly Lys Gly Tyr Asn Thr Asp Trp Val
                85                  90                  95

Gly Val Val Lys Ser Leu Glu Gly Val Glu Lys Glu Pro Val Val
            100                 105                 110

Val Val Gly Ala Gly Gly Ala Ala Arg Ala Val Ile Tyr Ala Leu Leu
            115                 120                 125

Gln Met Gly Val Lys Asp Ile Trp Val Val Asn Arg Thr Ile Glu Arg
            130                 135                 140

Ala Lys Ala Leu Asp Phe Pro Val Lys Ile Phe Ser Leu Asp Gln Leu
145                 150                 155                 160
```

-continued

```
Asp Glu Val Val Lys Lys Ala Lys Ser Leu Phe Asn Thr Thr Ser Val
            165                 170                 175
Gly Met Lys Gly Glu Leu Pro Val Ser Asp Ser Leu Lys Asn
        180                 185                 190
Leu Ser Leu Val Tyr Asp Val Ile Tyr Phe Asp Thr Pro Leu Val Val
            195                 200                 205
Lys Ala Arg Lys Leu Gly Val Lys His Ile Ile Lys Gly Asn Leu Met
    210                 215                 220
Phe Tyr Tyr Gln Ala Met Glu Asn Leu Lys Ile Trp Gly Ile Tyr Asp
225                 230                 235                 240
Glu Glu Val Phe Lys Glu Val
                245

<210> SEQ ID NO 40
<211> LENGTH: 274
<212> TYPE: PRT
<213> ORGANISM: Streptococcus pneumoniae

<400> SEQUENCE: 40

Gly Tyr Thr Arg Leu Ala Val Val Ala Asn Pro Ile Lys His Ser
  1               5                  10                  15
Ile Ser Pro Phe Ile His Asn Arg Ala Phe Glu Ala Thr Ala Thr Asn
                 20                  25                  30
Gly Ala Tyr Val Ala Trp Glu Ile Glu Ala Ser Asp Leu Val Glu Thr
             35                  40                  45
Val Ala Asn Ile Arg Arg Tyr Gln Met Phe Gly Ile Asn Leu Ser Met
 50                  55                  60
Pro Tyr Lys Glu Gln Val Ile Pro Tyr Leu Asp Lys Leu Ser Asp Glu
 65                  70                  75                  80
Ala Arg Leu Ile Gly Ala Val Asn Thr Val Asn Glu Asn Gly Asn
                 85                  90                  95
Leu Ile Gly Tyr Asn Thr Asp Gly Lys Gly Phe Phe Lys Cys Leu Pro
            100                 105                 110
Ser Phe Thr Ile Ser Gly Lys Lys Met Thr Leu Leu Gly Ala Gly Gly
        115                 120                 125
Ala Ala Lys Ser Ile Leu Ala Gln Ala Ile Leu Asp Gly Val Ser Gln
    130                 135                 140
Ile Ser Val Phe Val Arg Ser Val Ser Met Glu Lys Thr Arg Pro Tyr
145                 150                 155                 160
Leu Asp Lys Leu Gln Glu Gln Thr Gly Phe Lys Val Asp Leu Cys Ala
                165                 170                 175
Leu Glu Tyr Val Ser Glu Leu Gln Ala Arg Ile Ala Glu Ser Asp Leu
            180                 185                 190
Leu Val Asn Ala Thr Ser Val Gly Met Asp Gly Gln Ser Ser Pro Val
        195                 200                 205
Pro Glu Asn Ile Val Leu Pro Glu Thr Leu Leu Val Ala Asp Ile Ile
    210                 215                 220
Tyr Gln Pro Phe Glu Thr Pro Phe Leu Lys Trp Ala Arg Ser Gln Gly
225                 230                 235                 240
Asn Pro Ala Val Asn Gly Leu Gly Met Leu Leu Tyr Gln Ala Ala Glu
                245                 250                 255
Ala Phe Gln Leu Trp Ile Gly Lys Glu Met Pro Thr Glu Glu Ile Trp
            260                 265                 270
Gln Ser
```

```
<210> SEQ ID NO 41
<211> LENGTH: 260
<212> TYPE: PRT
<213> ORGANISM: Aquifex aeolicus

<400> SEQUENCE: 41

Ala Gln Thr Gln Leu Tyr Gly Val Ile Gly Phe Pro Val Lys His Ser
1               5                   10                  15

Leu Ser Pro Val Phe Gln Asn Ala Leu Ile Arg Tyr Ala Gly Leu Asn
            20                  25                  30

Ala Val Tyr Leu Ala Phe Glu Ile Asn Pro Glu Glu Leu Lys Lys Ala
        35                  40                  45

Phe Glu Gly Phe Lys Ala Leu Lys Val Lys Gly Ile Asn Val Thr Val
50                  55                  60

Pro Phe Lys Glu Glu Ile Ile Pro Leu Leu Asp Tyr Val Glu Asp Thr
65                  70                  75                  80

Ala Lys Glu Ile Gly Ala Val Asn Thr Val Lys Phe Glu Asn Gly Lys
                85                  90                  95

Ala Tyr Gly Tyr Asn Thr Asp Trp Ile Gly Phe Leu Lys Ser Leu Lys
            100                 105                 110

Ser Leu Ile Pro Glu Val Lys Glu Lys Ser Ile Leu Val Leu Gly Ala
        115                 120                 125

Gly Gly Ala Ser Arg Ala Val Ile Tyr Ala Leu Val Lys Glu Gly Ala
130                 135                 140

Lys Val Phe Leu Trp Asn Arg Thr Lys Glu Lys Ala Ile Lys Leu Ala
145                 150                 155                 160

Gln Lys Phe Pro Leu Glu Val Val Asn Ser Pro Glu Glu Val Ile Asp
                165                 170                 175

Lys Val Gln Val Ile Val Asn Thr Thr Ser Val Gly Leu Lys Asp Lys
            180                 185                 190

Asp Pro Glu Ile Phe Asn Tyr Asp Leu Ile Lys Lys Asp His Val Val
        195                 200                 205

Val Asp Ile Ile Tyr Lys Glu Thr Lys Leu Leu Lys Lys Ala Lys Glu
210                 215                 220

Lys Gly Ala Lys Leu Phe Asp Gly Leu Pro Met Leu Leu Trp Gln Gly
225                 230                 235                 240

Ile Glu Ala Phe Lys Ile Trp Asn Gly Cys Glu Val Pro Tyr Ser Val
                245                 250                 255

Ala Glu Arg Ser
            260

<210> SEQ ID NO 42
<211> LENGTH: 272
<212> TYPE: PRT
<213> ORGANISM: Methanococcus jannaschii

<400> SEQUENCE: 42

Ala Lys Thr Lys Val Ile Gly Leu Ile Gly His Pro Val Glu His Ser
1               5                   10                  15

Phe Ser Pro Ile Met His Asn Ala Ala Phe Lys Asp Lys Gly Leu Asn
            20                  25                  30

Tyr Val Tyr Val Ala Phe Asp Val Leu Pro Glu Asn Leu Lys Tyr Val
        35                  40                  45

Ile Asp Gly Ala Lys Ala Leu Gly Ile Val Gly Phe Asn Val Thr Ile
50                  55                  60
```

```
Pro His Lys Ile Glu Ile Met Lys Tyr Leu Asp Glu Ile Asp Lys Asp
 65                  70                  75                  80

Ala Gln Leu Ile Gly Ala Val Asn Thr Ile Lys Ile Glu Asp Gly Lys
                 85                  90                  95

Ala Ile Gly Tyr Asn Thr Asp Gly Ile Gly Ala Arg Met Ala Leu Glu
            100                 105                 110

Glu Glu Ile Gly Arg Val Lys Asp Lys Asn Ile Val Ile Tyr Gly Ala
        115                 120                 125

Gly Gly Ala Ala Arg Ala Val Ala Phe Glu Leu Ala Lys Asp Asn Asn
    130                 135                 140

Ile Ile Ile Ala Asn Arg Thr Val Glu Lys Ala Glu Ala Leu Ala Lys
145                 150                 155                 160

Glu Ile Ala Glu Lys Leu Asn Lys Lys Phe Gly Glu Glu Val Lys Phe
                165                 170                 175

Ser Gly Leu Asp Val Asp Leu Asp Gly Val Asp Ile Ile Ile Asn Ala
            180                 185                 190

Thr Pro Ile Gly Met Tyr Pro Asn Ile Asp Val Glu Pro Ile Val Lys
        195                 200                 205

Ala Glu Lys Leu Arg Glu Asp Met Val Val Met Asp Leu Ile Tyr Asn
    210                 215                 220

Pro Leu Glu Thr Val Leu Leu Lys Glu Ala Lys Lys Val Asn Ala Lys
225                 230                 235                 240

Thr Ile Asn Gly Leu Gly Met Leu Ile Tyr Gln Gly Ala Val Ala Phe
                245                 250                 255

Lys Ile Trp Thr Gly Val Glu Pro Asn Ile Glu Val Met Lys Asn Ala
                260                 265                 270

<210> SEQ ID NO 43
<211> LENGTH: 270
<212> TYPE: PRT
<213> ORGANISM: Bacillus subtilis

<400> SEQUENCE: 43

Met Lys Lys Leu Tyr Gly Val Ile Gly Asn Pro Ile Gly His Ser Met
  1               5                  10                  15

Ser Pro Asp Ile His Asn Ala Ser Leu Lys Asp Leu Gly Leu Asp Gly
                 20                  25                  30

His Tyr His Ala Phe Lys Val Glu Glu Asn Asp Leu Glu Asp Ala Val
             35                  40                  45

Lys Gly Ile Arg Ala Leu Gly Val Gln Gly Ile Asn Val Thr Val Pro
         50                  55                  60

His Lys Val Ser Ile Met Asp Tyr Leu Asp His Ile Asp Glu Ser Ala
 65                  70                  75                  80

Lys Val Leu Gly Ala Val Asn Thr Val Arg Arg Glu Gly Asp Lys Leu
                 85                  90                  95

Val Gly Tyr Asn Thr Asp Gly Glu Gly Phe Val Lys Ser Leu Met Lys
            100                 105                 110

Val Leu Asp Lys Pro Ile Ser Glu Leu Ser Phe Leu Met Ile Gly Ala
        115                 120                 125

Gly Gly Ala Ala Arg Ala Ile Phe Thr Thr Phe Val Arg Asn Thr Pro
    130                 135                 140

Lys Lys Phe Asp Ile Cys Asn Arg Thr Leu Glu Lys Ala Lys Arg Leu
145                 150                 155                 160

Thr Glu Ala Thr Pro Ser Phe His Asn Lys Glu Val Leu Ser Ile Lys
                165                 170                 175
```

Glu Ala Glu Glu Arg Leu Glu Gln Tyr Asp Val Ile Ile His Thr Thr
                180                 185                 190

Ser Val Gly Met Tyr Pro Asn Val Asp Val Pro Leu Ser Leu Gln
            195                 200                 205

Arg Ala Ala Ser Ser Ala Val Val Cys Asp Ile Val Tyr Asn Pro Ile
        210                 215                 220

Gln Thr Ala Leu Leu Lys Glu Ala Ser Gln Lys Gly Leu Lys Thr Leu
225                 230                 235                 240

Asp Gly Val Gly Met Phe Val Glu Gln Ala Ala Leu Ser Phe Gln Leu
                245                 250                 255

Trp Thr Gly Gln Glu Pro Asn Ile Glu Lys Met Arg Ser Ile
                260                 265                 270

<210> SEQ ID NO 44
<211> LENGTH: 265
<212> TYPE: PRT
<213> ORGANISM: Escherichia coli

<400> SEQUENCE: 44

Met Glu Thr Tyr Ala Val Phe Gly Asn Pro Ile Ala His Ser Lys Ser
 1               5                  10                  15

Pro Phe Ile His Gln Gln Phe Ala Gln Gln Leu Asn Ile Glu His Pro
                20                  25                  30

Tyr Gly Arg Val Leu Ala Pro Ile Asn Asp Phe Ile Asn Thr Leu Asn
            35                  40                  45

Ala Phe Phe Ser Ala Gly Gly Lys Gly Ala Asn Val Thr Val Pro Phe
        50                  55                  60

Lys Glu Glu Ala Phe Ala Arg Ala Asp Glu Leu Thr Glu Arg Ala Ala
65                  70                  75                  80

Leu Ala Gly Ala Val Asn Thr Leu Met Arg Leu Glu Asp Gly Arg Leu
                85                  90                  95

Leu Gly Asp Asn Thr Asp Gly Val Gly Leu Leu Ser Asp Leu Glu Arg
            100                 105                 110

Leu Ser Phe Ile Arg Pro Gly Leu Arg Ile Leu Leu Ile Gly Ala Gly
        115                 120                 125

Gly Ala Ser Arg Gly Val Leu Leu Pro Leu Leu Ser Leu Asp Cys Ala
130                 135                 140

Val Thr Ile Thr Asn Arg Thr Val Ser Arg Ala Glu Glu Leu Ala Lys
145                 150                 155                 160

Leu Phe Ala His Thr Gly Ser Ile Gln Ala Leu Ser Met Asp Glu Leu
                165                 170                 175

Glu Gly His Glu Phe Asp Leu Ile Ile Asn Ala Thr Ser Ser Gly Ile
            180                 185                 190

Ser Gly Asp Ile Pro Ala Ile Pro Ser Ser Leu Ile His Pro Gly Ile
        195                 200                 205

Tyr Cys Tyr Asp Met Phe Tyr Gln Lys Gly Lys Thr Pro Phe Leu Ala
210                 215                 220

Trp Cys Glu Gln Arg Gly Ser Lys Arg Asn Ala Asp Gly Leu Gly Met
225                 230                 235                 240

Leu Val Ala Gln Ala Ala His Ala Phe Leu Leu Trp His Gly Val Leu
                245                 250                 255

Pro Asp Val Glu Pro Val Ile Lys Gln
            260                 265

<210> SEQ ID NO 45
<211> LENGTH: 266
<212> TYPE: PRT
<213> ORGANISM: Haemophilus influenzae

<400> SEQUENCE: 45

Met Asp Leu Tyr Ala Val Trp Gly Asn Pro Ile Ala Gln Ser Lys Ser
1               5                   10                  15
Pro Leu Ile Gln Asn Lys Leu Ala Ala Gln Thr His Gln Thr Met Glu
            20                  25                  30
Tyr Ile Ala Lys Leu Gly Asp Leu Asp Ala Phe Glu Gln Gln Leu Leu
        35                  40                  45
Ala Phe Phe Glu Glu Gly Ala Lys Gly Cys Asn Ile Thr Ser Pro Phe
    50                  55                  60
Lys Glu Arg Ala Tyr Gln Leu Ala Asp Glu Tyr Ser Gln Arg Ala Lys
65                  70                  75                  80
Leu Ala Glu Ala Cys Asn Thr Leu Lys Lys Leu Asp Asp Gly Lys Leu
                85                  90                  95
Tyr Ala Asp Asn Thr Asp Gly Ile Gly Leu Val Thr Asp Leu Gln Arg
            100                 105                 110
Leu Asn Trp Leu Arg Pro Asn Gln His Val Leu Ile Leu Gly Ala Gly
        115                 120                 125
Gly Ala Thr Lys Gly Val Leu Leu Pro Leu Leu Gln Ala Gln Gln Asn
    130                 135                 140
Ile Val Leu Ala Asn Arg Thr Phe Ser Lys Thr Lys Glu Leu Ala Glu
145                 150                 155                 160
Arg Phe Gln Pro Tyr Gly Asn Ile Gln Ala Val Ser Met Asp Ser Ile
                165                 170                 175
Pro Leu Gln Thr Tyr Asp Leu Val Ile Asn Ala Thr Ser Ala Gly Leu
            180                 185                 190
Ser Gly Gly Thr Ala Ser Val Asp Ala Glu Ile Leu Lys Leu Gly Ser
        195                 200                 205
Ala Phe Tyr Asp Met Gln Tyr Ala Lys Gly Thr Asp Thr Pro Phe Ile
    210                 215                 220
Ala Leu Cys Lys Ser Leu Gly Leu Thr Asn Val Ser Asp Gly Phe Gly
225                 230                 235                 240
Met Leu Val Ala Gln Ala Ala His Ser Phe His Leu Trp Arg Gly Val
                245                 250                 255
Met Pro Asp Phe Val Ser Val Tyr Glu Gln
            260                 265

<210> SEQ ID NO 46
<211> LENGTH: 346
<212> TYPE: PRT
<213> ORGANISM: Rana nigromaculata

<400> SEQUENCE: 46

Asn Cys Thr Val Arg Arg Asn Met Ile Arg Lys Asp Ile Phe Arg Met
1               5                   10                  15
Thr Thr Ala Glu Lys Asp Lys Leu Ile Ala Tyr Leu Asn Leu Ala Lys
            20                  25                  30
His Thr Ile Ser Pro Asp Tyr Val Ile Ala Thr Gly Thr Tyr Glu Gln
        35                  40                  45
Met Asn Asn Gly Ser Asn Pro Met Phe Ala Asp Ile Ser Ala Tyr Asp
    50                  55                  60
Leu Phe Val Trp Ile His Tyr Tyr Ala Ser Arg Asp Ala Phe Leu Glu

```
                65                  70                  75                  80
Asp Gly Ser Val Trp Ala Asp Ile Asp Phe Ala His Glu Ala Pro Gly
                            85                  90                  95
Phe Leu Pro Trp His Arg Phe Tyr Leu Leu Trp Glu Arg Glu Ile
                100                 105                 110
Gln Lys Val Thr Gly Asp Asp Asn Phe Thr Ile Pro Phe Trp Asp Trp
                115                 120                 125
Arg Asp Ala Gln Gln Cys Glu Leu Cys Thr Asp Glu Phe Phe Gly Gly
            130                 135                 140
Thr His Pro Thr Ser Asn Asn Leu Leu Ser Pro Ala Ser Phe Phe Ser
145                 150                 155                 160
Ser Trp Gln Ile Ile Cys Ser Arg Pro Glu Glu Tyr Asn Ser Leu Arg
                        165                 170                 175
Ile Ile Cys Asn Gly Thr Asn Glu Gly Pro Leu Leu Arg Ser Pro Gly
                180                 185                 190
Arg His Asp Arg Asn Arg Thr Pro Arg Leu Pro Thr Ser Ala Asp Val
                195                 200                 205
Glu Ala Cys Leu Ser Leu Thr Asp Tyr Glu Thr Gly Ala Met Asp Arg
            210                 215                 220
Ser Ala Asn Phe Ser Phe Arg Asn Thr Leu Glu Gly Phe Ala Val Pro
225                 230                 235                 240
Thr Ser Gly Ile Ala Asn Arg Ser Gln Ser Ser Met His Asn Ser Leu
                        245                 250                 255
His Val Phe Leu Asn Gly Ser Met Ser Ser Val Gln Gly Ser Ala Asn
                260                 265                 270
Asp Pro Ile Phe Val Leu His His Ala Phe Val Asp Ser Leu Phe Glu
                275                 280                 285
Gln Trp Leu Arg Arg His Gln Pro Ser Leu Asp Val Tyr Pro Glu Ala
            290                 295                 300
Asn Ala Pro Val Gly His Asn Arg Glu Tyr Asn Met Val Pro Phe Ile
305                 310                 315                 320
Pro Leu Phe Thr Asn Gly Glu Phe Phe Val Gln Ser Arg Asp Leu Gly
                        325                 330                 335
Tyr Asp Tyr Asp Tyr Leu Ala Glu Ser Gly
                340                 345
```

<210> SEQ ID NO 47
<211> LENGTH: 351
<212> TYPE: PRT
<213> ORGANISM: Homo sapiens

<400> SEQUENCE: 47

```
Ala Cys Asp Gln Arg Val Leu Ile Val Arg Arg Asn Leu Leu Asp Leu
1               5                   10                  15
Ser Lys Glu Glu Lys Asn His Phe Val Arg Ala Leu Asp Met Ala Lys
                20                  25                  30
Arg Thr Thr His Pro Leu Phe Val Ile Ala Thr Arg Arg Ser Glu Glu
            35                  40                  45
Ile Leu Gly Pro Asp Gly Asn Thr Pro Gln Phe Glu Asn Ile Ser Ile
        50                  55                  60
Tyr Asn Tyr Phe Val Trp Thr His Tyr Tyr Ser Val Lys Lys Thr Phe
65                  70                  75                  80
Leu Gly Val Gly Gln Glu Ser Phe Gly Glu Val Asp Phe Ser His Glu
                85                  90                  95
```

```
Gly Pro Ala Phe Leu Thr Trp His Arg Tyr His Leu Arg Leu Glu
            100                 105                 110

Lys Asp Met Gln Glu Met Leu Gln Glu Pro Ser Phe Ser Leu Pro Tyr
            115                 120                 125

Trp Asn Phe Ala Thr Gly Lys Asn Val Cys Asp Ile Cys Thr Asp Asp
            130                 135                 140

Leu Met Gly Ser Arg Ser Asn Phe Asp Ser Thr Leu Ile Ser Pro Asn
145                 150                 155                 160

Ser Val Phe Ser Gln Trp Arg Val Val Cys Asp Ser Leu Glu Asp Tyr
                165                 170                 175

Asp Thr Leu Gly Thr Leu Cys Asn Ser Thr Glu Asp Gly Pro Ile Arg
            180                 185                 190

Arg Asn Pro Ala Gly Asn Val Ala Arg Pro Met Val Gln Arg Leu Pro
            195                 200                 205

Glu Pro Gln Asp Val Ala Gln Cys Leu Glu Val Gly Leu Phe Asp Thr
            210                 215                 220

Pro Pro Phe Tyr Ser Asn Ser Thr Asn Ser Phe Arg Asn Thr Val Glu
225                 230                 235                 240

Gly Tyr Ser Asp Pro Thr Gly Lys Tyr Asp Pro Ala Val Arg Ser Leu
                245                 250                 255

His Asn Leu Ala His Leu Phe Leu Asn Gly Thr Gly Gly Gln Thr His
            260                 265                 270

Leu Ser Pro Asn Asp Pro Ile Phe Val Leu Leu His Thr Phe Thr Asp
            275                 280                 285

Ala Val Phe Asp Glu Trp Leu Arg Arg Tyr Asn Ala Asp Ile Ser Thr
            290                 295                 300

Phe Pro Leu Glu Asn Ala Pro Ile Gly His Asn Arg Gln Tyr Asn Met
305                 310                 315                 320

Val Pro Phe Trp Pro Pro Val Thr Asn Thr Glu Met Phe Val Thr Ala
                325                 330                 335

Pro Asp Asn Leu Gly Tyr Thr Tyr Glu Ile Gln Trp Pro Ser Arg
            340                 345                 350

<210> SEQ ID NO 48
<211> LENGTH: 373
<212> TYPE: PRT
<213> ORGANISM: Neurospora crassa

<400> SEQUENCE: 48

Ser Thr Asp Ile Lys Phe Ala Ile Thr Gly Val Pro Thr Thr Pro Ser
1                   5                   10                  15

Ser Asn Gly Ala Val Pro Leu Arg Arg Glu Leu Arg Asp Leu Gln Gln
            20                  25                  30

Asn Tyr Pro Glu Gln Phe Asn Leu Tyr Leu Leu Gly Leu Arg Asp Phe
            35                  40                  45

Gln Gly Leu Asp Glu Ala Lys Leu Asp Ser Tyr Tyr Gln Val Ala Gly
        50                  55                  60

Ile His Gly Met Pro Phe Lys Pro Trp Ala Gly Val Pro Ser Asp Thr
65                  70                  75                  80

Asp Trp Ser Gln Pro Gly Ser Ser Gly Phe Gly Gly Tyr Cys Thr His
                85                  90                  95

Ser Ser Ile Leu Phe Ile Thr Trp His Arg Pro Tyr Leu Ala Leu Tyr
            100                 105                 110

Glu Gln Ala Leu Tyr Ala Ser Val Gln Ala Val Ala Gln Lys Phe Pro
            115                 120                 125
```

Val Glu Gly Gly Leu Arg Ala Lys Tyr Val Ala Ala Lys Asp Phe
    130                 135                 140

Arg Ala Pro Tyr Phe Asp Trp Ala Ser Gln Pro Pro Lys Gly Thr Leu
145                 150                 155                 160

Ala Phe Pro Glu Ser Leu Ser Ser Arg Thr Ile Gln Val Val Asp Val
                165                 170                 175

Asp Gly Lys Thr Lys Ser Ile Asn Asn Pro Leu His Arg Phe Thr Phe
            180                 185                 190

His Pro Val Asn Pro Ser Pro Gly Asp Phe Ser Ala Ala Trp Ser Arg
        195                 200                 205

Tyr Pro Ser Thr Val Arg Tyr Pro Asn Arg Leu Thr Gly Ala Ser Arg
    210                 215                 220

Asp Glu Arg Ile Ala Pro Ile Leu Ala Asn Glu Leu Ala Ser Leu Arg
225                 230                 235                 240

Asn Asn Val Ser Leu Leu Leu Ser Tyr Lys Asp Phe Asp Ala Phe
                245                 250                 255

Ser Tyr Asn Arg Trp Asp Pro Asn Thr Asn Pro Gly Asp Phe Gly Ser
                260                 265                 270

Leu Glu Asp Val His Asn Glu Ile His Asp Arg Thr Gly Gly Asn Gly
            275                 280                 285

His Met Ser Ser Leu Glu Val Ser Ala Phe Asp Pro Leu Phe Trp Leu
        290                 295                 300

His His Val Asn Val Asp Arg Leu Trp Ser Ile Trp Gln Asp Leu Asn
305                 310                 315                 320

Pro Asn Ser Phe Met Thr Pro Arg Pro Ala Pro Tyr Ser Thr Phe Val
                325                 330                 335

Ala Gln Glu Gly Glu Ser Gln Ser Lys Ser Thr Pro Leu Glu Pro Phe
            340                 345                 350

Trp Asp Lys Ser Ala Ala Asn Phe Trp Thr Ser Glu Gln Val Lys Asp
        355                 360                 365

Ser Ile Thr Phe Gly
    370

<210> SEQ ID NO 49
<211> LENGTH: 299
<212> TYPE: PRT
<213> ORGANISM: Octopus dofleini

<400> SEQUENCE: 49

Gly Lys Val Leu Asp Ser Ser Leu Pro Val Pro Ser Met Ile Tyr
1               5                   10                  15

Val Pro Ala Lys Glu Phe Thr Lys Glu Ile Lys Glu Ala Val Arg
                20                  25                  30

Gly Thr Ile Ile Arg Lys Asn Val Asn Ser Leu Thr Pro Ser Asp Ile
            35                  40                  45

Lys Glu Leu Arg Asp Ala Met Ala Lys Val Gln Ala Asp Thr Ser Asp
50                  55                  60

Asn Gly Tyr Gln Lys Ile Ala Ser Tyr His Gly Ile Pro Leu Ser Cys
65                  70                  75                  80

His Tyr Glu Asn Gly Thr Ala Tyr Ala Cys Cys Gln His Gly Met Val
                85                  90                  95

Thr Phe Pro Asn Trp His Arg Leu Leu Thr Lys Gln Met Glu Asp Ala
                100                 105                 110

Leu Val Ala Lys Gly Ser His Val Gly Ile Pro Tyr Trp Asp Trp Thr

```
            115                 120                 125
Thr Thr Phe Ala Asn Leu Pro Val Leu Val Thr Glu Glu Lys Asp Asn
    130                 135                 140

Ser Phe His His Ala His Ile Asp Val Ala Asn Thr Asp Thr Thr Arg
145                 150                 155                 160

Ser Pro Arg Ala Gln Leu Phe Asp Asp Pro Glu Lys Gly Asp Lys Ser
                165                 170                 175

Phe Phe Tyr Arg Gln Ile Ala Leu Ala Leu Glu Gln Thr Asp Phe Cys
                180                 185                 190

Asp Phe Glu Ile Gln Phe Glu Ile Gly His Asn Ala Ile His Ser Trp
                195                 200                 205

Val Gly Gly Ser Ser Pro Tyr Gly Met Ser Thr Leu His Tyr Thr Ser
    210                 215                 220

Tyr Asp Pro Leu Phe Tyr Leu His His Ser Asn Thr Asp Arg Ile Trp
225                 230                 235                 240

Ser Val Trp Gln Ala Leu Gln Lys Tyr Arg Gly Leu Pro Tyr Asn Thr
                245                 250                 255

Ala Asn Cys Glu Ile Asn Lys Leu Val Lys Pro Leu Lys Pro Phe Asn
                260                 265                 270

Leu Asp Thr Asn Pro Asn Ala Val Thr Lys Ala His Ser Thr Gly Ala
            275                 280                 285

Thr Ser Phe Asp Tyr His Lys Leu Gly Tyr Asp
        290                 295

<210> SEQ ID NO 50
<211> LENGTH: 309
<212> TYPE: PRT
<213> ORGANISM: Octopus dofleini

<400> SEQUENCE: 50

Ile Val Ala Gln Asn Gly Thr Glu Leu Pro Ala Ser Ile Leu Pro Glu
1               5                   10                  15

Ala Thr Val Ile Arg Ile Pro Pro Ser Lys Gln Asp Ala Asp Ile Asp
                20                  25                  30

Ile Pro Leu Asn His Ile Arg Arg Asn Val Glu Ser Leu Asp Glu Arg
            35                  40                  45

Asp Ile Gln Asn Leu Met Ala Ala Leu Thr Arg Val Lys Lys Asp Glu
        50                  55                  60

Ser Asp His Gly Phe Gln Thr Ile Ala Ser Tyr His Gly Ser Thr Leu
65                  70                  75                  80

Cys Pro Ser Pro Glu Glu Pro Lys Tyr Ala Cys Cys Leu His Gly Met
                85                  90                  95

Pro Val Phe Pro His Trp His Arg Val Tyr Leu Leu His Phe Glu Asp
                100                 105                 110

Ser Met Arg Arg His Gly Ser Ser Val Ala Thr Pro Tyr Trp Asp Trp
            115                 120                 125

Thr Gln Pro Gly Thr Lys Leu Pro Arg Leu Leu Ala Asp Ser Asp Tyr
        130                 135                 140

Tyr Asp Ala Trp Thr Asp Asn Val Thr Glu Asn Pro Phe Leu Arg Gly
145                 150                 155                 160

Tyr Ile Thr Ser Glu Asp Thr Tyr Thr Val Arg Asp Val Lys Pro Glu
                165                 170                 175

Leu Phe Glu Ile Gly Gly Gly Glu Gly Ser Thr Leu Tyr Gln Gln Val
            180                 185                 190
```

```
Leu Leu Met Leu Glu Gln Glu Asp Tyr Cys Asp Phe Glu Val Gln Phe
            195                 200                 205

Glu Val Val His Asn Ser Ile His Tyr Leu Val Gly Gly His Gln Lys
210                 215                 220

Tyr Ala Met Ser Ser Leu Val Tyr Ser Ser Phe Asp Pro Ile Phe Tyr
225                 230                 235                 240

Val His His Ser Met Val Asp Arg Leu Trp Ala Ile Trp Gln Ala Leu
                245                 250                 255

Gln Glu His Arg His Leu Pro Phe Asp Lys Ala Tyr Cys Ala Leu Glu
            260                 265                 270

Gln Leu Ser Phe Pro Met Lys Pro Phe Val Trp Glu Ser Asn Pro Asn
        275                 280                 285

Leu His Thr Arg Ala Ala Ser Thr Pro Gln His Leu Phe Asp Tyr Asn
290                 295                 300

Lys Leu Gly Tyr Lys
305

<210> SEQ ID NO 51
<211> LENGTH: 293
<212> TYPE: PRT
<213> ORGANISM: Octopus dofleini

<400> SEQUENCE: 51

Gly Asn Glu Tyr Leu Val Arg Lys Asn Val Glu Arg Leu Ser Leu Ser
1               5                   10                  15

Glu Met Asn Ser Leu Ile His Ala Phe Arg Arg Met Gln Lys Asp Lys
            20                  25                  30

Ser Ser Asp Gly Phe Glu Ala Ile Ala Ser Phe His Ala Leu Pro Pro
        35                  40                  45

Leu Cys Pro Ser Pro Thr Ala Lys His Arg His Ala Cys Cys Leu His
    50                  55                  60

Gly Met Ala Thr Phe Pro His Trp His Arg Leu Tyr Val Val Gln Phe
65                  70                  75                  80

Glu Gln Ala Leu His Arg His Gly Ala Thr Val Gly Val Pro Tyr Trp
                85                  90                  95

Asp Trp Thr Arg Pro Ile Ser Lys Ile Pro Asp Phe Ile Ala Ser Glu
            100                 105                 110

Lys Tyr Ser Asp Pro Phe Thr Lys Ile Glu Val Tyr Asn Pro Phe Asn
        115                 120                 125

His Gly His Ile Ser Phe Ile Ser Glu Asp Thr Thr Thr Lys Arg Glu
    130                 135                 140

Val Ser Glu Tyr Leu Phe Glu His Pro Val Leu Gly Lys Gln Thr Trp
145                 150                 155                 160

Leu Phe Asp Asn Ile Ala Leu Ala Leu Glu Gln Thr Asp Tyr Cys Asp
                165                 170                 175

Phe Glu Ile Gln Leu Glu Ile Val His Asn Ala Ile His Ser Trp Ile
            180                 185                 190

Gly Gly Lys Glu Glu His Ser Leu Asn His Leu His Tyr Ala Ala Tyr
        195                 200                 205

Asp Pro Ile Phe Tyr Leu His His Ser Asn Val Asp Arg Leu Trp Val
    210                 215                 220

Ile Trp Gln Glu Leu Gln Lys Leu Arg Gly Leu Asn Ala Tyr Glu Ser
225                 230                 235                 240

His Cys Ala Leu Glu Leu Met Lys Val Pro Leu Lys Pro Phe Ser Phe
                245                 250                 255
```

```
Gly Ala Pro Tyr Asn Leu Asn Asp Leu Thr Thr Lys Leu Ser Lys Pro
        260                 265                 270

Glu Asp Met Phe Arg Tyr Lys Asp Asn Phe His Tyr Glu Tyr Asp Ile
        275                 280                 285

Leu Asp Ile Asn Ser
    290

<210> SEQ ID NO 52
<211> LENGTH: 292
<212> TYPE: PRT
<213> ORGANISM: Rapana thomasiana

<400> SEQUENCE: 52

Thr His Arg Asn Leu Val Arg Lys Ser Val Arg Asn Leu Ser Pro Ala
1               5                   10                  15

Glu Arg Ala Ser Leu Val His Ala Leu Lys Ser Leu Gln Glu Asp Ser
            20                  25                  30

Ser Ala Asp Gly Phe Gln Ser Leu Ala Ser Phe His Ala Gln Pro Pro
        35                  40                  45

Leu Cys Pro Tyr Pro Ala Ala Asn Lys Ala Phe Ala Cys Cys Val His
    50                  55                  60

Gly Met Ala Thr Phe Pro Glu Trp His Arg Leu Tyr Thr Val Gln Phe
65                  70                  75                  80

Glu Asp Ala Leu Arg Arg His Gly Ser Val Val Gly Ile Pro Tyr Trp
                85                  90                  95

Asp Thr Val Val Pro Gln Glu Asp Leu Pro Ala Phe Phe Asn Asp Glu
            100                 105                 110

Ile Trp Asp Asp Ala Leu Phe His Ala Asn Phe Thr Asn Pro Phe Asn
        115                 120                 125

Gly Ala Asp Ile Asp Phe Asn His Gln Lys Ile Ala Arg Asp Ile Asn
    130                 135                 140

Val Asp Lys Leu Ala Lys Glu Gly Pro Lys Gly Tyr Asp Thr Trp Ser
145                 150                 155                 160

Phe Lys Gln Tyr Ile Tyr Ala Leu Glu Gln Glu Asp Tyr Cys Asp Phe
                165                 170                 175

Glu Val Gln Phe Glu Ile Ala His Asn Ala Ile His Ala Trp Val Gly
            180                 185                 190

Gly Thr Glu Glu Tyr Ser Met Gly His Leu His Tyr Ala Ser Tyr Asp
        195                 200                 205

Pro Val Phe Ile Leu His His Ser Asn Thr Asp Arg Leu Phe Ala Leu
    210                 215                 220

Trp Gln Glu Leu Gln Lys Phe Arg Gly His Asp Pro Asn Glu Val Asn
225                 230                 235                 240

Cys Ala Leu Glu Met Met Arg Glu Pro Leu Lys Pro Phe Ser Phe Gly
                245                 250                 255

Ala Pro Tyr Asn Leu Asn Pro Thr Thr Lys Glu His Ser Lys Pro Glu
            260                 265                 270

Asp Thr Phe Asp Tyr Lys Gly His Phe His Tyr Glu Tyr Asp His Leu
        275                 280                 285

Glu Leu Gln Gly
    290

<210> SEQ ID NO 53
<211> LENGTH: 320
<212> TYPE: PRT
```

<213> ORGANISM: Vicia faba

<400> SEQUENCE: 53

```
Gly Thr Thr Pro Pro Asn Ile Asn Cys Cys Pro Pro Tyr Ser Thr Lys
 1               5                  10                  15

Ile Thr Asp Phe Lys Phe Pro Ser Asn Gln Pro Leu Arg Val Arg Gln
             20                  25                  30

Ala Ala His Leu Val Asp Asn Glu Phe Leu Glu Lys Tyr Lys Lys Ala
         35                  40                  45

Thr Glu Leu Met Lys Ala Leu Pro Ser Asn Asp Pro Arg Asn Phe Thr
 50                  55                  60

Gln Gln Ala Asn Ile His Cys Ala Tyr Cys Asp Gly Ala Tyr Ser Gln
 65                  70                  75                  80

Ile Gly Phe Pro Asp Leu Lys Leu Gln Val His Gly Ser Trp Leu Phe
             85                  90                  95

Phe Pro Phe His Arg Trp Tyr Leu Tyr Phe Tyr Glu Arg Ile Leu Gly
            100                 105                 110

Ser Leu Ile Asn Asp Pro Thr Phe Ala Leu Pro Phe Trp Asn Tyr Asp
            115                 120                 125

Ala Pro Asp Gly Met Gln Leu Pro Thr Ile Tyr Ala Asp Lys Ala Ser
130                 135                 140

Pro Leu Tyr Asp Glu Leu Arg Asn Ala Ser His Gln Pro Pro Thr Leu
145                 150                 155                 160

Ile Asp Leu Asn Phe Cys Asp Ile Gly Ser Asp Ile Asp Arg Asn Glu
                165                 170                 175

Leu Ile Lys Thr Asn Leu Ser Ile Met Tyr Arg Gln Val Tyr Ser Asn
            180                 185                 190

Gly Lys Thr Ser Arg Leu Phe Leu Gly Asn Pro Tyr Arg Ala Gly Asp
        195                 200                 205

Ala Glu Pro Gln Gly Ala Gly Ser Ile Glu Asn Val Pro His Ala Pro
210                 215                 220

Val His Thr Trp Thr Gly Asp Asn Thr Gln Thr Asn Ile Glu Asp Met
225                 230                 235                 240

Gly Ile Phe Tyr Ser Ala Ala Arg Asp Pro Ile Phe Tyr Ser His His
                245                 250                 255

Ser Asn Val Asp Arg Leu Trp Tyr Ile Trp Lys Thr Leu Gly Gly Lys
            260                 265                 270

Lys His Asp Phe Thr Asp Lys Asp Trp Leu Glu Ser Gly Phe Leu Phe
        275                 280                 285

Tyr Asp Glu Asn Lys Asn Leu Val Arg Val Asn Val Lys Asp Ser Leu
290                 295                 300

Asp Ile Asp Lys Leu Gly Tyr Ala Tyr Gln Asp Val Pro Ile Pro Trp
305                 310                 315                 320
```

<210> SEQ ID NO 54
<211> LENGTH: 318
<212> TYPE: PRT
<213> ORGANISM: Malus domestica

<400> SEQUENCE: 54

```
Gly Ala Val Pro Thr Asn Cys Cys Pro Pro Ser Thr Lys Ile Ile
 1               5                  10                  15

Asp Phe Lys Leu Pro Ala Pro Ala Lys Leu Arg Ile Arg Pro Pro Ala
             20                  25                  30

His Ala Val Asp Gln Ala Tyr Arg Asp Lys Tyr Tyr Lys Ala Met Glu
```

```
                  35                  40                  45
Leu Met Lys Ala Leu Pro Asp Asp Pro Arg Ser Phe Lys Gln Gln
 50                  55                  60

Ala Ala Val His Cys Ala Tyr Cys Asp Gly Ala Tyr Asp Gln Val Gly
 65                  70                  75                  80

Phe Pro Glu Leu Glu Leu Gln Ile His Asn Ser Trp Leu Phe Phe Pro
                 85                  90                  95

Phe His Arg Tyr Tyr Leu Tyr Phe Glu Lys Ile Leu Gly Lys Leu
                    100                 105                 110

Ile Asn Asp Pro Thr Phe Ala Leu Pro Phe Trp Asn Trp Asp Ser Pro
                115                 120                 125

Ala Gly Met Pro Leu Pro Ala Ile Tyr Ala Asp Pro Lys Ser Pro Leu
               130                 135                 140

Tyr Asp Lys Leu Arg Ser Ala Asn His Gln Pro Pro Thr Leu Val Asp
145                 150                 155                 160

Leu Asp Tyr Asn Gly Thr Glu Asp Asn Val Ser Lys Glu Thr Thr Ile
                    165                 170                 175

Asn Ala Asn Leu Lys Ile Met Tyr Arg Gln Met Val Ser Asn Ser Lys
                180                 185                 190

Asn Ala Lys Leu Phe Phe Gly Asn Pro Tyr Arg Ala Gly Asp Glu Pro
               195                 200                 205

Asp Pro Gly Gly Gly Ser Ile Glu Gly Thr Pro His Ala Pro Val His
210                 215                 220

Leu Trp Thr Gly Asp Asn Thr Gln Pro Asn Phe Glu Asp Met Gly Asn
225                 230                 235                 240

Phe Tyr Ser Ala Gly Arg Asp Pro Ile Phe Phe Ala His His Ser Asn
                    245                 250                 255

Val Asp Arg Met Trp Ser Ile Trp Lys Thr Leu Gly Gly Lys Arg Thr
                260                 265                 270

Asp Leu Thr Asp Ser Asp Trp Leu Asp Ser Gly Phe Leu Phe Tyr Asn
               275                 280                 285

Glu Asn Ala Glu Leu Val Arg Val Lys Val Arg Asp Cys Leu Glu Thr
290                 295                 300

Lys Asn Leu Gly Tyr Val Tyr Gln Asp Val Asp Ile Pro Trp
305                 310                 315

<210> SEQ ID NO 55
<211> LENGTH: 320
<212> TYPE: PRT
<213> ORGANISM: Ipomoea batatas

<400> SEQUENCE: 55

Gly Ala Val Val Asp Asn Cys Cys Pro Pro Val Ala Ser Asn Ile Val
 1               5                  10                  15

Asp Tyr Lys Leu Pro Ala Val Thr Thr Met Lys Val Arg Pro Ala Ala
                20                  25                  30

His Thr Met Asp Lys Asp Ala Ile Ala Lys Phe Ala Lys Ala Val Glu
                35                  40                  45

Leu Met Lys Ala Leu Pro Ala Asp Asp Pro Arg Asn Phe Tyr Gln Gln
 50                  55                  60

Ala Leu Val His Cys Ala Tyr Cys Asn Gly Gly Tyr Asp Gln Val Asn
 65                  70                  75                  80

Phe Pro Asp Gln Glu Ile Gln Val His Asn Ser Trp Leu Phe Phe Pro
                 85                  90                  95
```

```
Phe His Arg Trp Tyr Leu Tyr Phe Tyr Glu Arg Ile Leu Gly Lys Leu
            100                 105                 110

Ile Gly Asp Pro Ser Phe Gly Leu Pro Phe Trp Asn Trp Asp Asn Pro
            115                 120                 125

Gly Gly Met Val Leu Pro Asp Phe Leu Asn Asp Ser Thr Ser Ser Leu
        130                 135                 140

Tyr Asp Ser Asn Arg Asn Gln Ser His Leu Pro Pro Val Val Val Asp
145                 150                 155                 160

Leu Gly Tyr Asn Gly Ala Asp Thr Asp Val Thr Asp Gln Gln Arg Ile
                165                 170                 175

Thr Asp Asn Leu Ala Leu Met Tyr Lys Gln Met Val Thr Asn Ala Gly
            180                 185                 190

Thr Ala Glu Leu Phe Leu Gly Lys Ala Tyr Arg Ala Gly Asp Ala Pro
            195                 200                 205

Ser Pro Gly Ala Gly Ser Ile Glu Thr Ser Pro His Ile Pro Ile His
        210                 215                 220

Arg Trp Val Gly Asp Pro Arg Asn Thr Asn Asn Glu Asp Met Gly Asn
225                 230                 235                 240

Phe Tyr Ser Ala Gly Arg Asp Ile Ala Phe Tyr Cys His His Ser Asn
                245                 250                 255

Val Asp Arg Met Trp Thr Ile Trp Gln Gln Leu Ala Gly Lys Pro Arg
            260                 265                 270

Lys Arg Asp Tyr Thr Asp Ser Asp Trp Leu Asn Ala Thr Phe Leu Phe
            275                 280                 285

Tyr Asp Glu Asn Gly Gln Ala Val Lys Val Arg Ile Gly Asp Ser Leu
        290                 295                 300

Asp Asn Gln Lys Met Gly Tyr Lys Tyr Ala Lys Thr Pro Leu Pro Trp
305                 310                 315                 320

<210> SEQ ID NO 56
<211> LENGTH: 329
<212> TYPE: PRT
<213> ORGANISM: Lycopersicon esculentum

<400> SEQUENCE: 56

Asn Gln Val Val Ser Tyr Ser Cys Cys Ala Pro Lys Pro Asp Asp Met
1               5                   10                  15

Glu Lys Val Pro Tyr Tyr Lys Phe Pro Ser Met Thr Lys Leu Arg Val
            20                  25                  30

Arg Gln Pro Ala His Glu Ala Asp Glu Tyr Ile Ala Lys Tyr Asn
            35                  40                  45

Val Ser Val Thr Lys Met Arg Asp Leu Asp Lys Thr Gln Pro Leu Asn
50                  55                  60

Pro Ile Gly Phe Lys Gln Gln Ala Asn Ile His Cys Ala Tyr Cys Asn
65                  70                  75                  80

Gly Ala Tyr Arg Ile Gly Gly Lys Glu Leu Gln Val His Asn Ser Trp
                85                  90                  95

Leu Phe Phe Pro Phe His Arg Trp Tyr Leu Tyr Phe Tyr Glu Ser Asn
            100                 105                 110

Ala Gly Lys Leu Ile Asp Asp Pro Thr Phe Ala Leu Pro Tyr Trp Asn
            115                 120                 125

Trp Asp His Pro Lys Gly Met Arg Phe Pro Ala Met Tyr Asp Arg Glu
        130                 135                 140

Gly Thr Phe Leu Phe Asp Glu Thr Arg Asp Gln Ser His Arg Asn Gly
145                 150                 155                 160
```

```
Thr Val Ile Asp Leu Gly Phe Phe Gly Asn Glu Val Glu Thr Thr Gln
                165                 170                 175

Leu Gln Met Met Ser Asn Asn Leu Thr Leu Met Tyr Arg Gln Met Val
            180                 185                 190

Thr Asn Ala Pro Cys Pro Arg Met Phe Phe Gly Asp Leu Met Ile Ser
        195                 200                 205

Gly Ile Thr Leu Asn Ser Pro Gly Thr Ile Glu Asn Ile Pro His Gly
    210                 215                 220

Pro Val His Ile Trp Ser Gly Thr Val Arg Gly Ser Thr Leu Pro Asn
225                 230                 235                 240

Gly Ala Ile Ser Lys Arg Gly Glu Tyr Gly His Phe Tyr Ser Ala Gly
                245                 250                 255

Leu Asp Pro Val Phe Phe Cys His His Ser Asn Val Asp Arg Met Trp
            260                 265                 270

Ser Glu Trp Lys Ala Thr Gly Gly Lys Arg Thr Asp Ile Thr His Lys
        275                 280                 285

Asp Trp Leu Asn Ser Glu Phe Phe Tyr Asp Glu Asn Glu Asn Pro
    290                 295                 300

Tyr Arg Val Lys Val Arg Asp Cys Leu Asp Thr Lys Lys Met Gly Tyr
305                 310                 315                 320

Asp Tyr Lys Pro Met Arg Thr Pro Trp
                325

<210> SEQ ID NO 57
<211> LENGTH: 322
<212> TYPE: PRT
<213> ORGANISM: Solanum Tuberosum

<400> SEQUENCE: 57

Gly Val Asp Val Thr Tyr Ser Cys Cys Pro Pro Val Pro Asp Asp Ile
1               5                   10                  15

Asp Ser Val Pro Tyr Tyr Lys Phe Pro Pro Met Thr Lys Leu Arg Ile
                20                  25                  30

Arg Pro Pro Ala His Ala Ala Asp Glu Glu Tyr Val Ala Lys Tyr Gln
            35                  40                  45

Leu Ala Thr Ser Arg Met Arg Glu Leu Asp Lys Asp Ser Phe Asp Pro
    50                  55                  60

Leu Gly Phe Lys Gln Gln Ala Asn Ile His Cys Ala Tyr Cys Asn Gly
65                  70                  75                  80

Ala Tyr Lys Val Gly Gly Lys Glu Leu Gln Val His Phe Ser Trp Leu
                85                  90                  95

Phe Phe Pro Phe His Arg Trp Tyr Leu Tyr Phe Tyr Glu Arg Ile Leu
            100                 105                 110

Gly Ser Leu Ile Asn Asp Pro Thr Phe Ala Leu Pro Tyr Trp Asn Trp
    115                 120                 125

Asp His Pro Lys Gly Met Arg Ile Pro Pro Met Phe Asp Arg Glu Gly
130                 135                 140

Ser Ser Leu Tyr Asp Asp Lys Arg Asn Gln Asn His Arg Asn Gly Thr
145                 150                 155                 160

Ile Ile Asp Leu Gly His Phe Gly Gln Glu Val Asp Thr Pro Gln Leu
                165                 170                 175

Gln Ile Met Thr Asn Asn Leu Thr Leu Met Tyr Arg Gln Met Val Thr
            180                 185                 190

Asn Ala Pro Cys Pro Ser Gln Phe Phe Gly Ala Ala Tyr Pro Leu Gly
```

```
                195                 200                 205
Thr Glu Pro Ser Pro Gly Met Gly Thr Ile Glu Asn Ile Pro His Thr
    210                 215                 220

Pro Val His Ile Trp Thr Gly Asp Ser Pro Arg Gln Lys Asn Gly Glu
225                 230                 235                 240

Asn Met Gly Asn Phe Tyr Ser Ala Gly Leu Asp Pro Ile Phe Tyr Cys
                245                 250                 255

His His Ala Asn Val Asp Arg Met Trp Asp Glu Trp Lys Leu Ile Gly
            260                 265                 270

Gly Lys Arg Arg Asp Leu Ser Asn Lys Asp Trp Leu Asn Ser Glu Phe
        275                 280                 285

Phe Phe Tyr Asp Glu Asn Arg Asn Pro Tyr Arg Val Lys Val Arg Asp
    290                 295                 300

Cys Leu Asp Ser Lys Lys Met Gly Phe Ser Tyr Ala Pro Met Pro Thr
305                 310                 315                 320

Pro Trp

<210> SEQ ID NO 58
<211> LENGTH: 330
<212> TYPE: PRT
<213> ORGANISM: Lycopersicon esculentum

<400> SEQUENCE: 58

Gly Pro Leu Val Pro Tyr Ser Cys Cys Pro Pro Met Pro Thr Asn
1               5                   10                  15

Phe Asp Thr Ile Pro Tyr Tyr Lys Phe Pro Ser Met Thr Lys Leu Arg
                20                  25                  30

Ile Arg Thr Pro Ala His Ala Val Asp Glu Glu Tyr Ile Ala Lys Tyr
            35                  40                  45

Asn Leu Ala Ile Ser Arg Met Arg Asp Leu Asp Lys Thr Glu Pro Leu
50                  55                  60

Asn Pro Leu Gly Phe Lys Gln Gln Ala Asn Ile His Cys Ala Tyr Cys
65                  70                  75                  80

Asn Gly Ala Tyr Ile Ile Gly Gly Lys Glu Leu Gln Val His Asn Ser
                85                  90                  95

Trp Leu Phe Phe Pro Phe His Arg Trp Tyr Leu Tyr Phe Tyr Glu Arg
                100                 105                 110

Ile Leu Gly Lys Leu Ile Asp Asp Pro Thr Phe Ala Leu Pro Tyr Trp
            115                 120                 125

Asn Trp Asp His Pro Lys Gly Met Arg Leu Pro Pro Met Phe Asp Arg
130                 135                 140

Glu Gly Ser Ser Leu Tyr Asp Glu Arg Arg Asn Gln Gln Val Arg Asn
145                 150                 155                 160

Gly Thr Val Leu Asp Leu Gly Ser Phe Gly Asp Lys Val Glu Thr Thr
                165                 170                 175

Gln Leu Gln Leu Met Ser Asn Asn Leu Thr Leu Met Tyr Arg Gln Met
            180                 185                 190

Val Thr Asn Ala Pro Cys Pro Leu Leu Phe Phe Gly Ala Pro Tyr Val
        195                 200                 205

Leu Gly Asn Asn Val Glu Ala Pro Gly Thr Ile Glu Thr Ile Pro His
    210                 215                 220

Ile Pro Val His Ile Trp Ala Gly Thr Val Arg Gly Ser Lys Phe Pro
225                 230                 235                 240

Asn Gly Asp Val Ser Tyr Gly Glu Asp Met Gly Asn Phe Tyr Ser Ala
```

```
              245                 250                 255
Gly Leu Asp Pro Val Phe Tyr Cys His His Gly Asn Val Asp Arg Met
            260                 265                 270
Trp Asn Glu Trp Lys Ala Ile Gly Gly Lys Arg Arg Asp Ile Ser Glu
        275                 280                 285
Lys Asp Trp Leu Asn Ser Glu Phe Phe Tyr Asp Glu His Lys Asn
    290                 295                 300
Pro Tyr Arg Val Lys Val Arg Asp Cys Leu Asp Thr Lys Lys Met Gly
305                 310                 315                 320
Tyr Asp Tyr Ala Pro Met Pro Thr Pro Trp
                325                 330
```

<210> SEQ ID NO 59
<211> LENGTH: 336
<212> TYPE: PRT
<213> ORGANISM: Spinacia oleracea

<400> SEQUENCE: 59

```
Gly Ser Val Gly Asp His Cys Cys Pro Pro Phe Asp Leu Asn Ile
1               5                   10                  15
Thr Lys Asp Phe Glu Phe Lys Asn Tyr His Asn His Val Lys Lys Val
            20                  25                  30
Arg Arg Pro Ala His Lys Ala Tyr Glu Asp Gln Glu Trp Leu Asn Asp
        35                  40                  45
Tyr Lys Arg Ala Ile Ala Ile Met Lys Ser Leu Pro Met Ser Asp Pro
    50                  55                  60
Arg Ser His Met Gln Gln Ala Arg Val His Cys Ala Tyr Cys Asp Gly
65                  70                  75                  80
Ser Tyr Pro Val Leu Gly His Asn Asp Thr Arg Leu Glu Val His Ala
                85                  90                  95
Ser Trp Leu Phe Pro Ser Phe His Arg Trp Tyr Leu Tyr Phe Tyr Glu
            100                 105                 110
Arg Ile Leu Gly Lys Leu Ile Asn Lys Pro Asp Phe Ala Leu Pro Tyr
        115                 120                 125
Trp Asn Trp Asp His Arg Asp Gly Met Arg Ile Pro Glu Ile Phe Lys
    130                 135                 140
Glu Met Asp Ser Pro Leu Phe Asp Pro Asn Arg Asn Thr Asn His Leu
145                 150                 155                 160
Asp Lys Met Met Asn Leu Ser Phe Val Ser Asp Glu Glu Gly Ser Asp
                165                 170                 175
Val Asn Glu Asp Asp Gln Tyr Glu Glu Asn Ile Leu Leu Met Arg Lys
            180                 185                 190
Ala Met Val Tyr Pro Ser Val Ser Asp Asp Pro Asn Lys Ala Glu Leu
        195                 200                 205
Phe Leu Gly Ser Pro Tyr Arg Ala Gly Asp Lys Met Glu Gly Asp Val
    210                 215                 220
Ser Gly Ala Gly Ile Leu Glu Arg Met Pro His Asn Ser Val His Val
225                 230                 235                 240
Trp Thr Arg Ser Asn Thr Ile Lys Gly Asn Gln Asp Met Gly Ala Phe
                245                 250                 255
Trp Ser Ala Gly Arg Asp Pro Leu Phe Tyr Cys His His Ser Asn Val
            260                 265                 270
Asp Arg Met Trp Ser Leu Trp Thr Asp Val Leu His Gly Gly Asn Phe
        275                 280                 285
```

```
Pro Lys Thr Pro Glu Tyr Asp Tyr Arg Asn Ala Tyr Phe Tyr Phe
    290                 295                 300

Tyr Asp Glu Asn Ala Asn Pro Val Arg Val Tyr Val Arg Asp Ser Phe
305                 310                 315                 320

Asp Thr Glu Arg Leu Gly Tyr Lys Tyr Glu Asp Gln Glu Leu Pro Trp
                325                 330                 335

<210> SEQ ID NO 60
<211> LENGTH: 321
<212> TYPE: PRT
<213> ORGANISM: Juglans regia

<400> SEQUENCE: 60

Pro Ala Gly Ala Leu Pro Val Asn Cys Cys Pro Pro Thr Ser Lys Lys
1               5                   10                  15

Ile Lys Asp Phe Val Leu Pro Ser Gln Asn Thr Pro Leu Arg Val Arg
                20                  25                  30

Pro Ala Ala His Leu Val Asp Asn Asp Tyr Ile Ala Lys Tyr Asn Lys
            35                  40                  45

Gly Ile Glu Leu Met Lys Ser Leu Pro Ala Asp Asp Pro Arg Ser Phe
50                  55                  60

Thr Gln Gln Ala Asn Val His Cys Ala Tyr Cys Asp Gly Ala Tyr Thr
65                  70                  75                  80

Gln Val Gly Phe Pro Asp Leu Ser Leu Gln Val His Glu Cys Trp Leu
                85                  90                  95

Phe Phe Pro Phe His Arg Tyr Tyr Val Tyr Phe Phe Glu Lys Ile Leu
            100                 105                 110

Gly Lys Leu Ile Gly Asp Pro Thr Phe Ala Leu Pro Phe Trp Asn Trp
        115                 120                 125

Asp Ser Pro Pro Gly Met Gln Leu Pro Ser Leu Tyr Ala Val Ser Asn
130                 135                 140

Ser Ala Ile Tyr Asp Pro Leu Arg Asn Ala Asn His Gln Pro Pro Thr
145                 150                 155                 160

Ile Ile Asp Leu Asp Tyr Gly Glu Thr Ser Glu Ser Thr Thr Thr Thr
                165                 170                 175

Asp Gln Val Pro Ser Asn Leu Lys Ile Met Tyr Arg Gln Met Val Ser
            180                 185                 190

Gly Ala Lys Asn Pro Thr Leu Phe Phe Gly Ser Pro Tyr Arg Ala Gly
        195                 200                 205

Asp Glu Pro Asp Pro Gly Ala Gly Thr Ile Glu Ser Thr Pro His Asn
210                 215                 220

Asn Ile His Leu Trp Thr Gly Asp Asp Thr Gln Pro Asn Ile Glu Asn
225                 230                 235                 240

Met Gly Asn Phe Tyr Ser Ala Gly Arg Asp Pro Ile Phe Phe Ala His
                245                 250                 255

His Ser Asn Val Asp Arg Met Trp Thr Ile Trp Lys Thr Leu Gly Gly
            260                 265                 270

Lys Arg Lys Asp Ile Thr Asp Pro Asp Trp Leu Asn Ser Ser Phe Phe
        275                 280                 285

Phe Tyr Asp Glu Asn Ala Asp Pro Val Arg Val Lys Val Lys Asp Cys
290                 295                 300

Val Asp Asn Thr Lys Leu Arg Tyr Val Tyr Gln Asp Val Glu Ile Pro
305                 310                 315                 320

Trp
```

```
<210> SEQ ID NO 61
<211> LENGTH: 44
<212> TYPE: DNA
<213> ORGANISM: Artificial Sequence
<220> FEATURE:
<223> OTHER INFORMATION: primer

<400> SEQUENCE: 61
cacytacagr ccmamwtggg aagrggycar tatgmwggtg atga                    44

<210> SEQ ID NO 62
<211> LENGTH: 26
<212> TYPE: DNA
<213> ORGANISM: Artificial Sequence
<220> FEATURE:
<223> OTHER INFORMATION: primer

<400> SEQUENCE: 62
gtyatggghg ararrggttt ratgtc                                        26

<210> SEQ ID NO 63
<211> LENGTH: 32
<212> TYPE: DNA
<213> ORGANISM: Artificial Sequence
<220> FEATURE:
<223> OTHER INFORMATION: primer

<400> SEQUENCE: 63
taagcaakwg ccttgccwgc kccaccagca cc                                 32

<210> SEQ ID NO 64
<211> LENGTH: 38
<212> TYPE: DNA
<213> ORGANISM: Artificial Sequence
<220> FEATURE:
<223> OTHER INFORMATION: primer

<400> SEQUENCE: 64
gcmcccttyt cytttgcmcc rtaagcaakw gccttgcc                           38

<210> SEQ ID NO 65
<211> LENGTH: 30
<212> TYPE: DNA
<213> ORGANISM: Artificial Sequence
<220> FEATURE:
<223> OTHER INFORMATION: primer

<400> SEQUENCE: 65
gcactcgaga tggcttctac actctctacc                                    30

<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66
gcaggatcca accttgtatg tggccattgc                                    30
```

PLANTS WITH ELEVATED LEVELS OF GALLIC ACID/POLYPHENOL OXIDASE AND METHODS OF GENERATING SUCH PLANTS

RELATED APPLICATION

This application is a Continuation-in-part of PCT Application No. PCT/US2004/043738, filed Dec. 22, 2004, which claims the benefit under 35 U.S.C. 119(e) to U.S. Application No. 60/534,424 filed Jan. 5, 2004, both of which are hereby incorporated by reference herein in their entirety.

GOVERNMENT RIGHTS

This invention was made with Government support under Grants (or Contracts) 58-5325-8-111, awarded by the United States Department of Agriculture, and T32-GM08799-01A1, NIGMS, awarded by Training Program in Biomolecular Technology. The Government may have certain rights in this invention.

FIELD OF THE INVENTION

This invention is in the field of pest resistance and protein utilization. Specifically the invention relates to organisms including plants that have elevated levels of gallic acid and are thereby able to suppress aflatoxin production by *Aspergillus flavus*. The elevated levels of gallic acid lead to an increase in hydrolysable tannin accumulation and an increase in condensed tannins that contain gallic acid residues; these features provide resistance to pests and pathogens. Also, increased protein utilization occurs in organisms including plants that have elevated levels of a gallic acid-based metabolite (Gallic Acid based hydrolysable tannin-GAHT, Gallic acid containing condensed tannin-GACT) or an enzyme (polyphenol oxidase-PPO). The invention also relates to methods of making such organisms.

BACKGROUND OF THE INVENTION

Mycotoxins are noxious compounds produced by a variety of fungal species. One such mycotoxin, aflatoxin, has been linked to contaminated food (e.g., corn, rice, peanuts, and tree nuts) and animal feed (Woloshuck 1998, Smela 2001). Aflatoxins are produced by specific strains of the filamentous fungus *Aspergillus* (aflatoxin=*Aspergillus flavus* toxin) and encompass a group of structurally related compounds (Trail 1995). One member in particular, aflatoxin B1 (AFB1), is the most toxic and the most prevalent in nature (Woloshuck 1998). Up to twenty five percent of the global food supply is contaminated, annually, by AFB1 (Trail 1995, Moreno 1999). In the United States, the Food and Drug Administration (FDA) regulates the levels of aflatoxin in foods such that crops with more than 20 parts per billion (ppb) total aflatoxins cannot be imported/exported and sold (Gourama 1995, Trail 1995).

Aflatoxins induce specific point mutations in DNA. Typically, aflatoxins like AFB1 are metabolized in the liver. There they are converted into epoxides (AFB-8,9-epoxide) which subsequently become covalently linked to guanine bases in the liver cell DNA (Eaton 1994, Wang 2000, Smela 2001). Addition of the epoxide (usually at the N7 position) stimulates depurination of the guanine base which is then misinterpreted during subsequent DNA replication (Smela 2001). Thus, aflatoxin induces GC→TA transversions within the DNA. One such point mutation has been shown to readily form within the liver p53 tumor suppressor gene (G249T) and in fact, this particular transversion has been directly correlated with the occurrence of hepatocellular carcinoma (i.e., liver cancer) (Hussain 1994, Moreno 1999, Tiemersma 2001).

In recent years, strategies have been proposed to eliminate aflatoxins from food and feed. In the field, application of fungicide has prevented fungal infection and subsequently, mycotoxin contamination. Aflatoxin detection via chromatography and UV luminescence coupled with post-harvest removal techniques have also been utilized (Kathuria 1993). These current elimination strategies, however, have been costly, ineffective, and/or environmentally unsound (Trail 1995, Campbell 2003). Thus, there is a need for simpler, less expensive ways of limiting or preventing aflatoxin contamination of food and feed.

Alfalfa (*Medicago sativa*) is the most widely grown forage in the western United States, providing over $2 billion of cash income to its producers. Alfalfa constitutes about 23 to 34% of dairy ration on dry matter basis (Getachew et al. 2005). However, alfalfa protein and nitrogen (N) utilization by ruminants is generally considered to be sub-optimum. Over 50% of the N contained in alfalfa forage is utilized poorly, or not at all, for animal products (e.g., milk, meat, fiber). The result is excretion of excess N, one of the most significant non-source groundwater and air contamination sources. Because of poor N utilization, high producing dairy cows require costly protein concentrate supplements. Protein concentrate production itself is water and energy intensive. Improving protein utilization and feeding value of alfalfa must be considered as the single highest impact intervention for environmental compatibility and sustainability of dairy production. Excess N from high producing dairy cows is one of the most critical environmental problems—not only in California, but in all dairy regions of the world. There is, thus, a need for plants with improved protein utilization characteristics.

SUMMARY OF THE INVENTION

The present invention meets these needs by providing non-naturally occurring plants that contain elevated levels of gallic acid, which inhibits aflatoxin production by *A. flavus*, and is a key intermediate and rate limiting step in the synthesis of hydrolysable tannins that contain gallic acid residues. Also provided are non-naturally occurring plants that contain elevated levels of polyphenol oxidase (PPO). The present invention also provides methods of generating such non-naturally occurring plants.

Non-naturally occurring plants containing elevated levels of gallic acid or PPO are described herein. In a preferred aspect, the non-naturally occurring plant is a transgenic plant. Preferred embodiments include plants in which the elevated level is at least 20%, at least 40%, at least 60%, at least 80%, at least 100%, at least 150%, at least 200%, at least 250%, at least 300%, at least 400%, or at least 500% higher than in the comparable naturally occurring plant. In certain embodiments, the elevated levels may be localized to specific tissues. In preferred embodiments, the elevated levels are localized to the floral/reproductive tissues, including, but not limited to, the testa, the seed hairs, the hull epidermis, the hull cortex, the shell, the pellicle, the husk, the seed coat, the kernel, the embryo, the pod, the peg, the seed, and the seed coat, as appropriate for the plant of interest. In yet another variation, the tissue of the non-naturally occurring plant contains at least 4%, at least 4.5%, at least 5%, at least 5.5%, at least 6%, at least 7%, at least 8%, at least 10%, or at least 12% by weight gallic acid.

A preferred embodiment of the non-naturally occurring plants of the present invention is a plant transgenically expressing an enzyme or enzymes capable of synthesizing elevated levels of gallic acid. Another embodiment of the non-naturally occurring plants of the present invention is a plant transgenically expressing PPO. In one variation, the transgenic plant includes one or more genes that provide gallic acid synthesis activity. A preferred example is a transgenic plant comprising a shikimate dehydrogenase gene that has gallic acid biosynthesis activity. The shikimate dehydrogenase gene may be operably connected to a transit peptide. Such shikimate dehydrogenase genes may include any of the constructs detailed below. Preferred plants are walnut, cotton, peanut, rice, alfalfa, soybean, wheat and corn.

The present invention is further directed to the finding that the shikimate dehydrogenase protein catalyzes the conversion of 3-dehydroshikimate-enol form to gallic acid and therefore may be used in a preferred embodiment of the non-naturally occurring plants of the present invention. The present invention also encompasses the finding that PPO is a key enzyme in the synthesis of polyphenolic compounds such as melanin. Its role in the oxidation of a wide range of phenolic substrates is well known to food scientists.

The shikimate dehydrogenase and PPO protein-encoding nucleic acid sequences as defined herein refer to 1) any sequence that hybridizes to nucleic acid molecules of SEQ ID NO: 1; and 2) any sequence that hybridizes to SEQ ID NO: 9, respectively. The shikimate dehydrogenase and PPO protein-encoding nucleic acid sequences are further defined as complements thereof under at least low stringency, preferably moderate, high or very high stringency conditions, or are about 85%, 90%, 95%, or 97% identical to SEQ ID NO: 1 and SEQ ID NO: 9, respectively, or encode polypeptide sequences having at least about 85%, 90%, 95%, or 97% sequence identity to the amino acid sequence of SEQ ID NO: 2 (shikimate dehydrogenase), and SEQ ID NO: 10 (PPO), respectively. This invention is directed to the shikimate dehydrogenase and PPO protein-encoding nucleic acid sequences as described above. The invention is further directed to oligonucleotide primers that bind the nucleic acid sequences of SEQ ID NO: 1 and SEQ ID NO: 9.

The present invention is further directed to the finding that gallic acid is a key intermediate and rate limiting step in the synthesis of hydrolysable tannins that contain GA residues (GAHTs/HTs). HTs precipitate proteins by forming complexes and have traditionally been used for tanning leather. Condensed tannins also precipitate proteins and, although are not used for leather tanning, have been shown to improve protein utilization. Some condensed tannins can contain GA residues (GACTs) and many of these have antiparasidal activity.

The present invention is further directed to the finding that PPO enzymes in many plants recognize the ubiquitous substrate tyrosine, oxidizing it to create highly reactive quinones and the polymer melanin. Quinones and melanin can react with or sequester endogenous proteins due to interaction of hydrophobic amino acid groups in proteins, and quinones.

The invention is further directed to recombinant constructs containing such isolated nucleic acids. The recombinant constructs may further include a promoter. The promoter may be a homologous or a heterologous promoter. The recombinant constructs may further be in a vector. For example, the vector may be a cloning, expression, transformation, or transfection vector.

The invention is further directed to isolated nucleic acids encoding the protein depicted in SEQ ID NO: 2 and homologs of the protein. Yet another aspect of the present invention includes proteins catalyzing the synthesis of gallic acid and nucleic acids encoding such proteins. The gallic acid synthetic proteins are proteins with structural homology to shikimate dehydrogenase proteins that have the gallic acid synthetic activity. Nucleic acids encoding gallic acid synthetic proteins may be in a vector or transgenically expressed in plants. Such nucleic acids are preferably operably linked to a promoter that may be an inducible promoter, a regulated promoter, a tissue-specific promoter, or a constitutive promoter. Preferred tissue-specific promoters are those that are specific to the floral/reproductive tissues, including, but not limited to, the testa, the seed hairs, the hull epidermis, the hull cortex, the shell, the pellicle, the husk, the kernel, the embryo, the pod, the peg, the seed, and the seed coat, as appropriate for the plant of interest. The gallic acid synthesis protein-coding sequences of the invention include those sequences that hybridize under at least low stringency and preferably moderate, high, or very high stringency conditions to the nucleic acid of SEQ ID NO: 1 or its complement. The gallic acid synthesis proteins may be one or more proteins that catalyze multiple enzymatic steps in order to synthesize gallic acid. In another embodiment of the presenting invention, the gallic acid synthesis protein-coding sequences also include those sequences with at least 85% sequence identity and preferably at least 90%, or at least 95% sequence identity with a nucleotide sequence of SEQ ID NO: 1. The present invention also includes isolated proteins having the protein sequence of SEQ ID NO: 2 as well as protein sequences with at least 85% sequence identity and preferably at least 90%, or at least 95% sequence identity with the protein sequence of SEQ ID NO: 2. The present invention further includes nucleic acid sequences encoding the above protein sequences.

In yet another aspect of the present invention, the nucleic acids of the present invention are expressed as anti-sense RNA, sense suppression RNA or RNAi in constructs as described above. Such constructs may be used to lower or inhibit the expression of the endogenous forms of the nucleic acids in any of the host cells described below.

Yet another aspect of the present invention is a host cell containing any of the above nucleic acids, vectors, or constructs. Such nucleic acids, vectors and construct may be introduced into a prokaryotic or eukaryotic host cell. Preferred host cells include bacterial cells such as E. coli, yeast cells, and plant cells. The nucleic acids, vectors and constructs may be introduced into the host cells so that the expression of the nucleic acid may be controlled or regulated. The introduction of the construct into the host cell may be transient or stable. The control or regulation may include tissue-specific promoters designed to express the isolated nucleic acids in given tissues such as the pellicle. Such regulation may be directed to constitutive expression. The regulation may be responsive to various biotic, abiotic and artificial stimuli, relative to the native PPO or shikimate dehydrogenase promoter.

The invention is also directed to antibodies and ligands that bind a polypeptide having at least about 85%, 90%, 95%, or 97% sequence identity to the amino acid sequence of SEQ ID NO: 2, and to the amino acid sequences of SEQ ID NO: 10.

The present invention is additionally directed to use of gallic acid to inhibit synthesis of aflatoxin. Gallic acid may be applied externally to plants and plant parts or to the surrounding soil to inhibit aflatoxin production. Gallic acid may be applied by itself or in combination with other compounds such as pesticides, herbicides, and fertilizers. Gallic acid may be applied to plants in crops or to plants or plant parts after harvest, including fruits, vegetables, grains, nuts, berries, and leaves. Such gallic acid applied externally may be washed off such plants or plant parts prior to distribution. Alternatively, gallic acid applied externally may be left on the plants or plant parts since it is also found naturally in certain plants.

An additional aspect of the present invention includes growing or cultivating the above host cells and/or plants and isolating or otherwise extracting the gallic acid produced. In addition, the non-naturally occurring plants with elevated levels of gallic acid and host cells expressing shikimate dehydrogenase of the present invention may have elevated levels of ellagic acid. Therefore, the present invention includes non-naturally occurring plants with elevated levels of ellagic acid and host cells producing ellagic acid in all the permutations described above. The elevated levels of GA could lead to the elevated levels of different hydrolysable tannins (HTs). In addition to HTs the presence of additional GA could stimulate the synthesis of GA containing condensed tannins (GACTs). These could provide plants with additional unique properties most notably resistance to parasites (insect and nematode). Additionally the synthesis of GA could shift the pathway more in the direction of synthesis of HTs as pointed out above, which could result in less carbon flow through the phenolproponoid pathways, thus reducing lignin biosynthesis. Controlling lignin biosynthesis is not only important for feed but also for the bioconversion of biofuels like ethanol, making that process more efficient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows a depiction of a structure of gallic acid. 1B shows a cross-section of a walnut. 1C shows the synthetic pathway in Tulare for gallic acid.

FIG. 2A shows rhodanine staining of gallic acid and various compounds structurally related to gallic acid. 2B shows the relative concentration of gallic acid in the pellicle of Tulare over time.

FIG. 3A shows the level of gallic acid produced in the gel slices from a non-denaturing protein gel. The squares indicate the level of gallic acid produced when the protein is denatured. The triangles indicate the level of gallic acid produced in the non-denatured gel with shikimic acid added. The diamonds indicate the level of gallic acid produced in the non-denatured gel without addition of shikimic acid. 3B shows the non-denaturing protein gel with MTT/PMS staining indicating shikimate dehydrogenase activity.

FIGS. 4A-4C shows the sequence alignment of shikimate dehydrogenase from *J. regia* cv. Tulare (SEQ ID NO:2) compared to shikimate dehydrogenase from *L. esculentum* (SEQ ID NO:3), *N. tabacum* (SEQ ID NO:4), *O. sativa* (SEQ ID NO:5), *A. thaliana* (SEQ ID NO: 6), and *P. sativum* (SEQ ID NO: 7). The majority consensus sequence (SEQ ID NO: 8) of the six sequences is located above the sequences and denoted as "Majority".

FIG. 6 shows SEQ ID NO: 1; the protein-encoding nucleotide sequence of shikimate dehydrogenase from *J. regia* cv. Tulare.

FIG. 7 shows SEQ ID NO: 2; the amino acid sequence of shikimate dehydrogenase from *J. regia* cv. Tulare.

FIG. 10A shows Shikimate dehydrogenase activity measured from the following samples: a) CR-1 non-transformed control, b) Y2H1, c) Y2G7, d) Y2H5, e) Y2G5, f) G2D12, g) G2F8, h) G2F1 and i) G2G2. 10B shows the percentage increase in gallic acid content from the transformed lines relative to the negative, non-transformed CR-1 control.

FIG. 16 shows a multiple sequence alignment of the AroD, dehydroquinase I domain. The *J. regia* sequence, amino acids 57 to 274 (SEQ ID NO: 16), is highlighted with yellow background. 100% conserved residues are highlighted (identical and chemically similar amino acids, black and gray vertical columns, respectively). Active site residues shown in FIG. 15, in 3D structures of proteins from *S. aureus* and *S. typhi*, are highlighted in light blue (the two sequences identified as AroD_STAAR (SEQ ID NO: 18) and AroD_SALTI (SEQ ID NO: 12) in FIG. 16). Corresponding residues in the *J. regia* sequence (SEQ ID NO: 16) are highlighted in orange and red: the lysine residue directly involved in catalysis (Chaudhuri et al. 1991). The latter is 100% conserved, and indicated by violet highlights. Highlighted likewise is a conserved active site, histidine, not shown in FIG. 2 (Deka et al. 1992). SEQ ID NOS: 11-21 are shown in FIG. 16.

FIG. 23 shows SEQ ID NO: 9; the protein-encoding nucleotide sequence of polyphenol oxidase (PPO) from walnut.

FIG. 24 shows SEQ ID NO: 10; the amino acid sequence of polyphenol oxidase (PPO) from walnut.

BRIEF DESCRIPTION OF THE SEQUENCE LISTING

Figure 5:
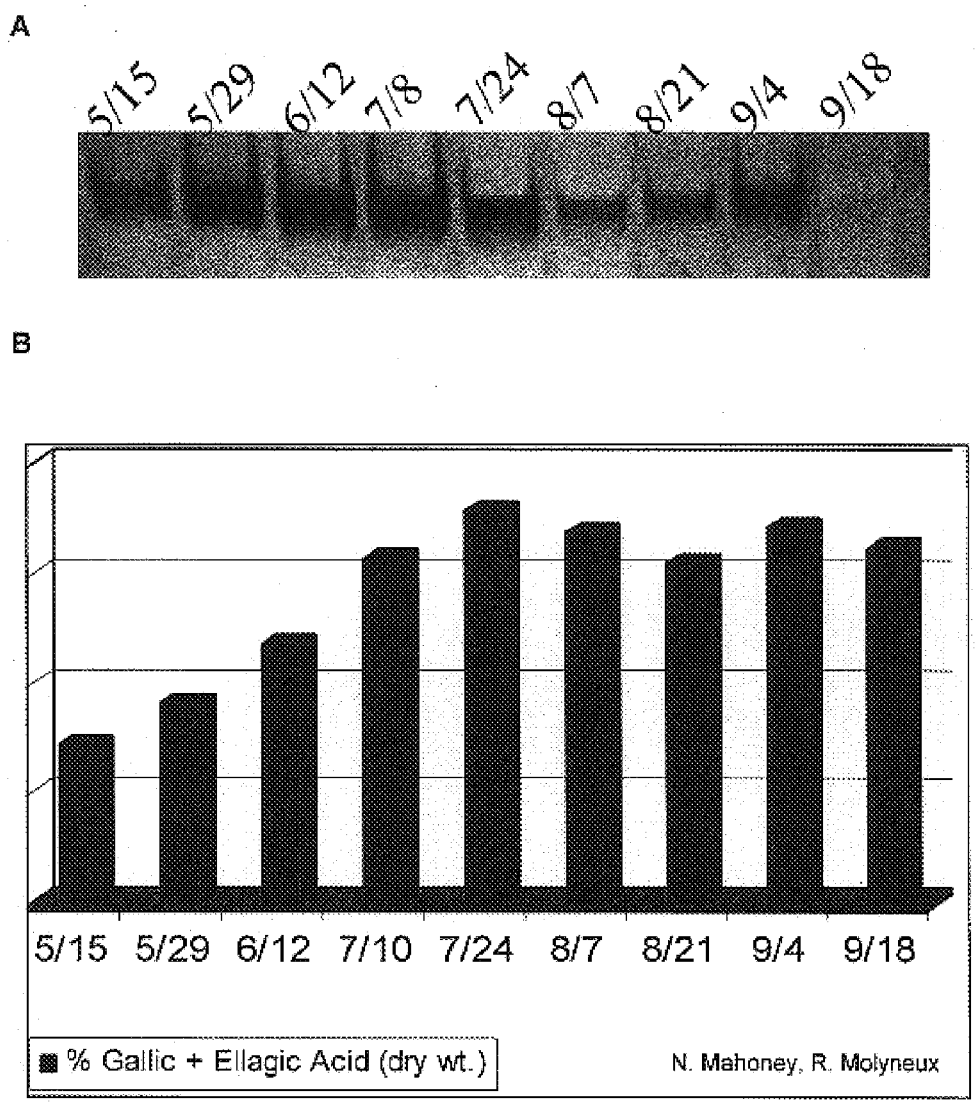
FIG. 5A shows a non-denaturing protein gel supplemented with shikimic acid and stained with MTT/PMS to show levels of shikimate dehydrogenase activity in Tulare pellicle at various time points in the growth cycle of the plant. 5B shows the levels of gallic and ellagic acid isolated from Tulare pellicle at the same time points.

The following sequences are grouped according to the nature of the sequence. The list does not include sequences used as PCR primers or sequences used in sequence comparisons.

SEQ ID NO: 1 is the protein-encoding nucleotide sequence of shikimate dehydrogenase from *J. regia* cv. Tulare.

SEQ ID NO: 2 is the amino acid sequence of shikimate dehydrogenase from *J. regia* cv. Tulare.

SEQ ID NO: 3 is the amino acid sequence of shikimate dehydrogenase from *L. esculentum*.

SEQ ID NO: 4 is the amino acid sequence of shikimate dehydrogenase from *N. tabacum*.

SEQ ID NO: 5 is the amino acid sequence of shikimate dehydrogenase from *O. sativa*.

SEQ ID NO: 6 is the amino acid sequence of shikimate dehydrogenase from *A. thaliana*.

SEQ ID NO: 7 is the amino acid sequence of shikimate dehydrogenase from *P. sativum*.

SEQ ID NO: 8 is the amino acid sequence representing the majority consensus of the amino acid sequences of shikimate dehydrogenase from *J. regia* cv. Tulare, *L. esculentum, N. tabacum, O. sativa, A. thaliana*, and *P. sativum*.

SEQ ID NO: 9 is the protein-encoding nucleotide sequence of polyphenol oxidase from walnut.

SEQ ID NO: 10 is the amino acid sequence of polyphenol oxidase from walnut.

SEQ ID NO: 11 is the amino acid sequence of AroD, dehydroquinase I domain from *E. coli*.

SEQ ID NO: 12 is the amino acid sequence of AroD, dehydroquinase I domain from *S. typhi*.

SEQ ID NO: 13 is the amino acid sequence of AroD, dehydroquinase I domain from *N. tabacum*.

SEQ ID NO: 14 is the amino acid sequence of AroD, dehydroquinase I domain from *L. esculentum*.

SEQ ID NO: 15 is the amino acid sequence of AroD, dehydroquinase I domain from *A. thaliana*.

SEQ ID NO: 16 is the amino acid sequence of AroD, dehydroquinase I domain from *J. regia*.

SEQ ID NO: 17 is the amino acid sequence of AroD, dehydroquinase I domain from *M. jannaschii*.

SEQ ID NO: 18 is the amino acid sequence of AroD, dehydroquinase I domain from *S. aureus*.

SEQ ID NO: 19 is the amino acid sequence of AroD, dehydroquinase I domain from *S. cerevisiae*.

SEQ ID NO: 20 is the amino acid sequence of AroD, dehydroquinase I domain from *C. trachomatis*.

SEQ ID NO: 21 is the amino acid sequence of AroD, dehydroquinase I domain from *N. crassa*.

SEQ ID NO: 22 is the amino acid sequence of AroE, shikimate DH domain of *S. pneumoniae*.

SEQ ID NO: 23 is the amino acid sequence of quinate/shikimate dehydrogenase of *E. coli*.

SEQ ID NO: 24 is the amino acid sequence of AroE, shikimate DH domain of *J. regia*.

SEQ ID NO: 25 is the amino acid sequence of AroE, shikimate DH domain of *L. esculentum*.

SEQ ID NO: 26 is the amino acid sequence of AroE, shikimate DH domain of *A. thaliana*.

SEQ ID NO: 27 is the amino acid sequence of AroE, shikimate DH domain of *T. maritima*.

SEQ ID NO: 28 is the amino acid sequence of AroE, shikimate DH domain of *S. aureus*.

SEQ ID NO: 29 is the amino acid sequence of AroE, shikimate DH domain of *A. aeolicus*.

SEQ ID NO: 30 is the amino acid sequence of AroE, shikimate DH domain of *M. jannaschii*.

SEQ ID NO: 31 is the amino acid sequence of AroE, shikimate DH domain of *B. subtilis*.

SEQ ID NO: 32 is the amino acid sequence of AroE, shikimate DH domain of *E. coli*.

SEQ ID NO: 33 is the amino acid sequence of AroE, shikimate DH domain of *P. aeruginosa*.

SEQ ID NO: 34 is the amino acid sequence of AroE, shikimate DH domain of *H. influenzae*.

SEQ ID NO: 35 is the amino acid sequence of AroE, shikimate DH domain of *N. tabacum*.

SEQ ID NO: 36 is the amino acid sequence of AroE, shikimate DH domain of *L. esculentum*.

SEQ ID NO: 37 is the amino acid sequence of AroE, shikimate DH domain of *A. thaliana*.

SEQ ID NO: 38 is the amino acid sequence of AroE, shikimate DH domain of *J. regia*.

SEQ ID NO: 39 is the amino acid sequence of AroE, shikimate DH domain of *T. maritima*.

SEQ ID NO: 40 is the amino acid sequence of AroE, shikimate DH domain of *S. aureus*.

SEQ ID NO: 41 is the amino acid sequence of AroE, shikimate DH domain of *A. aeolicus*.

SEQ ID NO: 42 is the amino acid sequence of AroE, shikimate DH domain of *M. jannaschii*.

SEQ ID NO: 43 is the amino acid sequence of AroE, shikimate DH domain of *B. subtilis*.

SEQ ID NO: 44 is the amino acid sequence of AroE, shikimate DH domain of *E. coli*.

SEQ ID NO: 45 is the amino acid sequence of AroE, shikimate DH domain of *H. influenzae*.

SEQ ID NO: 46 is the amino acid sequence of polyphehol oxidase from *R. nigromaculata*.

SEQ ID NO: 47 is the amino acid sequence of polyphehol oxidase from *H. sapiens*.

SEQ ID NO: 48 is the amino acid sequence of polyphehol oxidase from *N. crassa*.

SEQ ID NO: 49 is the amino acid sequence of polyphehol oxidase from *O. dofleini*.

SEQ ID NO: 50 is the amino acid sequence of polyphehol oxidase from *O. dofleini*.

SEQ ID NO: 51 is the amino acid sequence of polyphehol oxidase from *O. dofleini*.

SEQ ID NO: 52 is the amino acid sequence of polyphehol oxidase from *R. thomasiana*.

SEQ ID NO: 53 is the amino acid sequence of polyphehol oxidase from *V. faba*.

SEQ ID NO: 54 is the amino acid sequence of polyphehol oxidase from *M. domestica*.

SEQ ID NO: 55 is the amino acid sequence of polyphehol oxidase from *I. batatas*.

SEQ ID NO: 56 is the amino acid sequence of polyphehol oxidase from *L. esculentum*.

SEQ ID NO: 57 is the amino acid sequence of polyphehol oxidase from *S. tuberosum*.

SEQ ID NO: 58 is the amino acid sequence of polyphehol oxidase from *L. esculentum*.

SEQ ID NO: 59 is the amino acid sequence of polyphehol oxidase from *S. oleracea*.

SEQ ID NO: 60 is the amino acid sequence of polyphehol oxidase from *J. regia*.

DETAILED DESCRIPTION OF THE INVENTION

Gallic acid (3,4,5-trihydroxybenzoic acid; GA) is a fundamental precursor for many plant secondary metabolites, particularly the hydrolysable tannins (Gross, 1982; Haslam, 1998; Gross, 2000; Grundhoefer et al., 2001) and has several pharmaceutical and industrial applications (Draths K. M., 1999; Ossipov et al., 2003). Plants, *Escherichia coli* and fungi have been shown to accumulate high levels of gallic acid and within these organisms, galloyl moieities are often added as modifications to other compounds (Werner et al., 1997).

It has been successfully demonstrated that shikimate dehydrogenase (SDH, EC 1.1.1.25), a shikimate pathway enzyme, is responsible for the synthesis of gallic acid in plants (*Arabidopsis thaliana* and *Juglans regia*) and *E. coli* (Muir et al., submitted, see Appendix). Although SDH is a monomer, it is a component of the penta-functional AROM enzyme complex in fungi and occurs in a bi-functional enzyme coupled with a 3-dehydroquinate dehydratase (AroD) domain in plants (Bonner and Jensen, 1992; Padyana and Burley, 2003; Ye et al., 2003). As part of the shikimate pathway, SDH catalyzes the NADPH-dependent reduction of DHS to shikimic acid (Padyana and Burley, 2003; Vogan, 2003; Ye et al., 2003). It has been demonstrated via complementation in *E. coli* that there is an additional novel role for SKDH: an NADP+-dependent oxidation of DHS to gallic acid.

The present invention is directed to the observation as more fully described in the examples below that sufficiently high concentrations of gallic acid will inhibit the synthesis of aflatoxins by *A. flavus*. Gallic acid is also a key intermediate and rate limiting step in the synthesis of hydrolysable tannins that contain GA residues (GAHTs/HTs). Furthermore, the enzyme responsible for the synthesis of gallic acid in plants has been identified in Examples 2 and 3 as shikimate dehydrogenase. For example, shikimate dehydrogenase catalyzes the synthesis of gallic acid via the pathway outlined in FIG. 1C. Many plant components such as metabolites (tannins), enzymes (polyphenol oxidase, phytase, etc.) and fiber (cellulose, lignin) influence protein utilization and, thus, feeding value. HTs complex proteins and have traditionally been used for tanning leather. Condensed tannins also complex proteins and, although they are not used for leather tanning, have been shown to improve protein utilization. Thus, plants modified to over-express a metabolite (Gallic Acid based hydrolysable tannin-GAHT) or an enzyme (polyphenol oxidase-PPO) may show improved protein utilization.

It is to be understood that the invention is not limited in its application of the details of construction and the arrangements of the components set forth in the following description. The invention may include other embodiments or may be practiced or carried out in various ways. Also, it is to be understood that the phraseology and terminology employed herein is for the purpose of description and should not be regarded as limiting the scope of the invention.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995), Harlow and Lane, eds. (1988) ANTIBODIES, A LABORATORY MANUAL, and ANIMAL CELL CULTURE R.I. Freshney, ed. (1987).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y. Definitions of common terms in plant biology may be found in Esau, Plant Anatomy, published by John Wiley & Sons (1977) (ISBN 0-471-24520-8); and Solomon et al., Biology, published by Saunders College Publishing (1993).

Introduction

World-wide alfalfa production is estimated to cover over 32 million ha of which 70% is located in United States, followed by former the Soviet Union, and Argentina (Irwin et. al., 2001). In the United States, alfalfa represents about 2.5% of the total agricultural acreage with approximately half of the alfalfa acreage in the upper Midwest and Northern Great Plains (Riday & Brummer, 2002). The widespread use of this species is due to its high adaptability, forage yield potential, and its good forage quality characteristics compared to other forages (high intake and digestibility, high nitrogen and relatively low fiber content).

In California, alfalfa is the highest acreage crop and of critical importance to thousands of farmers and ranchers in the San Joaquin Valley, Intermountain and desert agricultural areas. In 2005, California's alfalfa crop was worth nearly $1 billion, and is the major feedstuff for the state's most important agricultural enterprise, dairy, worth over $4.5 billion per year. Improvement of the protein utilization and quality of alfalfa varieties has the potential to impact thousands of alfalfa growers, to provide opportunities for California alfalfa seed companies and growers, while improving the nutritional efficiency and dairy profitability of California's 1.7 million dairy cows. California is the leading dairy state in the nation, and currently produces 20% of the nation's milk. Projections by Land-o-Lakes Cooperative predict that California may produce 36% of the nation's milk in 2025 (Hahn, 2004). Feed costs constitute over 50% of the production costs of dairies, and efficiency of feed production is likely to have major effects on dairy profitability.

An average cow producing 8200 kg of milk annually excretes 21,000 kg of manure containing about 110 kg of N (van Horn et al., 1996), with approximately equal proportions excreted in feces and urine. The majority of urinary N (depending on diet and animal condition) is in the form of urea, which is hydrolyzed by fecal urease to $NH_3$. About 25% of dairy manure N is lost as $NH_3$ under current US practices (Pinder et al., 2004), contributing to the total annual $NH_3$ redeposition rates in the Upper Midwest of 23 to 40 kg of N/ha (Burkart and James, 1999). Results from various research and modeling approaches suggest that improving the efficiency of N utilization by dairy cows, which in most production schemes rarely exceeds 25 to 30%, is the most promising way to decrease N losses from dairy farms with minimal detrimental effects, if any, on their productivity and profitability (Kohn et al., 1997; Rotz et al., 1999). Reducing the output of N in urine provides the greatest opportunity for achieving that goal (Hvelplund and Madsen, 1996). This is because most of the N present in urine arises from inefficient N transactions in the rumen and tissues of cows that may be amenable to manipulation (Lobley, 2002).

Reducing protein degradation through incorporation of tannin expression in alfalfa may address the following concerns:

1. Protein requirement of high producing dairy cows can not be met from a sole microbial source.

2. Protein is often the most expensive ingredient of ruminant rations.

3. Excessive degradation of alfalfa protein leads to higher amount of nitrogenous compounds into the environment causing environmental pollution.

4. High urea-N was associated with extensive ruminal degradation of protein can cause reproductive problems in dairy cows (Elrod and Butler, 1993).

5. A rapid and extensive ruminal degradation of protein can cause bloat.

Importance of Tannins in Ruminant Nutrition

Research has shown that tannins in forage plants reduced protein degradation, increased microbial protein synthesis, and increased the efficiency of protein utilization (Getachew et al. 2000). Tannins play a significant role in ruminant nutrition by reducing excessive degradation of proteins and increasing high quality protein reaching the lower gut for enzymatic digestion. The reduction of ruminal degradability of protein also reduces excessive loss of nitrogen to the environment. By improving protein utilization, preventing occurrence of bloat, and reducing excessive loss of nitrogen to the environment, tannins contribute significantly to nutrient use efficiency and hence exert economical and environmental impact.

Chemical Properties and Structure of Tannins

Tannins are a structurally diverse class of naturally occurring, water soluble, polyphenolic compounds. All tannins have the ability to precipitate proteins, and it is this characteristic that distinguishes them from other polyphenolics (Haslam, 1994; 1998a). Tannins play an important role in plant secondary metabolism and are relatively ubiquitous among plants including the pteridophytes, gymnosperms and angiosperms (Bhat et al., 1998 and Frohlich et al., 2002). Because of the structural heterogeneity of these compounds, tannins have been classified into two major sub-groups; the flavonoid derived condensed tannins, or proanthocyanidins, and the more functionally active hydrolysable tannins (HTs). Both condensed and hydrolysable tannins are synthesized as part of the plants' phenylpropanoid metabolism. The condensed class is derived from the aromatic amino acid L-phenylalanine; HTs are synthesized from gallic acid. The biosynthesis of condensed tannins has been the subject of a great number of studies and a majority of the genes required for their formation have been reported. Only recently, however, has the synthesis, distribution, and prevalence of HTs been the subject of thorough examination.

Tannins are relatively large molecules with molecular weights between 500 and 4,000 Daltons (Da). They are composed of between 12-16 phenolic groups with 5-7 aromatic rings (Haslam, 1998b). Both condensed and hydrolysable tannins are present in monomeric, dimeric, or higher oligomeric forms. Oxidative coupling between two or more monomers give rise to structurally complex, insoluble molecules with molecular weights exceeding 20,000 Da.

Structure of Hydrolysable Tannins

Figure 11:
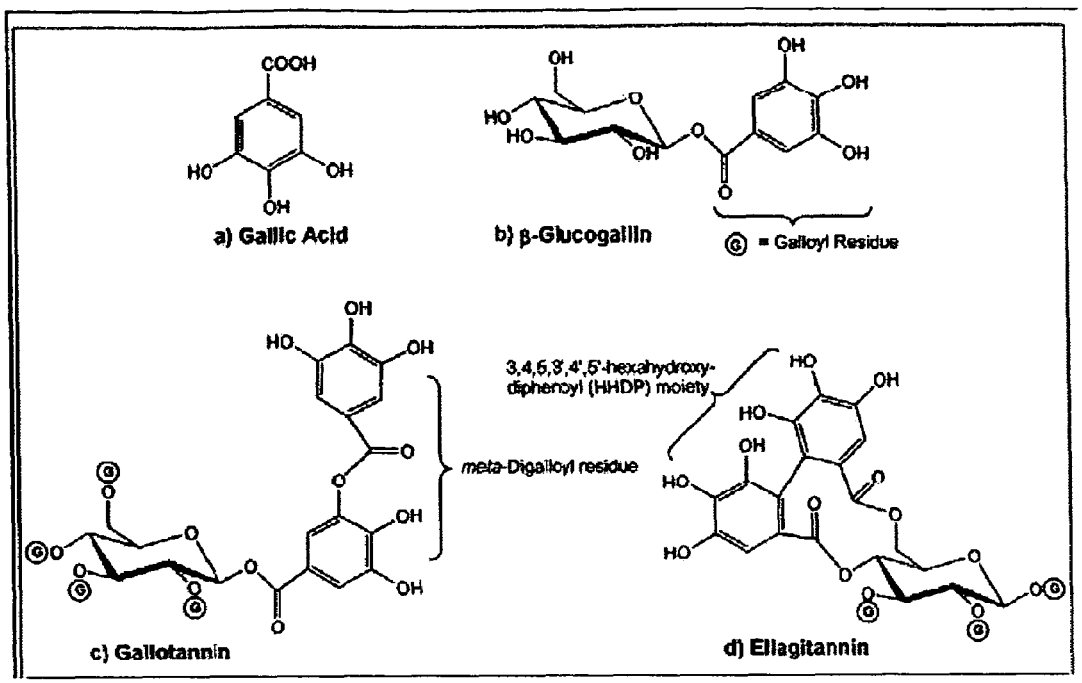
FIG. 11 shows the structures of hydrolysable tannins.

HTs have been classified into two distinct groups, the gallo- and ellagitannins, both of which have a central sugar core (i.e., D-glucose) with gallic acid residues. Each gallic acid contributes a single phenolic group to the molecule. Gallic acids can be joined to the sugar core through ester linkages (FIG. 11) (Haslam, 1998b; Gross, 2000; Grundhoefer et al., 2001). Gallotannins exhibit additional galloyl groups joined to one another through meta-despide linkages (Haslam, 1998b; Khanbabaee and van Ree, 2001; Niemetz and Gross, 1998). For ellagitannins, vicinal galloyl ester groups are coupled to yield to ellagic acid. Base or acid hydrolysis of HTs release free gallic and/or ellagic acid and glucose into solution (Chung et al., 1998).

Protein Precipitation

Figure 12:
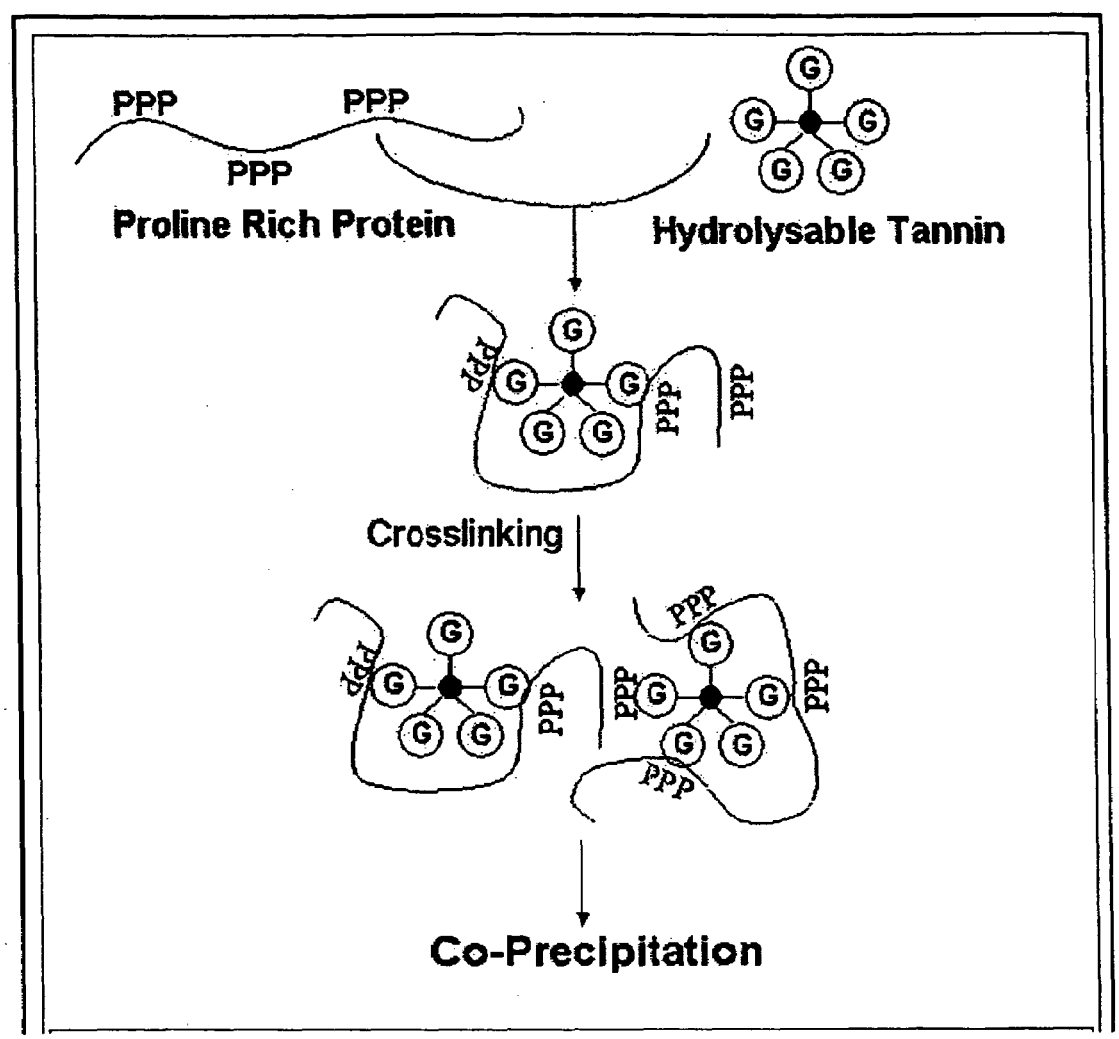
FIG. 12 shows a schematic representation of the mechanism of tannin-protein co-precipitation.

HTs precipitate proteins under normal physiological conditions. The mechanism for tannin-protein co-precipitation proceeds from: 1) formation of a complex between the tannin and protein molecule and 2) precipitation of the complex from solution (FIG. 12) (Kawamoto and Nakatsubo, 1997a; Kawamoto et al., 1995; 1996). Galloyl moieties on the tannin form hydrophobic associations with hydrocarbon-rich R-groups and/or hydrogen bonds with amide groups on the protein (Kawamoto et al., 1997; Feldman et al., 1999; Charlton et al., 1996). Protein binding affinity increases with an increasing number of galloyl groups per tannin molecule and a minimum of three galloyl moieties are required for the complex to occur Kawamoto and Nakatsubo, 1997b; Feldman et al., 1999). The position of the galloyl moieties on the glucose core also influences protein-HT binding affinity. For example, Kawamoto et al. reported that 2,3,6-trigalloyl glucose precipitated proteins more readily than 2,3,4-trigalloyl glucose and 4,6-digalloyl glucose had greater affinity for proteins relative to 2,3-digalloyl glucose (Kawamoto et al., 1996). Increasing steric hindrance between individual galloyl groups appears to decrease tannin induced precipitation (Kawamoto et al., 1996). In addition, formation of the protein-tannin complex is directly proportional to the size and concentration of proteins in solution (Kawamoto et al., 1997; Charlton et al., 1996; Hagerman and Butler, 1991). Following formation of the initial complex, proteins can either co-precipitate with the tannin or re-solublize back into solution (Hagerman and Butler, 1991). A minimum number of galloyl-protein interactions are required for the protein to precipitate. For instance, at least thirty galloyl groups must be complexed with bovine serum albumin (BSA) before precipitation can occur (Kawamoto et al., 1996). Several other factors that favor protein precipitation include decreased temperature and increased ionic strength (Kawamoto and Nakatsubo, 1997a; 1997b). Maximum levels of precipitation take place when the proteins' isoelectric point (pI) equals the pH of solution. Under these conditions, high electrostatic repulsion between protein molecules gives rise to tannin-induced co-precipitation (Kawamoto and Nakatsubo, 1997b).

Nutritive Effects of Tannins

Although high levels of tannins in the diet appear to have negative effects on animal nutrition, there is a considerable amount of discrepancy between the various studies. For instance, some studies reported a reduction in growth rate due to tannins, whereas others have reported negligible (if any) effects (Jacob et al., 1996; Madacsi et al., 1988; Smith et al., 1989; Elkin et al., 1990; Douglas et al., 1990). Several experimental factors may account for these results (Hagerman and Butler, 1991). First, many of the feeding studies used tannin supplements (tannic acid for HTs and quebracho for condensed tannins) that resulted in experimental levels of tannins much higher than those occurring in naturally high tannin feedstuffs. (Makkar et al., 1995; Jacob et al., 1996). Animals would not normally ingest such high concentrations. Further, tannins were quantitatively assayed in these studies using a variety of different methods many of which must be considered inappropriate for recording tannins at high concentrations. Some of these studies failed to report the levels of protein in the diet; low levels of protein increase overall animal sensitivity to tannins (Jacob et al., 1996). While it is generally accepted that high levels of tannins in feedstuffs have negative consequences on animal health and nutrition, it has recently been recognized that low to moderate levels in the diet (up to 6% of the dry matter) provide several substantial benefits to humans, ruminants and other vertebrates. Julier et al. (2002 and 2003) found that forage species differed significantly in their protein degradability, that this was related to the tannin content of those species. Alfalfa was highest in degradability of protein among species, meaning that it is probably least efficient in the utilization of the protein fraction. Variation for tannins in alfalfa is quite low (Julier et al., 2003). Many believe that introduction of moderate tannin concentration into alfalfa would improve the protein degradation of that crop (Martin et al., 2005). In fact, some animals preferentially select foods that contain low levels (i.e., 2% dry matter) of HTs (Clauss et al., 2003).

Antioxidants

Both condensed and hydrolysable tannins are antioxidants, that is, they prevent oxidation of nucleic acids, proteins, carbohydrates, lipids and other cellular components (Clauss et al., 2003). Tannins reduce levels of active oxygen species implicated in the development of over 100 diseases including cancer, atherosclerosis, rheumatoid arthritis, and cataracts (Parr and Bolwell, 2000). Free radicals can damage: 1) DNA, serving as an initiation event for cancer and 2) membrane lipids, involved in the development of heart disease (Eyles et al., 2004). HTs function as antioxidants by preventing free radical formation and free radical chain propagation. For instance, Amakura, et al. (2002) demonstrated that HTs inhibit lipid peroxidation and superoxide anion radical generation. Gallic acid has antioxidant activity at stomach pH and can scavenge $H_2O_2$ radicals (Yilmaz and Toledo, 2004). Tannins form relatively stable complexes with proteins in the gut and it has been proposed that they prevent oxidative damage within the gastrointestinal system (Hagerman et al., 1998). The number and position of galloyl groups on an HT molecule affects its level of antioxidant activity (Eyles et al., 2004). Gallic and ellagic acid are strong antioxidants and the number of these moieties on the tannin is directly proportional to the compound's free radical scavenging properties (Hagerman et al., 1998; Amakura et al., 2002). In fact, addition of a single galloyl group to a flavanol (i.e., condensed tannin monomer) increases its antioxidant activity 5-fold (Okamura et al, 1993). Also, HTs are more effective antioxidants than condensed tannins (Hagerman et al., 1998).

Improved Nitrogen Absorption in Grazers

Figure 13:
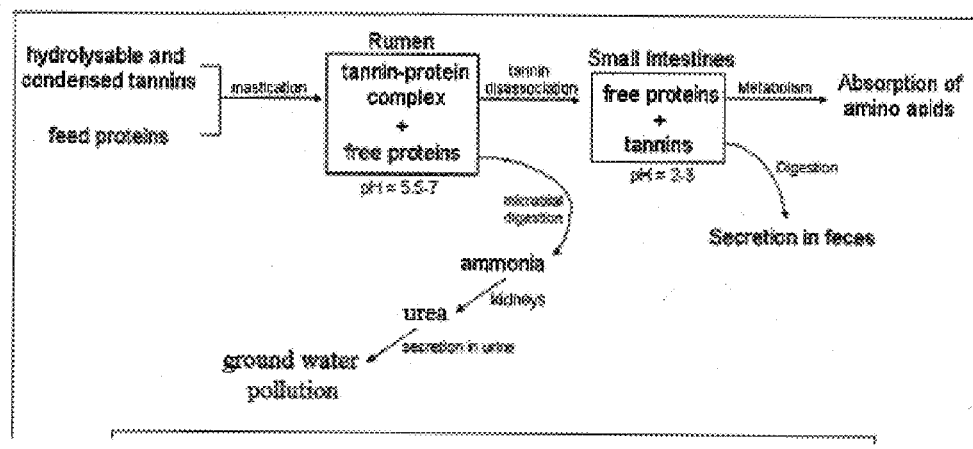
FIG. 13 shows the protection of feed proteins through tannin-protein complexes.

Moderate levels of tannins in feed (2-4% dry matter) increase live weight gain, wool production, and milk yield without reducing voluntary intake in ruminants (Clauss et al., 2003; Waghorn, 1990; Aerts et al., 1999a; Barry and McNabb, 1999). Tannins increase the bioavailability of ingested feed proteins by inhibiting their digestion by the ruminal microbial populations. Tannins released after mastication form insoluble tannin-protein complexes that are stable at rumen pH. These associations occur primarily in the mouth and are stabilized by the slightly acidic pH of complexed with tannins and this ultimately increases the flow of protein (up to 50% higher flux) to the small intestine (FIG. 13) (Waghorn et al., 1990; O'Donovan and Brooker, 2001). The protein-tannin complexes dissociate post-ruminally under the more acidic conditions (pH 2-3) of the abomasum; the released proteins can then be metabolized by the animal (Sliwinski et al., 2002; Parez-Maldonado et al., 1995; McSweeney et al., 2001). In fact, tannins in feed increase the uptake of essential amino acids between 20-60% (Clauss et al., 2003; Barry and Manley, 1986).

The mechanism by which tannins reduce ruminal degradation of protein is that tannins bind to protein to form a tannin-protein complex which is stable at ruminal pH but dissociates at lower pH making protein available for enzymatic digestion. Without the protection of tannins, more than 70% of feed proteins can be digested by rumen microorganisms; ammonia is released as a by-product of this metabolism. The ammonia is subsequently absorbed into the rumen, converted into urea and excreted in the urine. Therefore, by reducing the digestion of proteins by ruminal microbes, tannins reduce the level of ammonia produced and secreted (Sliwinski et al., 2002; Aerts et al., 1999a; 1999b). This, in turn, has positive environmental ramifications including reduction of ammonia volatilization from the soil and groundwater pollution (Aerts et al., 1999a).

In addition to improving nitrogen utilization, tannins also reduce bloat in foragers such as cattle (Bhat et al., 1998; Waghorn, 1990). This condition can occur after grazing when soluble proteins in the rumen may form a stable, frothy foam preventing escape of fermentation gasses. The rumen expands, reducing voluntary intake by the animal. In severe cases, mortality results when the internal organs are compressed by the swollen rumen (Aerts et al., 1999a). Traditionally bloat has been treated by daily, oral applications of detergents to dispel the ruminal foam. This remedy however imposes several economic constraints such that the presence of residues from the detergents necessitates an increased withholding time before slaughter. Importantly, the inclusion of even low levels of tannins in the diet (0.5% dry matter) can eliminate the onset of bloat in ruminants (Barry and McNabb, 1999; Jones et al., 1973). Incorporation of these compounds into feed could therefore serve as an environmentally friendly and economically sound solution to treating bloat in cattle and other grazers (Aerts et al., 1999a; Barry and McNabb, 1999).

Impacts on Ration Balancing

It has been found that simple steps to improve the so-called "by-pass" protein of soybeans or alfalfa by roasting or heating increases milk production substantially (Broderick, 2002). In one study, the effects of heating alfalfa hay (which effectively reduces the amount of protein N quickly released in the rumen, and improves by-pass protein) caused 17% CP alfalfa diets to produce the same milk yields as diets supplemented to provide 23% CP (Broderick et al., 1993). This means that alfalfa with reduced ruminant breakdown of N and improved by-pass protein would provide greater value to dairy nutritionists and producers, saving large amounts of purchased protein supplements. The equivalent of a 6% savings in CP content would enable considerable economic savings to the dairy producer. Considerable literature now exists to support the potential role of tannins in improving dairy protein utilization. High tannin Birdsfoot Trefoil fed on an equivalent protein basis resulted in 11 lbs/day improved milk yield compared with low-tannin alfalfa (Martin, 2005). High tannin alfalfa silages are projected to produce an improvement of 460 lbs of milk per cow in 70% alfalfa silage diets. In simulation studies of the potential effects of condensed tannins, high tannin alfalfa has been projected to be worth $11 more per ton of dry matter compared with conventional varieties. These projections and evaluations were made with condensed tannins. Although the potential effects of HT on milk production are not known, if improved protein utilization results from these genes, it should have a significant effect on ration balancing, and therefore the value of HT-alfalfa varieties. This creates a potential demand for a HT alfalfa product that is based upon real value to the consumer (the dairy producer), since it represents a real cost savings. Additionally, HT alfalfa represents a 'value added' trait that could be used to market specific high-forage quality alfalfa varieties at a higher price by seed producers and farmers.

Potential Impacts on the Environment

Approximately 7.5 MT of alfalfa hay is produced each year in California, resulting in 1.65 MT of protein production. It should be noted that the vast majority of this nitrogen (e.g. 80%) is from biological nitrogen fixation, not from the use of fertilizers (as is the case with other crops such as corn and grain). However, if an estimate that up to 80% of the nitrogen in alfalfa is rapidly degraded in the rumen and much of this N is excreted by the animal, a substantial percentage of this N is not utilized effectively by the animal. A realistic goal of a program to improve the by-pass protein of alfalfa is to move the crop from the current 20-25% rumen by-pass protein to 35-40% by-pass protein (Martin et al., 2005), enabling alfalfa to be closer in efficiency to the more protein efficient protein sources, such as roasted soybean. If the concepts of introduction of HT into alfalfa are successful at reducing rumen degradable protein, and improving by-pass protein and protein efficiency, this would result in a reduction of environmental impact on a per-animal basis. If currently 80% of the N in alfalfa protein is excreted by ruminants as urea it is estimated that of the 265,000 MT of N fed each year from alfalfa, over 200,000 MT of N results in nitrogenous compounds (ammonia converted to nitrate). These compounds place groundwater at risk from contamination, particularly on sandy soils. Moving alfalfa to 40% rumen undegradable protein in California would enable a reduction of over 50,000 MT of Nitrogen from animal wastes each year, and a concomitant reduction in the impact of animal systems on groundwater quality.

Definitions

In order to facilitate review of the various embodiments of the invention, the following definitions are provided:

Elevated Level: Elevated level, as used herein, means an increase in the average level of a substance in a non-naturally occurring plant when compared to the average level in the corresponding naturally occurring plant. Given that the level of any given compound in a plant will vary from plant to plant depending upon a number of variables, one of skill in the art would understand that in comparing the average level of a substance in a non-naturally occurring plant and the corresponding naturally occurring plant, a reasonably sized sample population of each type of plant grown under similarly controlled conditions should be compared. The level of the substance is preferably measured in several plants from each population and averaged to determine whether the non-naturally occurring plant contained an elevated level. The elevated level in the non-naturally occurring plant of the present invention is, on average, at least about 20% greater, 40% greater, 60% greater, 80% greater, 100% greater, 150% greater, 200% greater, 250% greater, 300% greater, 400% greater, or 500% greater than in the corresponding naturally occurring plant.

Higher Level: Higher level, as used herein, is used with a similar meaning as elevated level, except where elevated level refers to a non-natural increase in a substance, higher level means a higher average level of a substance in one plant when compared to the level in a related plant. The plants could be two varieties of a type of plant or a transgenic and non-transgenic plant of the same variety. As an example, a transgenic plant overexpressing shikimate dehydrogenase would be said to have both an elevated level of gallic acid and a higher level of gallic acid, in each case as compared to the non-transgenic. By contrast, a transgenic *J. regia* cv. Tulare expressing a gene unrelated to the gallic acid level would be said to have a higher level of gallic acid than *J. regia* ssp. Chandler, which naturally has a lower level of gallic acid. However, the transgenic *J. regia* cv. Tulare would not be said to have an elevated level of gallic acid, because the higher level is unrelated to the modification that made the plant non-natural and the proper comparison would be the non-transgenic *J. regia* cv. Tulare, which would have the same level of gallic acid. The same would be true for transgenic plants expressing PPO.

Given that the level of any given compound in a plant will vary from plant to plant depending upon a number of variables, one of skill in the art would understand that in comparing the average level of a substance in one plant and a related plant, a reasonably sized sample population of each type of plant grown under similarly controlled conditions should be compared. The level of the substance is preferably measured in several plants from each population and averaged to determine whether the first plant contained a higher level. The higher level in a first plant could be, on average, at least about 20% greater, 40% greater, 60% greater, 80% greater, 100% greater, 150% greater, 200% greater, 250% greater, 300% greater, 400% greater, or 500% greater than in the second plant.

Localized to a Tissue: As referred to herein, a substance is said to be localized to a particular plant tissue or tissues when the substance is found at a higher concentration in a particular tissue or tissues than in other tissues in the plant. Given that the distribution in different tissues of any given substance in a plant will vary from plant to plant depending upon a number of variables, one of skill in the art would understand that in comparing the average level of a substance in a particular tissue or tissues and the other tissues in a plant, a reasonably sized sample population of each such plant grown under similarly controlled conditions should be compared. The level of the substance is preferably measured in the different tissues from several plants and averaged across the plants to determine whether the substance was localized to a given tissue as herein defined. The localization in the present invention is, on average, at least about 20% greater, 40% greater, 60% greater, 80% greater, 100% greater, 150% greater, 200% greater, 250% greater, 300% greater, 400% greater, or 500% greater in the specified tissue or tissues than in the other tissues of the plant.

A substance that is localized to a particular tissue such as the seed or nut pellicle may also be localized to certain other tissues such as flower stamen and still be considered localized to the seed or nut pellicle. Localized as used herein refers to the substance being found in at least one specified tissue at a higher concentration than the average distribution in all the other plant tissues. Examples of preferred tissues for localized elevated levels in plants are the floral/reproductive tissues, including, but not limited to, the testa, the seed hairs, the hull epidermis, the hull cortex, the shell, the pellicle, the husk, the seed coat, the kernel, the embryo, the pod, the peg, the seed, and the seed coat, as appropriate for the plant of interest. Thus, one of skill in the art would understand that a non-naturally occurring plant with an elevated level of gallic acid or PPO localized to the seed or nut pellicle means that the relative concentration of gallic acid or PPO in the seed or nut pellicle compared to average concentration in the rest of the non-naturally occurring plant is greater than the relative concentration in the seed or nut pellicle compared to the average concentration in the rest of naturally occurring plant.

Plastid: A plastid refers to a cytoplasmic organelle fulfilling one of three functions: 1) photosynthesis (chloroplast), 2) storage (amyloplasts, proteinoplast, elaioplast) or 3) orange, red and/or yellow pigmentation (chromoplast). All plant cells contain one or more types of plastids. All plastids contain DNA distinct from the nuclear genome and are derived from proplastids present in egg and meristematic cells (Fahn 1990).

Transit Peptide: A transit peptide is an N-terminal extension present on many nuclear encoded plastid proteins. Such transit peptides can be approximately one hundred residues in length or longer. Transit peptides are necessary and sufficient to target proteins from the cytosol to the plastid. During import, the region corresponding to the transit peptide is cleaved off to generate the mature protein (Zhang 2002, Nakrieko 2004). It has been demonstrated that transit peptides are neither species nor protein specific and do not appear to influence the activity of the mature protein (Lee 2002).

Shikimate Dehydrogenase Protein: A shikimate dehydrogenase protein or polypeptide is a protein that catalyzes the conversion of 3-dehydro-shikimate (also referred to as 5-dehydro-shikimate) to gallic acid. The enzymatic conversion of 3-dehydro-shikimate to gallic acid is gallic acid synthesis activity. Representative but non-limiting shikimate dehydrogenase sequences useful in the invention include the protein sequence SEQ ID NO: 2, and the corresponding cDNA SEQ ID NO: 1.

Figure 14:
FIG. 14 shows that plant SkDH proteins, including that from walnut, consist of the DHQase and Shikmate dehydrogenase domains. The NCBI web interface for Blast provided this graphic when the walnut SkDH amino acid sequence was submitted as a query for protein-protein Blast. In the resulting web graphic, each of the colored bars would be hyperlinked to additional information about each domain in the NCBI Conserved domain database (CDD).

Shikimate Dehydrogenase in plants incorporates two enzymatic functions in one polypeptide chain (Bonner and Jensen 1992). The first of these, corresponding to the AroD, or dehydroquinase I (DHQase) domain, catalyzes the cis-dehydration of 3-dehydroquinate via a covalent imine intermediate to produce 3-dehydroshikimate. The second enzymatic function corresponds to the AroE, or shikimate dehydrogenase (SkDH) domain. This catalyses the reduction of dehydroshikimate to shikimate, coupled to the oxidation of NADPH (bound by the enzyme) to NADP+. FIG. 14 shows the linear structure of the two domains.

Figure 15:
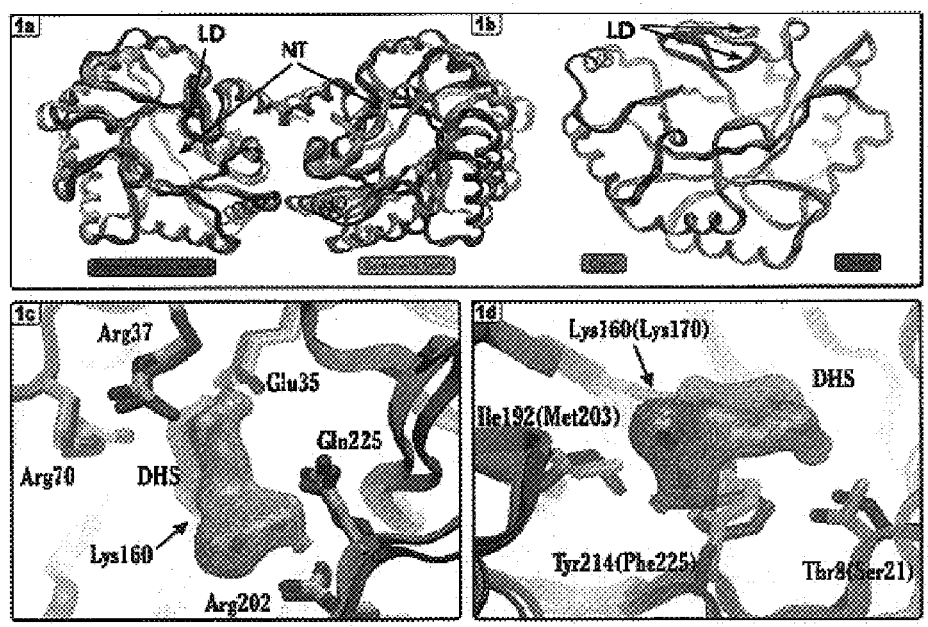
FIG. 15 shows the 3D structure of the active site of the DHQase domain, reproduced from FIG. 1 in Nichols et al (2004). Residues indicated in the two lower panels are highlighted in light blue in FIG. 3. The original text of the figure caption follows: Ribbon format CA-trace overlays of DHQases: (a) Full dimer of *S. aureus* (red/purple) and *S. typhi* (cyan) DHQases in closed form with *S. aureus* regions showing high mobility in the open form coloured purple, (LD: Lid Domain; NT: N-terminal anti-parallel -sheet region). (b) Single domain overlay of *S. aureus* open (green) and closed (red) structures. (c-d) Close up views of DHQase active site overlays with selected *S. typhi* residues shown in red and equivalent *S. aureus* residues colored by atom type (DHS: 3-dehydroshikimate; numbers in parentheses indicate *S. typhi* residue numbers). Electron density for DHS shown contored at 1.

FIG. 15 (reproduced from Nichols et al. 2004) shows the 3D structure of the active site of the DHQase domain of two bacterial species. The multiple sequence alignment (FIG. 16) suggests that in all likelihood it is very similar, structurally and functionally, to that in *J. regia* and other plants. In both the DHQase and SkDH domains, multiple sequence alignments (FIGS. 16, 18, and 19 created by the ClustalX program) suggest that the same is true of both domains of the *J. regia* enzyme.

Figure 16:
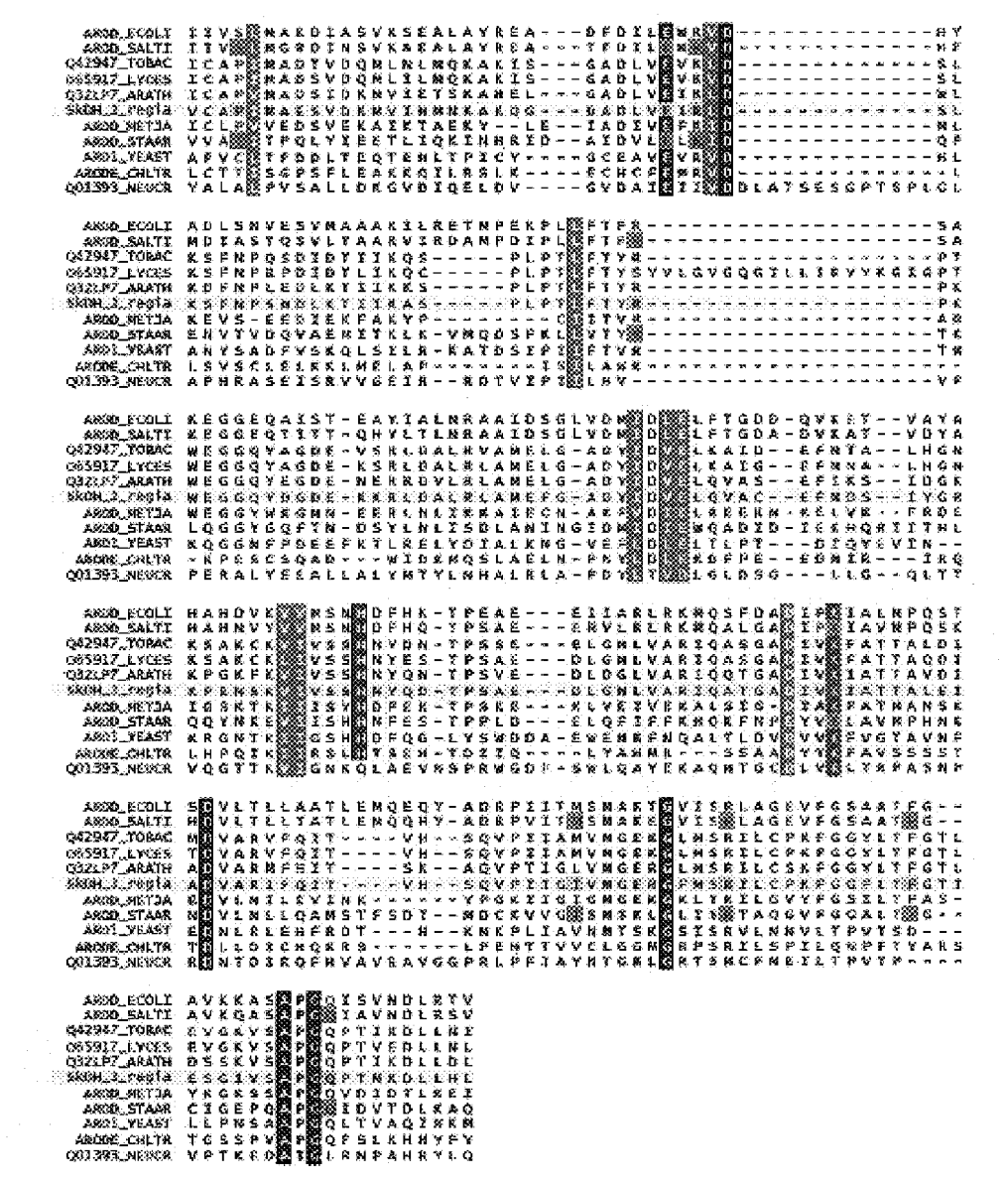

The multiple sequence alignment in FIG. 16 includes the DHQase domain (roughly the first half) of the *J. regia* SkDH sequence, along with three other sequences from plants, and seven DHQase domain sequences from microorganisms. In this multiple sequence alignment, as well as in FIGS. 18 and 19, species name abbreviations after the underscore (except for *J. regia*) in the left-hand column correspond to those given in Table A. The full sequences in FIGS. 16, 18, and 19 (except for that of *J. regia*), can be accessed through the Swiss-Prot Protein Knowledgebase.

TABLE A

| | |
|---|---|
| AQUAE | *Aquifex aeolicus* |
| ARATH | *Arabidopsis thaliana* |
| BACSU | *Bacillus subtilis* |
| CHLTR | *Chlamydia trachomatis* |
| ECOLI | *Escherichia coli* |
| HAEIN | *Haemophilus influenzae* |
| HUMAN | *Homo sapiens* |
| IPOBA | *Ipomoea batatas* (sweet potato) |
| LYCES | *Lycopersicon esculentum* (tomato) |
| MALDO | *Malus domestica* (apple) |
| METJA | *Methanococcus jannaschii* |
| NEUCR | *Neurospora crassa* |
| OCTDO | *Octopus dofleini* (giant octopus) |
| PSEAE | *Pseudomonas aeruginosa* |
| RANNI | *Rana nigromaculata* (frog) |
| SALTI | *Salmonella typhi* |
| SOLTU | *Solanum tuberosum* (potato) |
| SPIOL | *Spinacia oleracea* (spinach) |
| STAAM | *Staphylococcus aureus* (strain Mu50) |
| STAAR | *Staphylococcus aureus* (strain MRSA252) |
| STRPN | *Streptococcus pneumoniae* |
| THEMA | *Thermotoga maritima* |
| TOBAC | *Nicotiana tabacum* (common tobacco) |
| VICFA | *Vicia faba* (broad bean) |
| YEAST | *Saccharomyces cerevisiae* |

Figure 17:
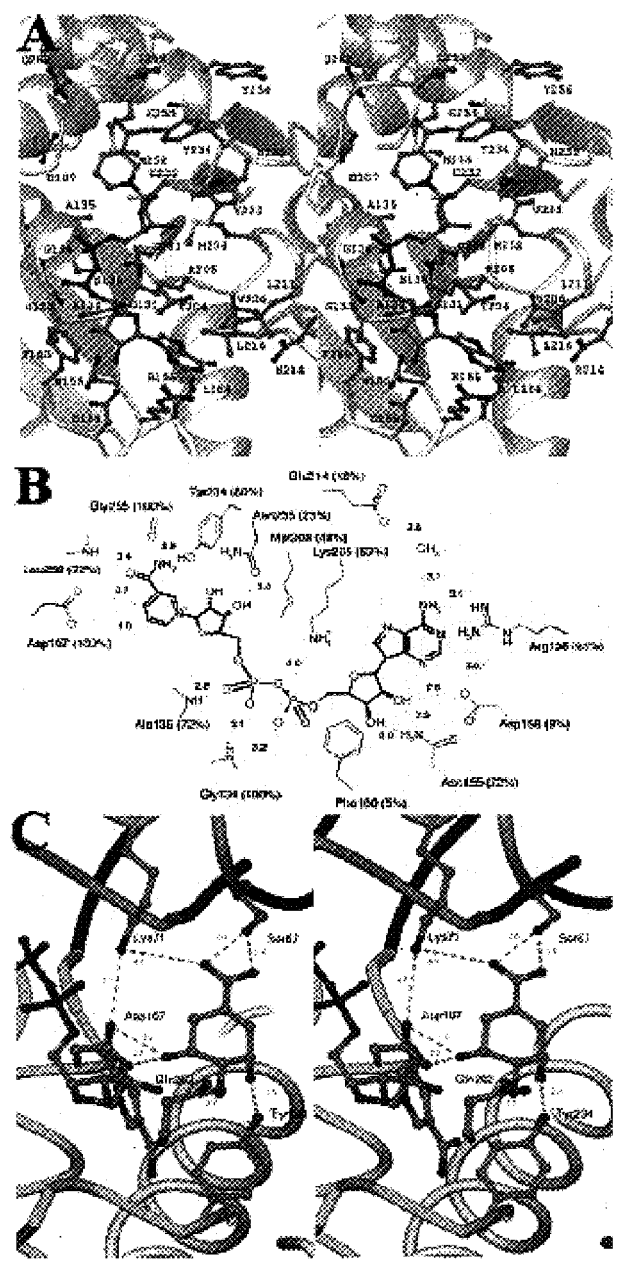
FIG. 17 shows a 3D structure of SkDH active site of the YdiB protein of *E. coli*, reproduced from FIG. 4 in Benach et al. (2003). Residue numbers correspond to those cited in FIG. 18, (multiple sequence alignment of AroE, shikimate DH domain). The original text of the figure caption of Benach et al. follows: The shikimate dehydrogenase active site. 17A, stereo pair showing the environment of the crystallographically observed NAD+molecule bound to YdiB. Residues within a 5-Å radius of the NAD+ atoms are shown. 17B, schematic plot of the molecular interactions of the bound NAD+ molecule. Distances are given in Å, and the numbers in parentheses represent the percentage of identity in all the sequences in the shikimate dehydrogenase cluster of orthologous genes. 17C, stereo pair showing the proposed binding mode for a molecule of shikimate in the active site of YdiB. Distances are given in Å. All of the side chains shown here are 100% conserved in the shikimate dehydrogenase cluster of orthologous genes with the exception of Ser-67 (which is only substituted with threonine) and Tyr-234 (which is present in 37 of 43 sequences). The protein backbone is colored according to domain as in FIG. 2A (in Benach et al. 2003).
Figure 18:
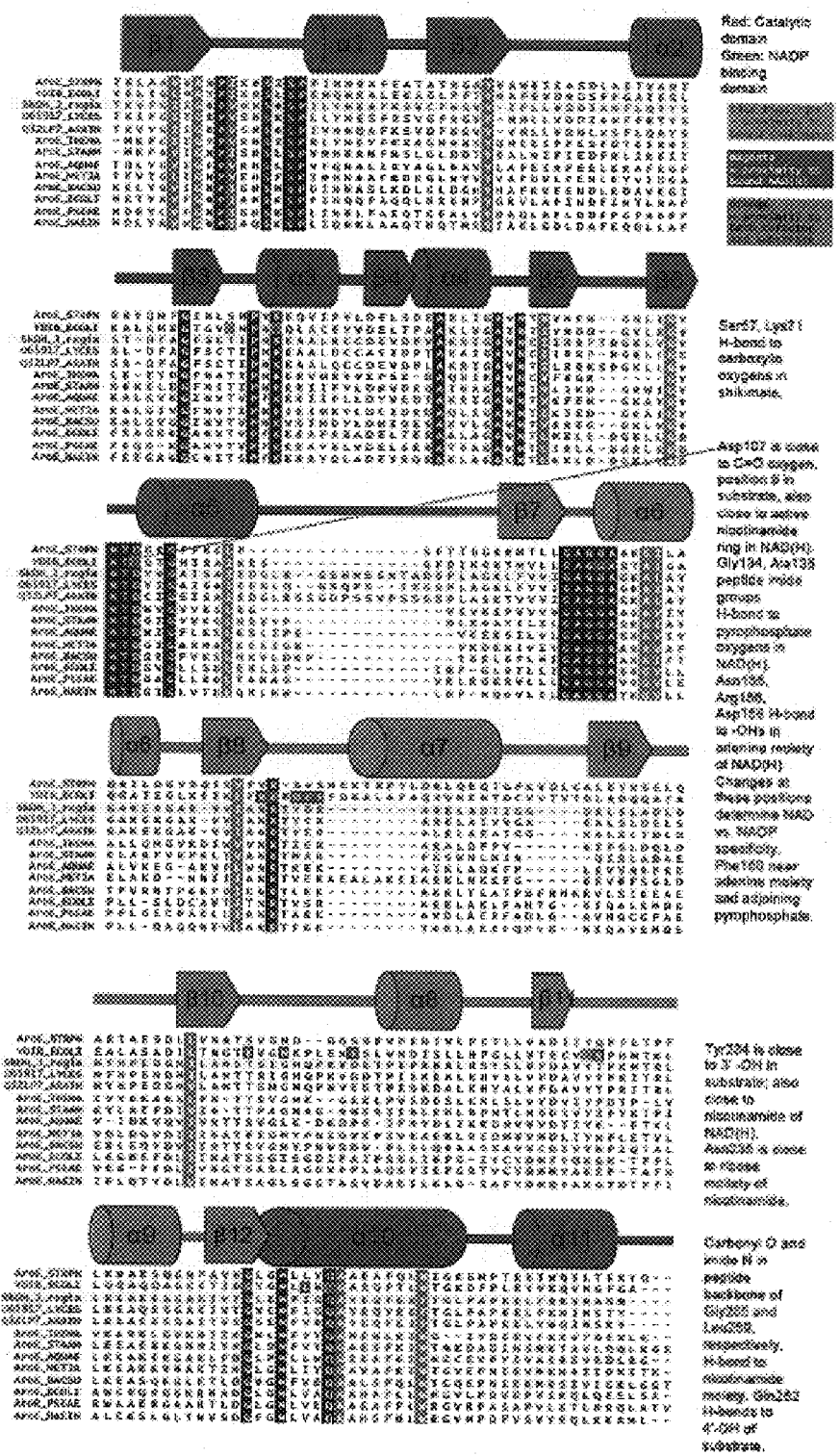
FIG. 18 shows a multiple sequence alignment of the AroE, shikimate DH domain, with 100% conserved residues highlighted (identical and chemically similar amino acids, black and gray vertical columns, respectively). The *J. regia* sequence, amino acids 284 to 562 (N-terminus)(SEQ ID NO: 24), is highlighted with yellow background. Additional blue, pink and magenta highlights indicate those residues identified by Benach et al. (2003), FIG. 4, as features of the active site of the YdiB protein from *E. coli* (SEQ ID NO: 23). A light blue highlight indicates proximity to bound shikimate; a magenta highlight indicates proximity to bound NAD(H); an orange highlight indicates proximity to both substrate and cofactor. Notations in the right-hand column refer to residue numbers of YdiB, in FIG. 4 of Benach et al. 2003. Secondary structure (red and green boxes) is based on FIG. 1B of Ye et al. (2003). SEQ ID NOS: 22-34 are shown in FIG. 18.
Figure 19:
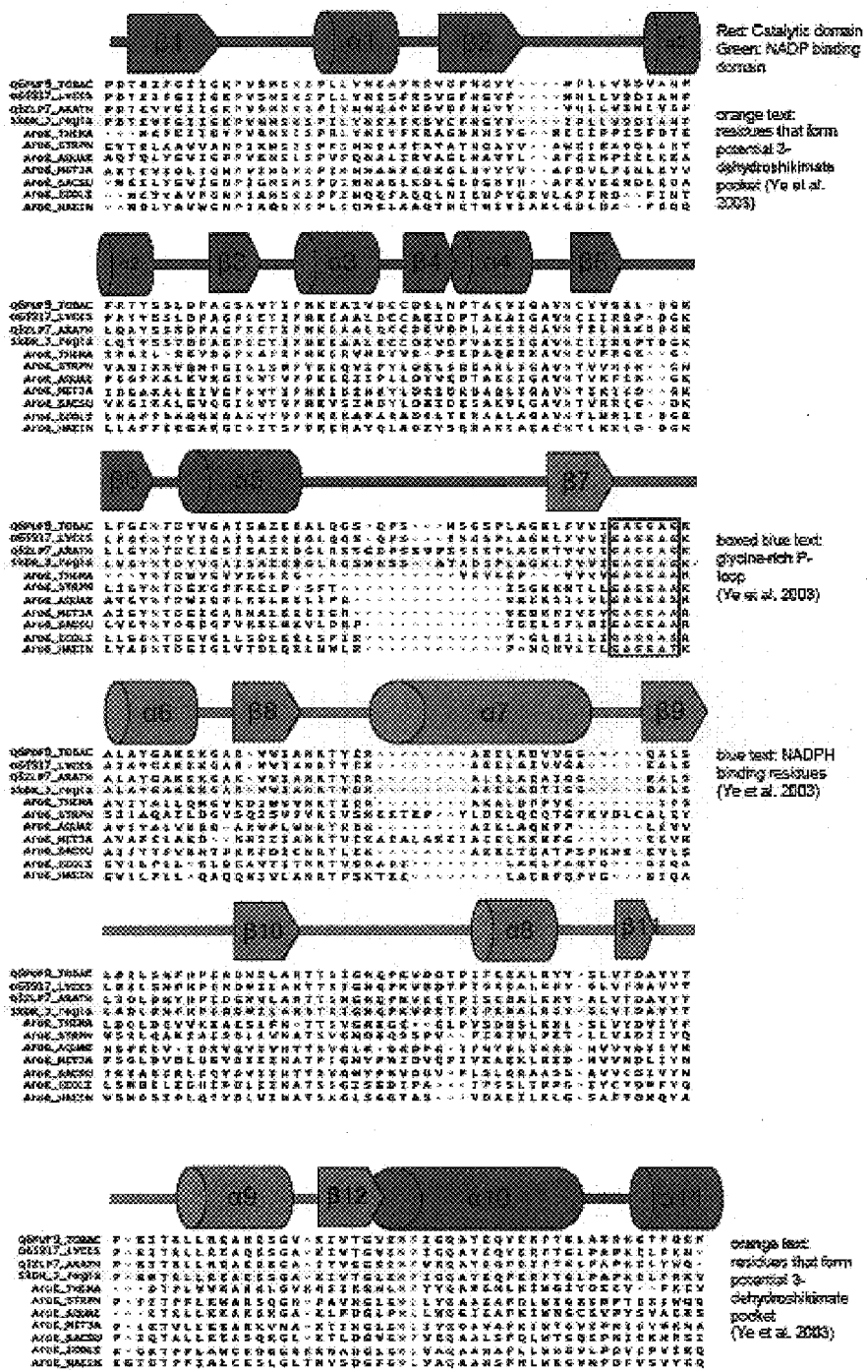
FIG. 19 shows a multiple sequence alignment of the AroE, shikimate DH domain, based on FIG. 1B in Ye et al. (2003). The *J. regia* sequence, amino acids 282 to 558 (SEQ ID NO: 38), is highlighted with yellow background. Colored text and secondary structure boxes above the alignment indicate features of the structure, as described by Ye et al., FIG. 1A. Graphic features are the same as those used in FIGS. 1A and B of Ye et al. (red=catalytic domain, green=NADP binding domain). See right-hand column for additional explanation of the latter. SEQ ID NOS: 35-45 are shown in FIG. 19.
Figure 20:
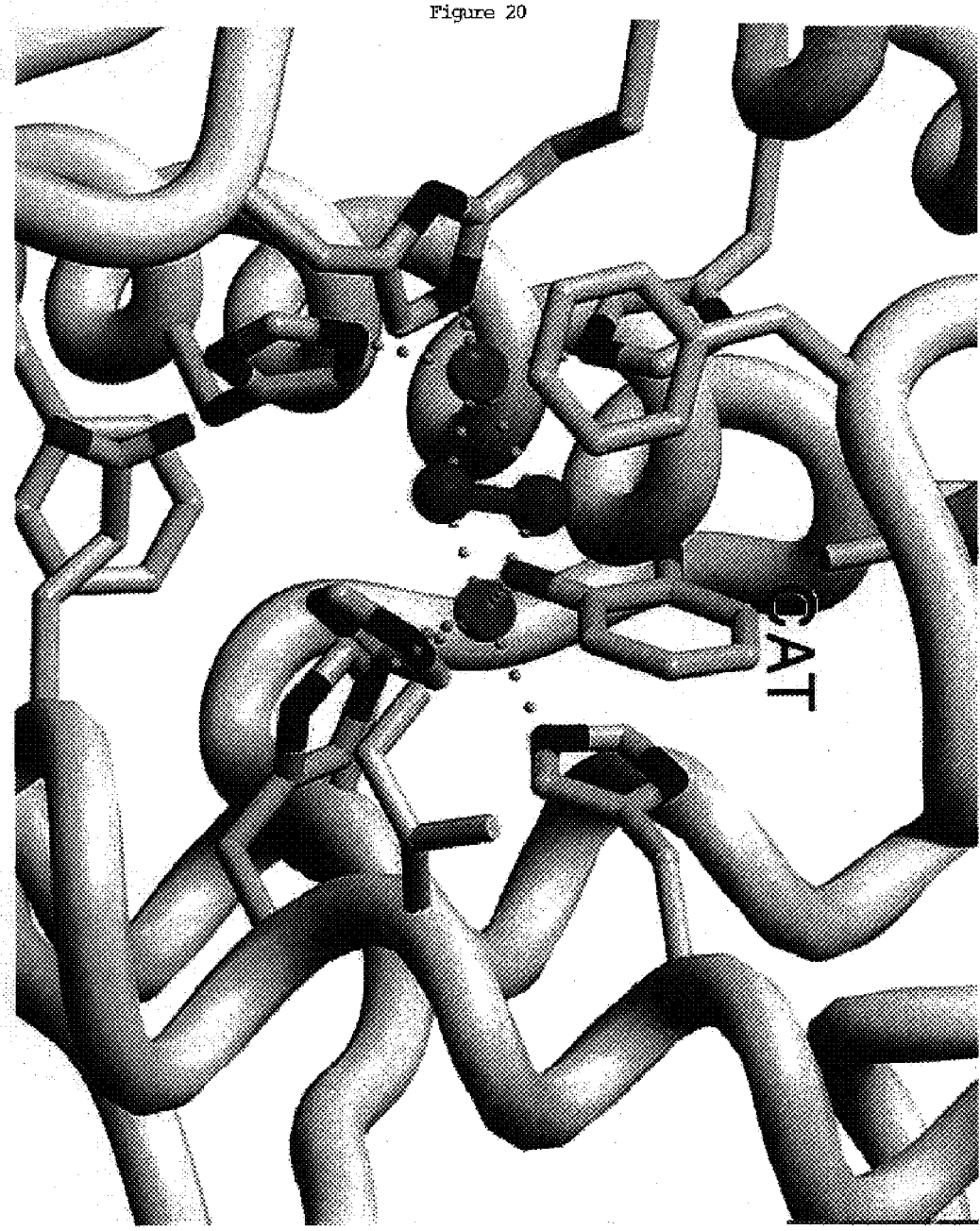
FIG. 20 shows a 3D structure of the active site of catechol oxidase (PPO homolog) with bound catechol substrate ("CAT") and O$_2$, based on X-ray crystallographic studies from the sweet potato enzyme (Protein Data Bank ids. 1BUG, 1BT1, 1BT2, 1BT3; PPO1_IPOBA in FIG. 21). The position of the substrate molecule is deduced from the X-ray structure of the enzyme with bound substrate analog phenylthiourea (PTU). Oxygen atoms are colored red, nitrogen dark blue (in histidine residues), copper light blue, sulfur yellow (in Cys-92, linked to His-109). The Cu ion and three histidine residues of the CuA site, and those same features of the CuB site, appear on the left and right, respectively, on either side of the O$_2$ molecule. Glu-236 is the oxygen-containing group near the bottom of the image (reproduced from Klabunde et al. 1998).
Figure 21A:
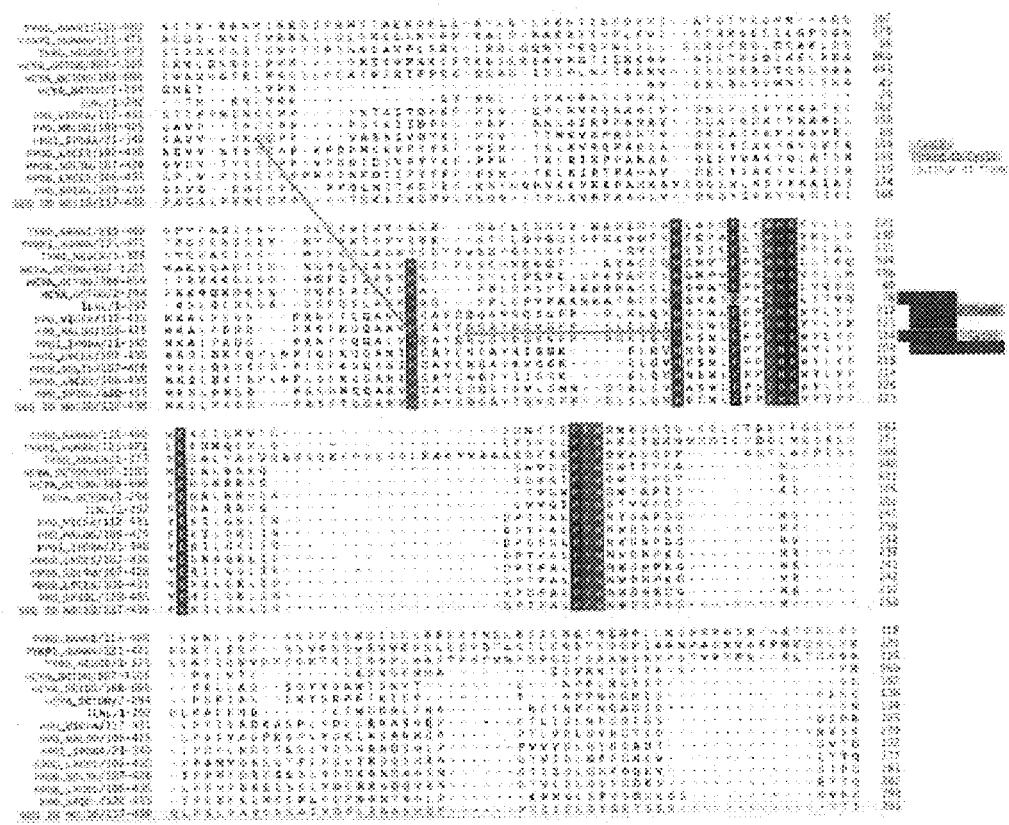
FIG. 21 shows a multiple sequence alignment of polyphehol oxidase sequences and homologs, including tyrosinases (TYR), hemocyanins (HCYA and 1LNL), and PPOs from several species. All PPO sequences in this figure are plant enzymes. Gray and black columns indicate conserved residues (same as described in FIGS. 16, 18, and 19). Covalent linkages between cysteine residues (including the unusual Cys-His linkage in the CuA site) are indicated with green lines. Based on the high degree of sequence similarity, these linkages and other important features are likely to occur at the same locations in all plant PPOs. The residues of the CuA and CuB sites are indicated in maroon and teal highlights, respectively. Other residues which function in the active site are highlighted in blue. These active site features are described in 3D crystallographic studies of hemocyanin (1LNL sequence (SEQ ID NO: 52) in this figure; Perbandt et al. 2003), and catechol oxidase (Klabunde et al. 1998). Abbreviations for species names are given in Table A. Sequence identifiers containing the underscore character (except for SEQ ID NO:10 and 1LNL (SEQ ID NO: 52)) correspond to entry names in the UniProtKB/Swiss-Prot knowledgebase (available at ca.expasy.org/uniprot). 1LNL (SEQ ID NO: 52) is the Protein Data Bank accession for hemocyanin from sea snail. The effects on enzyme functionality due to amino acid variation at specific sites have been examined in detail in various studies. Hemandez-Romero et al. (2006) suggest that the phenylalanine present in all plant PPOs at position 261 in PPO1_IPOBA (SEQ ID NO: 55) sterically hinders access to the active site, and plays a role in the affinity for o-diphenol over monophenol substrates. Gerdemann et al. (2001) found that a change from isoleucine to threonine at position 241 alters functionality. SEQ ID NOS: 46-60 are shown in figure 21.
Figure 22:
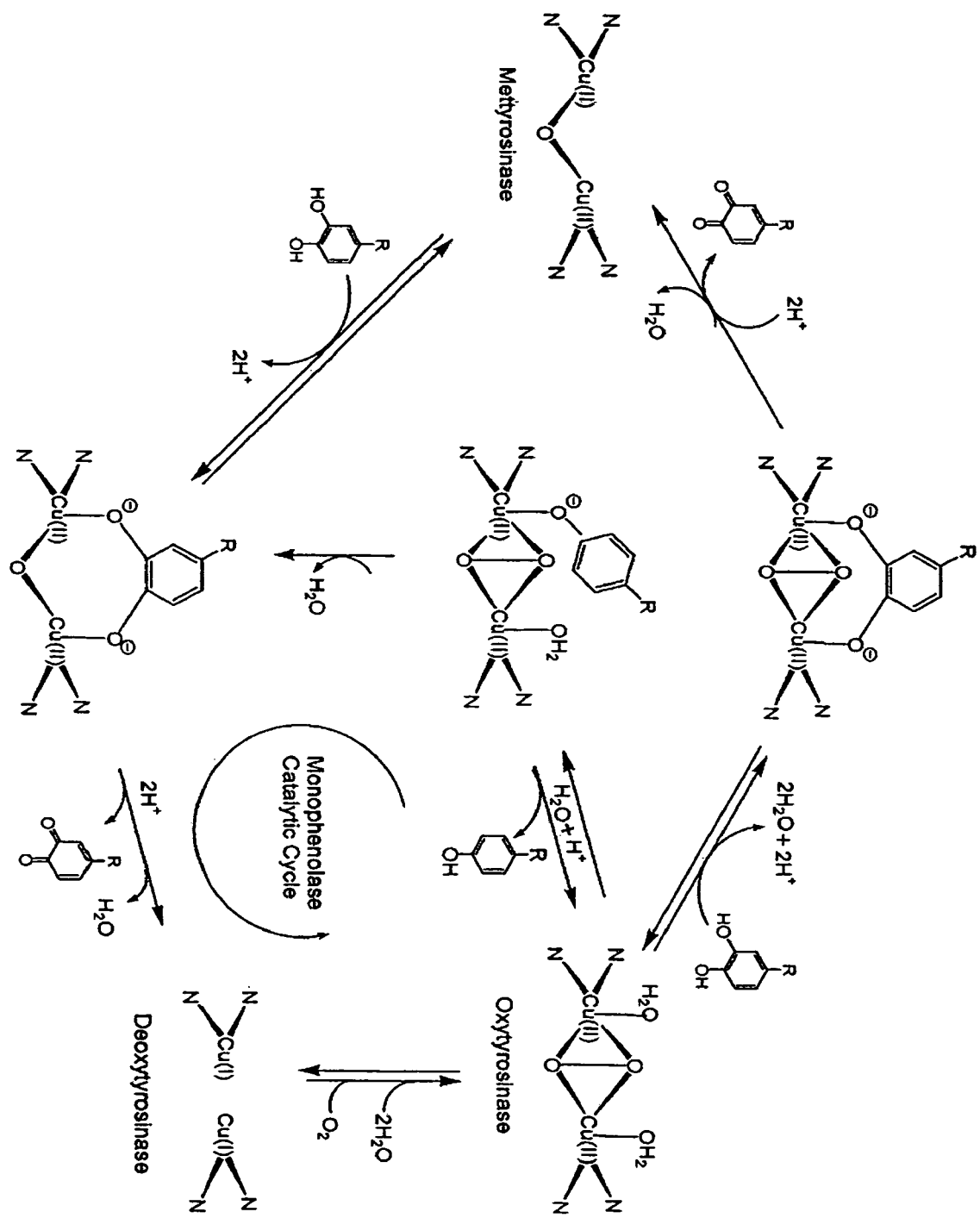
FIG. 22 shows catalytic cycles of the hydroxylation of monophenol and oxidation of o-diphenol to o-quinone by tyrosinase (PPO homolog). "N" atoms in the figure belong to histidine residues of the CuA and CuB sites (only four, of six total, shown for simplicity) (reproduced from Kim and Uyama (2005)).

In both FIGS. 18 and 19, the secondary structure, based on that published by Ye et al. (2003) for the AroE enzyme from *Haemophilus influenzae*, is shown above the alignment. This secondary structure differs slightly from that described for the YdiB structure (FIG. 2 in Benach et al. 2003; not shown). FIG. 18 gives more relevant information pertaining to the enzymatic function. FIG. 19 gives some additional information, based on the study of the structure of AroE of *H. influenzae* (Ye et al. 2003). Of the articles published to date on the structure of the SkDH active site, Benach et al. (2003), analyzing the *E. coli* YdiB protein at 2.3-Å resolution, and Michel et al., comparing YdiB and AroE from *E. coli*, give the most detailed information of which residues in the sequence interact with both the bound substrate and cofactor (FIG. 17). Although in YdiB, the latter is NAD rather than NADP, relevant features of the structure and mechanism probably are essentially the same. The amino acid side groups most relevant to the reduction of dehydroshikimate and synthesis of gallic acid, are aspartic-107, and tyrosine-234, indicated in color in FIG. 18. (Numbering is based on the YdiB sequence.) Details of the catalytic mechanism are discussed in the final two paragraphs of the article on the YdiB crystal structure (Benach et al. 2003).

The present invention may be practiced using nucleic acid sequences that encode full length shikimate dehydrogenase protein as well as shikimate dehydrogenase-derived proteins that retain the gallic acid synthesis activity. The preferred shikimate dehydrogenase proteins are derived from plants, more preferably from nut crops. Shikimate dehydrogenase-derived proteins which retain gallic acid synthesis activity include fragments of shikimate dehydrogenase protein, generated either by chemical (e.g., enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "shikimate dehydrogenase protein" encompasses full-length shikimate dehydrogenase proteins, as well as such shikimate dehydrogenase derived proteins that retain gallic acid synthesis activity.

Polyphenol Oxidase (PPO): Polyphenol oxidase (PPO) is a type-3 copper protein which catalyzes the oxidation of monophenols or o-diphenols to o-quinones (Klabunde et al., 1998). PPO-generated quinones are highly reactive, and will crosslink with proteins or polymerize, generating dark-colored tannins and melanins in vivo (Walker and Ferrar, 2001). PPO is of substantial commercial interest due to its central role in postharvest browning of a variety of crops (e.g., apple, potato, pineapple) (Murata et al., 2001). In intact plant cells, plastid localized PPO is physically separated from its phenolic substrates, which reside primarily in the vacuole. Thus, PPO activity is generally observed only upon loss of cellular compartmentalization caused by senescence, wounding, or other tissue damage (Steffens et al., 1994).

Characterized plant PPO isoforms range from ~40-72 kDa, with preproteins often undergoing substantial post-translational modifications in the form of N-terminal plastid transit peptide processing and C-terminal proteolysis (Van Gelder et al., 1997). All PPOs possess two highly conserved copper binding domains (CuA, CuB), each containing several canonical histidine residues which form a $Cu^{2+}$ binding site (Klabunde et al., 1998). In addition, most plant PPOs possess a third histidine-rich region at the C-terminus of the protein (CuC), which may also be involved in copper binding (Steffens et al., 1994). PPO is often isolated from plant tissues in a latent form which can be activated by a range of treatments, including proteolysis, aging, and incubation with detergents. Unlike animal and fungal PPOs (tyrosinases), plant PPOs often lack monophenol oxidase (cresolase) activity, limiting potential substrates to diphenolic compounds such as catechol, 3,4-dihydroxyphenylalanine (DOPA), and chlorogenic acid (Steffens et al., 1994).

PPOs are often, but not exclusively, encoded by multigene families in plants. For example, seven PPO-encoding genes have been identified in tomato and six in potato, while PPO appears to be encoded by a single gene in grape and spinach (Van Gelder et al, 1997). Characterized PPO-encoding genes in plants are generally ~2 kb in length and lack introns. They display distinct tissue specific and developmental regulation, with young leaves, fruits, and flowers possessing the highest PPO transcript levels in several different species (Steffens et al., 1994). Once produced, the PPO enzyme appears to be quite stable in vivo, as high activity is often maintained in older leaf and fruit tissues in the absence of detectable transcription (e.g., Dry and Robinson, 1994; Gooding et al., 2001; Sullivan et al., 2004). In several plant species, most notably potato, tomato, and hybrid poplar, PPO transcription and activity is upregulated in leaves by wounding and the wound signaling compounds methyl jasmonate and systemin (Constabel et al., 2000; Thipyapong and Steffens, 1997; Constabel and Ryan, 1998).

PPO has several defined roles in animals, including skin/exoskeleton pigmentation and cuticle sclerotization (Steffens et al., 1994). In plants, however, the physiological function of PPO is substantially less clear, as most PPO research has focused on the agricultural implications of PPO-mediated postharvest browning (Vaughn et al., 1988). Recently, several specialized PPO enzymes have been shown to be involved in the biosynthesis of aurone pigments in snapdragon (Nakayama et al., 2001), betalin pigments in pokeweed (Joy et al., 1995; Gandía-Herrero et al., 2005), and 8-8' linked lignans in creosote bush (Cho et al., 2003). In addition, a protective function of leaf PPOs has long been hypothesized (reviewed by Kosuge, 1969), and several recent studies have provided strong support for a role in plant defense against pathogens and insects. Insect herbivory strongly induces PPO activity in vivo (Constabel et al., 2000), and larvae of Colorado potato beetle, forest tent caterpillar, and common cutworm display increased mortality and decreased growth when fed leaves of plants overexpressing PPO (Steffens et al., 1994; Thipyapong et al., 2004; Wang and Constabel, 2004). Similarly, viral, bacterial, and fungal challenge can induce PPO activity (Mayer and Harel, 1979), and PPO-overexpressing tomatoes display enhanced resistance to the bacterial pathogen *Pseudomonas syringae* (Li and Steffens, 2002). Protective effects of PPO have generally been attributed to the generation of reactive quinones, which may (1) possess direct bacteriocidal and fungicidal properties (Vaughn et al., 1988), (2) generate toxic reactive oxygen species through secondary oxidation reactions (Steffens et al., 1994), (3) reduce protein palatability and digestibility by oxidizing nucleophilic amino acids (Felton et al., 1992), and (4) form an impermeable melanin barrier, preventing the spread of pathogen infection (Van Gelder et al., 1997).

Promoter: A regulatory nucleic acid sequence, typically located upstream (5') of a gene or protein-coding sequence that, in conjunction with various cellular proteins, is responsible for regulating the expression of the gene or protein-coding sequence. The promoters suitable for use in the heterologous nucleic acids of this invention are functional in plants and in other host organisms used for expressing the inventive polynucleotides. Many plant promoters are publicly known. These include constitutive promoters, regulated promoters, inducible promoters, root-, tissue- and cell-specific promoters, and developmentally-regulated promoters. Exemplary promoters and fusion promoters are described, e.g., in WO 02/00894, which is herein incorporated by reference.

The promoters may be those normally associated with a transgene of interest, or heterologous promoters which are derived from genes of other plants, viruses, and plant pathogenic bacteria and fungi. Those skilled in the art will be able without undue experimentation to select promoters that are suitable for use in practicing the subject invention.

Regulated Promoter: As used herein, this term refers to any promoter functional in a plant that provides differential expression levels in response to stimuli internal to the plant such as developmental signals. This includes both promoters that increase expression and promoters that decrease expression in response to stimuli or changed external conditions. Many promoters that are regulated promoters are also inducible promoters. For example, promoters that are responsive to auxin are both regulated and inducible because they will change levels of expression in response to developmental changes in auxin levels and in response to externally supplied auxin.

Examples of regulated promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051, both herein incorporated by reference), glob-1 promoter, and gamma-zein promoter. An exemplary promoter for leaf- and stalk-preferred expression is MS8-15 (see U.S. Pat. No. 5,986,174, herein incorporated by reference). Examples of seed-preferred promoters included, but are not limited to, 27 kDa gamma zein promoter and waxy promoter (Boronat et al. (1986); Reina et al. (1990); and Kloesgen et al. (1986)). Promoters that express in the embryo, pericarp, and endosperm are disclosed in U.S. application No. 60/097,233, filed Aug. 20, 1998, and U.S. application No. 60/098,230, filed Aug. 28, 1998, both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression. Examples of preferred promoters include, without limitation, the histone H2B promoter, such as from corn (Rasco-Gaunt 2003); the ABC transporter GhWBC1 promoter, such as from cotton (Zhu 2003); the Ara h 1 promoter, such as from peanut (Viquez 2003) and the shikimate dehydrogenase promoter, such as from *J. Regia* cv. Tulare.

Tissue Specific Promoter: As used herein, this term refers to any promoter functional in a plant that provides differential expression levels in different tissues within the plant. Such promoters may provide tissue specific expression in one or several tissues. Many promoters that are tissue specific are also regulated promoters. For example, some promoters specifically express in plant seeds only during certain stages of the seeds growth cycle.

Examples of tissue specific promoters include those listed above that initiate transcription only, or preferentially, in certain tissues, such as leaves, roots, fruit, seeds, or flowers. Examples from above include anther specific promoters, leaf- and stalk-specific promoters, seed-specific promoters, embryo-specific promoters, pericarp-specific promoters, and endosperm-specific promoters. Additionally, as discussed above under localization, tissue specific expression occurs when there is on average a skewed expression in one or more tissues of a plant when compared to the average expression in the other tissues in such plant.

Figure 4A:
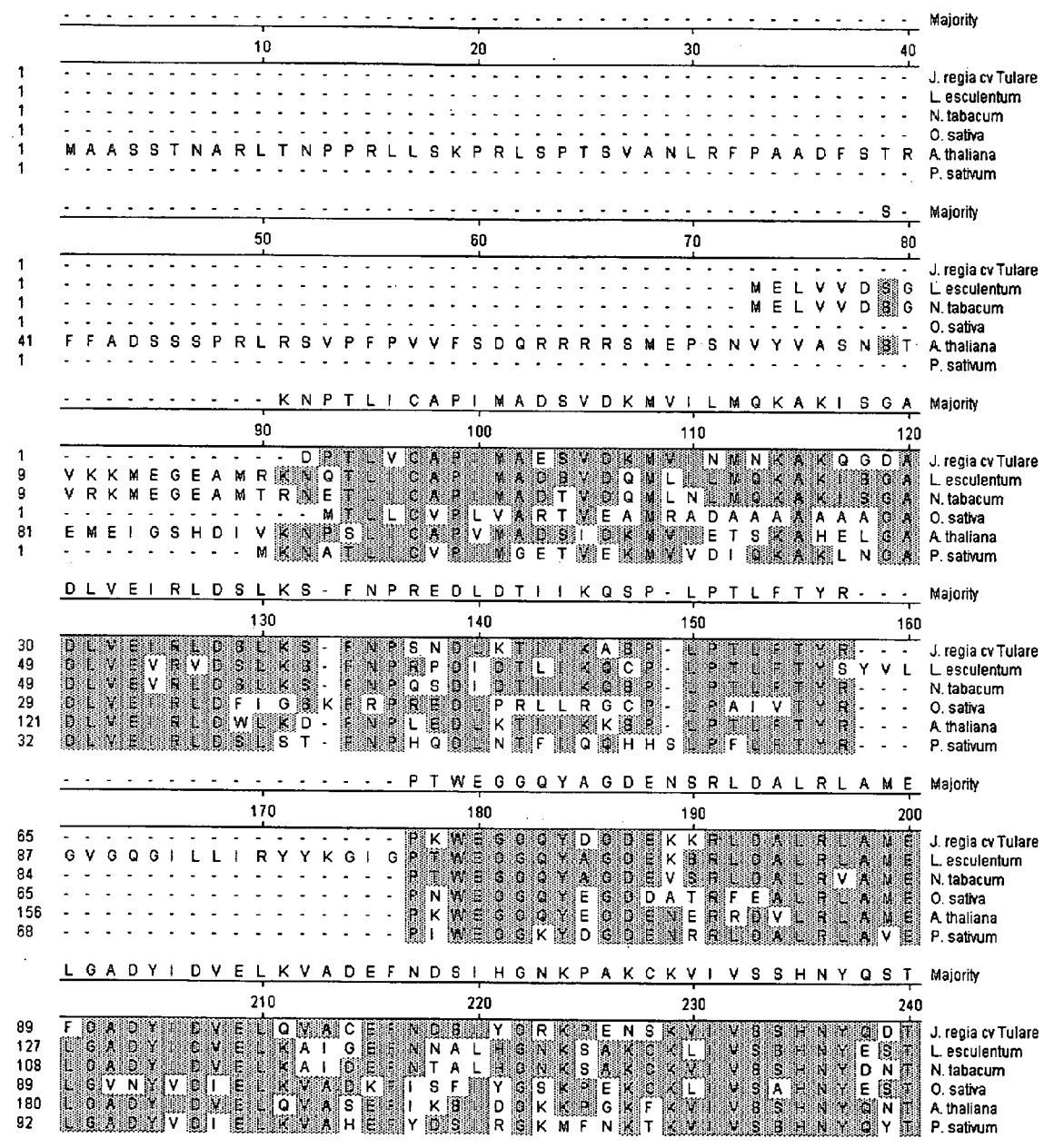
Figure 4B:
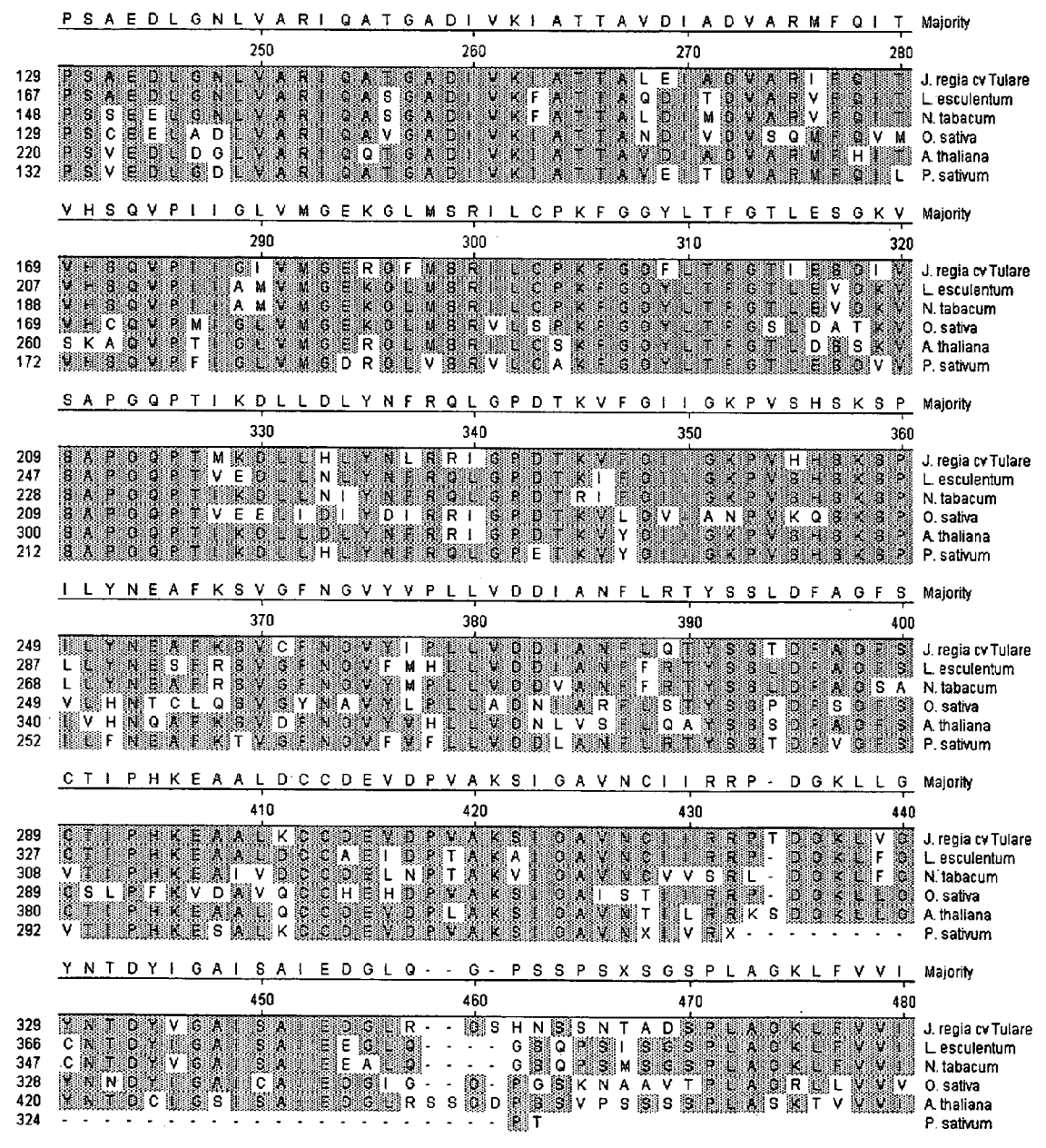

Sequence Identity: Sequences that show similarity to those described in this application such as those depicted in FIG. 4 can be identified by computer-based methods, using public domain sequence alignment algorithms and sequence similarity search tools to search sequence databases (public domain databases include Genbank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences, or two amino acid sequences may be expressed in terms of sequence identity (or, for proteins, also in terms of sequence similarity). Sequence identity is frequently measured in terms of percentage identity; the higher the percentage, the more similar the two sequences are. As described herein, homologs and variants of the shikimate dehydrogenase encoding nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

Homologs of the disclosed nucleic acid sequences are typically characterized by possession of at least 40% sequence identity counted over the full length alignment with the nucleic acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

The alignment may include the introduction of gaps in the sequences to be aligned. In addition, for sequences which contain either more or fewer amino acids than the protein depicted in SEQ ID NO:2, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein for nucleic acids, and the protein homology described for proteins or polypeptides.

Stringency: Stringency refers to hybridization conditions chosen to optimize binding of polynucleotide sequences with different degrees of complementarity. Stringency is affected by factors such as temperature, salt conditions, the presence of organic solvents in the hybridization mixtures, and the lengths and base compositions of the sequences to be hybridized and the extent of base mismatching, and the combination of parameters is more important than the absolute measure of any one factor.

Very High Stringency: Very high stringency conditions refers to hybridization to filter-bound DNA in 5×SSC, 2% sodium dodecyl sulfate (SDS), 100 µg/ml single stranded DNA at 55-65° C. for 8 hours, and washing in 0.1×SSC and 0.1% SDS at 60-65° C. for thirty minutes.

High Stringency: High stringency conditions refers to hybridization to filter-bound DNA in 5×SSC, 2% sodium dodecyl sulfate (SDS), 100 µg/ml single stranded DNA at 55-65° C. for 8 hours, and washing in 0.2×SSC and 0.2% SDS at 60-65° C. for thirty minutes.

Moderate Stringency: Moderate stringency conditions refers to hybridization to filter-bound DNA in 5×SSC, 2% sodium dodecyl sulfate (SDS), 100 µg/ml single stranded DNA at 55-65° C. for 8 hours, and washing in 0.2×SSC and 0.2% SDS at 50-55° C. for thirty minutes.

Low Stringency: Low stringency conditions refers to hybridization to filter-bound DNA in 5×SSC, 2% sodium dodecyl sulfate (SDS), 100 µg/ml single stranded DNA at 55-65° C. for 8 hours, and washing in 2.0×SSC and 0.2% SDS at 50-55° C. for thirty minutes.

Construct: Unless otherwise stated, the term "construct" refers to a recombinant genetic molecule comprising one or more isolated polynucleotide sequences of the invention.

Genetic constructs used for transgene expression in a host organism include a gene promoter sequence operably linked to an open reading frame coding for at least a functional portion of a polypeptide of the present invention and optionally a gene termination sequence 3' downstream of the open reading frame. The open reading frame may be orientated in either a sense or anti-sense direction, depending upon the intended use of the gene sequence. The construct may also include selectable marker gene(s) and other regulatory elements for gene expression.

Operably Linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter controls the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Vector: The term "vector" refers to a nucleic acid molecule which is used to introduce a polynucleotide sequence into a host cell, thereby producing a transformed host cell. A "vector" may include genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large genomic DNA fragment such as a contig is not sufficiently purified away from other biological components to be considered isolated due to the relatively large amount of extra DNA found in the average contig. As outlined below "recombinant nucleic acids" and "recombinant proteins" also are "isolated" as described above Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell; however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that such artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Complementary DNA (cDNA): A piece of DNA that is synthesized in the laboratory by reverse transcription of an RNA, preferably an RNA extracted from cells. cDNA produced from mRNA may include 5' and/or 3' noncoding sequences (i.e., 5' UTR, 3' UTR) but typically lacks internal, non-coding segments (introns) and regulatory sequences, such as promoters, that determine transcription.

Open Reading Frame (ORF): A continuous coding sequence of a gene flanked by a start and stop codon. An ORF lacks internal termination codons and can usually be translated into an amino acid sequence.

Non-naturally Occurring Plant: A non-naturally occurring plant is a plant that does not occur in nature without human intervention. Non-naturally occurring plants include transgenic plants and plants produced by non-transgenic means such as plant breeding where the trait of interest is specifically selected for throughout the breeding process.

Transgenic Plant: As used herein, this term refers to a plant that contains recombinant genetic material not normally found in plants of this type, as well as recombinant genetic material normally found in such plants but in an abnormal position in the genome, and which has been introduced into the plant in question (or into progenitors of the plant) by human manipulation. Thus, a plant into which recombinant DNA is introduced by transformation is a transgenic plant, as are all offspring of that plant that contain the introduced transgene (whether produced sexually or asexually). It is understood that the term transgenic plant encompasses the entire plant and parts of the plant, for instance grains, seeds, flowers, leaves, roots, fruit, pollen, stems etc.

Standard molecular biology methods and plant transformation techniques can be used to produce transgenic plants that produce plants having a recombinant gene or genes providing gallic acid or PPO synthesis activity.

Ortholog: Two nucleotide or amino acid sequences are orthologs of each other if they share a common ancestral sequence and diverged when a species carrying that ancestral sequence split into two species, sub-species, or cultivars.

Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may include modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated. In the present invention, a gene for shikimate dehydrogenase is described above.

Primer: The terms "primer" and "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase Chain Reaction (PCR): A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

Plants of the Present Invention

The present invention encompasses non-naturally occurring plants containing elevated levels of gallic acid or PPO. Preferred embodiments include plants in which the elevated levels are at least 20%, at least 40%, at least 60%, at least 80%, at least 100%, at least 150%, at least 200%, at least 250%, at least 300%, at least 400%, or at least 500% higher than in the comparable naturally occurring plant. In certain embodiments, the elevated levels may be localized to specific tissues. In preferred embodiments, the elevated levels are localized to the floral/reproductive tissues, including, but not limited to, the testa, the seed hairs, the hull epidermis, the hull cortex, the shell, the pellicle, the husk, the kernel, the embryo, the pod, the peg, the seed, and the seed coat, as appropriate for the plant of interest. In yet another variation, the tissue of the non-naturally occurring plant contains at least 4%, at least 4.5%, at least 5%, at least 5.5%, at least 6%, at least 7%, at least 8%, at least 10%, or at least 12% by dry weight gallic acid or PPO.

A preferred embodiment of the non-naturally occurring plants of the present invention is a plant transgenically expressing an enzyme or enzymes capable of synthesizing such elevated level of gallic acid, or PPO. In one variation, the transgenic plant includes one or more genes that provide PPO gallic acid synthesis activity.

A preferred example is a transgenic plant comprising a shikimate dehydrogenase gene that has gallic acid biosynthesis activity. Such shikimate dehydrogenase genes may include any of the constructs detailed below. The preferred plants are walnut, peanut, cotton, corn, alfalfa and other forage crops. Plants expressing PPO will compartmentalize the protein to the chloroplast and the enzyme is activated when the tissues are crushed and the enzyme gets in contact with the phenolic substrates usually present in the plant vacuole. A similar action will occur when the leaf tissue is chewed by animals or insects. Once the endogenous substrate and enzyme is mixed the reaction will create highly reactive quinine compounds that will crosslink proteins making them more difficult to degrade. Should the endogenous levels be insufficient then potential phenolic substrates can be applied externally, this would be particularly useful in the preparation of silage, where action of PPO can lead to the greater preservation of proteins and amino acids.

Uses of the Invention

By way of example and not of limitation, the following uses of the invention are described and are therefore included in the scope of the invention:

The non-naturally occurring plants with elevated levels of gallic acid of the present invention will be useful for crop plants that are susceptible to aflatoxin contaminations. Such plants will innately inhibit the aflatoxin production without addition of fungicides or exogenously added chemicals.

The non-naturally occurring plants with elevated levels of gallic acid of the present invention will also be useful as a source of gallic acid and therefore the invention includes methods of cultivating such plants and extracting the gallic acid. Gallic acid obtained by such extraction may be applied to other plants and plant products to inhibit aflatoxin production.

The non-naturally occurring plants with elevated levels of gallic acid of the present invention may also contain elevated levels of ellagic acid. Therefore another aspect of the present invention is non-naturally occurring plants with elevated levels of ellagic acid, which may be generated by the same methods used to generate the non-naturally occurring plants with elevated levels of gallic acid. The invention further includes methods of cultivating such plants and extracting the ellagic acid. Ellagic acid obtained by such extraction has use as an anti-oxidant as well as other uses.

The non-naturally occurring plants with elevated levels of gallic acid will have corresponding elevated levels of hydrolysable tannins that contain gallic acid residues. These hydrolysable tannins will complex proteins and improve protein utilization. The synthesis of additional GA could lead to the suppression of lignin thereby greatly improving the digestibility and fermentation for feed or for feed stocks for synthesis of bio fuels. The presence of higher levels of GA could lead to the greater accumulation of GACTs as explained above, many of these have potent anti-paricidal activity and could protect cattle from ruminant and digestive tract parasites. Some of the GACTs could be used to protect humans against viral and parasitic infestations.

The non-naturally occurring plants with elevated levels of PPO will also have improved protein utilization. As explained above, the action of PPO with endogenous of externally provided phenolic substrates will lead to the creation of highly reactive quinones that will crosslink proteins and other cellular macromolecules making them difficult to digest by ruminant organisms and insect pests. PPO action in the preparation silage will prevent the loss of plant proteins to microbial degradation, thus, making a feed with a higher protein content.

In addition, nucleic acids of the invention will be useful in generating the non-naturally occurring plants of the present invention. The shikimate dehydrogenase encoding genes may be used to identify such genes in other species. In addition, the shikimate dehydrogenase encoding nucleic acid will be useful in designing probes that may be used to detect shikimate dehydrogenase encoding nucleic acid expression levels and specific variants of shikimate dehydrogenase genes. Such probes may be useful in breeding plants with particular shikimate dehydrogenase genes or expression patterns. The PPO encoding genes may be used to identify such genes in other species. In addition, the PPO encoding nucleic acid will be useful in designing probes that may be used to detect PPO encoding nucleic acid expression levels and specific variants of PPO. Such probes may be useful in breeding plants with particular PPO genes or expression patterns.

The nucleic acids of the invention will also be useful in antisense, sense suppression or RNAi constructs that may be introduced into plants or other organisms to lower the expression of or inhibit the expression of shikimate dehydrogenase or PPO. Such constructs, plants and other organisms are therefore additional aspects of the present invention.

Transformation or transfection of prokaryotic or eukaryotic host cells with the nucleic acid of the shikimate dehydrogenase gene will be useful in amplifying, modifying, and transforming the shikimate dehydrogenase gene into plants. The primers and vectors of the invention will be useful for the same purposes. Modification of the shikimate dehydrogenase encoding nucleic acid and the shikimate dehydrogenase amino acid sequence may entail mutagenesis, deletions, additions, fusions, or other alterations of various parts of the gene or protein in order to change its activity, thereby altering the gallic acid synthesis activity of the shikimate dehydrogenase protein, such as increasing the preference for synthesizing gallic acid over shikimate. Such mutations, deletions, substitutions, additions, and fusions of the shikimate dehydrogenase encoding nucleic acid and protein are within the scope of the invention. Shikimate dehydrogenase encoding nucleic acid fusions may include the use of heterologous promoters to alter the regulation of the shikimate dehydrogenase gene.

Transformation or transfection of prokaryotic or eukaryotic host cells with the nucleic acid of the PPO gene will be useful in amplifying, modifying, and transforming the PPO gene into plants. The primers and vectors of the invention will be useful for the same purposes. Modification of the PPO encoding nucleic acid and the PPO amino acid sequence may entail mutagenesis, deletions, additions, fusions, or other alterations of various parts of the gene or protein in order to change its activity, thereby altering the gallic acid synthesis activity of the PPO protein, such as increasing the preference for synthesizing gallic acid over shikimate. Such mutations, deletions, substitutions, additions, and fusions of the PPO encoding nucleic acid and protein are within the scope of the invention. PPO encoding nucleic acid fusions may include the use of heterologous promoters to alter the regulation of the PPO gene.

The antibodies of the invention will be useful in identifying species with polypeptides having similar structural characteristics to the shikimate dehydrogenase polypeptide. Additionally the antibodies of the invention may be used to impair the activity of shikimate dehydrogenase in vitro or in vivo, thereby altering the cell or organism's response to stimuli.

The antibodies of the invention will be useful in identifying species with polypeptides having similar structural characteristics to the PPO polypeptide. Additionally the antibodies of the invention may be used to impair the activity of PPO in vitro or in vivo, thereby altering the cell or organism's response to stimuli.

In addition, gallic acid by itself may be used directly to inhibit aflatoxin production. External application of gallic acid may be used to prevent aflatoxin while the crops are sitting in the field, being shipped to grocers, or sitting on shelves in stores.

Gallic acid in animal feed may be used to increase the bio-availability of ingested feed proteins through inhibiting protein digestion by the ruminal microbial populations. Microbes in the rumen cannot degrade proteins complexed with gallic acid. After the protein-gallic acid complexes dissociate post-ruminally, the released proteins can be metabolized/utilized by the feeding animal (Perez-Maldonado 1995, McSweeney 2001).

In addition, gallic acid in animal feed may be used to reduce ammonia volatilization from the soil and reduce ground water pollution. Because gallic acid inhibits ruminal microbial digestion, the microbes produce lower levels of ammonia. This in turn results in a corresponding reduction in levels of ammonia secreted by the feeding animal (Aerts 1999, Aerts 1999a).

Finally, gallic acid in animal feed may be used to reduce bloat in grazers and foragers such as cattle. Complexes between gallic acid and protein in the rumen prevent the formation of frothy foam required for the onset of bloat in these animals (Jones 1973, Barry 1999).

Constructs

The present invention includes various aspects of nucleic acid sequences encoding one or more proteins that provide gallic acid biosynthesis activity. A preferred embodiment of the nucleic acid of the present invention is an isolated nucleic acid encoding a shikimate dehydrogenase protein or fragment thereof having gallic acid biosynthesis activity. Examples of such nucleic acids include nucleic acids that hybridize to the shikimate dehydrogenase encoding nucleic acids disclosed herein under low, moderate, high or very high stringency, nucleic acids with 40%, 50%, 60%, 70%, 75%, 80%, 85%, 90%, 95%, or 97% identity to the shikimate dehydrogenase encoding nucleic acids disclosed herein, and nucleic acids encoding a protein with 40%, 50%, 60%, 70%, 75%, 80%, 85%, 90%, 95%, or 97% identity to the shikimate dehydrogenase proteins disclosed herein. In addition, the nucleic acids may include nucleic acids that encode proteins that share conserved regions with other shikimate dehydrogenase proteins when aligned with shikimate dehydrogenase protein families such as the *A. thaliana, L. esculentum, N. tabacum, O. sativa,* and *P. sativum* proteins. Such conserved regions may share 70%, 75%, 80%, 85%, 90%, 95%, or 97% identity.

The present invention also includes various aspects of nucleic acid sequences encoding one or more PPO enzymes. A preferred embodiment of the nucleic acid of the present invention is an isolated nucleic acid encoding a PPO.

Examples of such nucleic acids include nucleic acids that hybridize to the PPO encoding nucleic acids disclosed herein under low, moderate, high or very high stringency, nucleic acids with 40%, 50%, 60%, 70%, 75%, 80%, 85%, 90%, 95%, or 97% identity to the PPO encoding nucleic acids disclosed herein, and nucleic acids encoding a protein with 40%, 50%, 60%, 70%, 75%, 80%, 85%, 90%, 95%, or 97% identity to the PPO proteins disclosed herein. In addition, the nucleic acids may include nucleic acids that encode proteins that share conserved regions with other PPO proteins when aligned with PPO protein families such as the *A. thaliana, L. esculentum, N. tabacum, O., sativa,* and *P. sativum* proteins. Such conserved regions may share 70%, 75%, 80%, 85%, 90%, 95%, or 97% identity.

The nucleic acid sequence is generally operably linked to a transit peptide that will target the protein to plastids, such as the chloroplast. The precursor for shikimate dehydrogenase, 5-dehydroshikimate, is present in plastids and as such, in order to function, the protein must be targeted to this organelle. Transit peptides that may be used include, but are not limited to: 1) the transit peptide from potato (*Solanum tuberosum* L.) 3-deoxy-D-arabino-heptulosonate 7-phosphate synthase (Jianmin 2002), 2) the transit peptide from the small subunit of ribulose-1,5-bisphosphate carboxylase/oxygenase (Rubisco) from pea (*Pisum sativum*) (Yan-Yun 2000) and 3) the transit peptide from β-amylase (ct-BMY) from *Arabidopsis thaliana* (Nga 1999).

The nucleic acid sequence of the coding region of PPO is also generally operably linked to a transit peptide that will target the protein to plastids, such as the chloroplast. The precursor for PPO do contain endogenous transit peptide and these can be retaines, the mono or diphenolic substrates are not typically present in the chloroplast but are present in abundant supply in the plant vacuole. In order to for PPO to function, the protein must be targeted to this organelle. Transit peptides that may be used include, but are not limited to: 1) the transit peptide from potato (*Solanum tuberosum* L.) 3-deoxy-D-arabino-heptulosonate 7-phosphate synthase (Jianmin 2002), 2) the transit peptide from the small subunit of ribulose-1,5-bisphosphate carboxylase/oxygenase (Rubisco) from pea (*Pisum sativum*) (Yan-Yun 2000) and 3) the transit peptide from β-amylase (ct-BMY) from *Arabidopsis thaliana* (Nga 1999). Also separating the PPO enzyme by targeting it to the chloroplast away from the phenolic substrates in the plant vacuole prevents the invivo action of PPO which could stress the plant due to the synthesis of reactive quinones.

In addition, the present invention includes the above nucleic acid sequences operably linked to a promoter. The preferred promoter is a heterologous promoter. The choice of promoter will be dictated by the target cell, tissue, and/or development expression pattern in which the PPO or shikimate dehydrogenase protein is to be expressed. Selection of an appropriate promoter functional in a desired target cell is routine in the art. One of skill in the art can use, for example, a constitutive promoter, an inducible promoter or a regulated promoter depending upon the desired pattern of expression. In addition to natural promoters, mutant promoters and artificial promoters created by splicing distinct regulatory elements may be used.

Another aspect of the present invention is vectors including the nucleic acids and promoter linked constructs described above. There are a wide range of vectors available to one of skill in the art. Such vectors can include, without limitation, expression vectors, cloning vectors, shuttle vectors, etc. which can include, but are not limited to, the following vectors or their derivatives: human, animal, or plant viruses such as vaccinia virus, adenovirus, cauliflower mosaic virus (CaMV), geminivirus, brome mosaic virus, and tobacco mosaic virus; insect viruses such as baculovirus; yeast vectors; bacteriophage vectors (e.g., lambda), and plasmid (e.g. the Ti plasmid of *Agrobacterium tumefaciens*) and cosmid DNA vectors, to name but a few. Selection of the appropriate vector will be dictated by the target cells, desired expression mode (e.g., transient expression versus permanent integration into the genome versus independently replicating vectors will cause one of skill in the art to select different vectors), and ease of recombinant manipulation. In some circumstances, one of skill in the art would use a shuttle vector that is functional in at least two organisms so that the nucleic acid may be manipulated in one organism and then transferred into the other.

Methods

The present invention also includes methods of making the constructs, vectors, transgenic cells and plants discussed above. The constructs and vectors may be generated using standard molecular biology techniques Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells and regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the introduced recombinant sequence may be referred to as the recombinant expression cassette.

Selection of progeny plants containing the introduced transgene may be made based upon the detection of the recombinant PPO or shikimate dehydrogenase encoding gene in transgenic plants, upon the detection of the recombinant PPO or shikimate dehydrogenase protein-coding sequence or upon enhanced resistance to a chemical agent (such as an antibiotic) as a result of the inclusion of a selectable marker gene incorporated into the transformation vector.

As discussed above, a preferred method of generating the non-naturally occurring plants of the present invention include generating various forms of transgenic plants with elevated levels of gallic acid by expressing the shikimate dehydrogenase. One of skill in the art may use other, less preferred methods of generating such non-naturally occurring plants that could involve multiple enzymes catalyzing two or more reaction steps. Another preferred method of generating the non-naturally occurring plants of the present invention include generating various forms of transgenic plants with elevated levels of PPO.

Successful examples of the modification of plant characteristics by transformation with cloned nucleic acid sequences are replete in the technical and scientific literature. Selected examples, which serve to illustrate the knowledge in this field of technology include: transformation of soybean as described by Ornatowski et al., transformation of rice as described by Terada et al, transformation of walnut as described by Dandekar et al., transformation of alfalfa as described by Desgagnes et al., transformation of peanut as described by Gartland et al., transformation of cotton as described by Leelavanthi et al., U.S. Pat. No. 5,571,706 ("Plant Virus Resistance Gene and Methods"); U.S. Pat. No. 5,677,175 ("Plant Pathogen Induced Proteins"); U.S. Pat. No.

5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants"); U.S. Pat. No. 5,780,708 ("Fertile Transgenic Corn Plants"); U.S. Pat. No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration") all of which are hereby incorporated by reference in their entirety. These examples include descriptions of transformation vector selection, transformation techniques and the production of constructs designed to express an introduced transgene.

The transgene-expressing constructs of the present invention may be usefully expressed in a wide range of higher plants where an altered mycorrhizal and/or rhizobial symbiosis response is useful.

Methods for the transformation and regeneration of monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed above.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. Suitable markers include, without limitation, those genes coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. After transformed plants are selected and grown the plant can be assayed for expression of recombinant proteins.

Proteins

The present invention further includes isolated PPO proteins and shikimate dehydrogenase proteins and fragments thereof with gallic acid biosynthetic activity. The proteins may be isolated by routine techniques available to one of ordinary skill in the art. Such techniques include overexpression in desired target cells and purification therefrom. Standard methods of protein purification include chromatography (e.g., ion exchange, affinity, and sizing column chromatography), centrifugation, differential solubility, or by any other standard technique for the purification of proteins. Such standard techniques may be found in Robert K. Scopes, Protein Purification: Principles and Practice, Springer Verlag, $3^{rd}$ Ed. 1996. In addition, affinity tags may be affixed to the protein via molecular biology to ease purification. Examples include his-tagging and flag-tagging the protein. The functional properties may be evaluated using any suitable assay.

Ligands

The present invention includes ligands that interact with the above described proteins. Such ligands include small molecules, antibodies and other proteins. Antibodies may be generated by standard molecular biology techniques. Small molecule ligands may be identified by standard techniques available to one of ordinary skill in the art. With the automated screening techniques available today, large libraries may be screened with ease once pure protein is available. Such ligands may merely bind to the proteins while others may down regulate or completely inhibit the PPO or gallic acid synthesis activity or upregulate or activate the PPO or gallic acid synthesis activity.

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology, 4th ed., Stites et al., Eds., Lange Medical Publications, Los Altos, Calif., and references cited therein; Harlow and Lane, supra; Goding, Monoclonal Antibodies: Principles and Practice, 2nd ed., Academic Press, New York, N.Y. (1986); and Kohler and Milstein, Nature 256: 495-497 (1975).

Other suitable techniques involve selection of libraries of recombinant antibodies in phage or similar vectors (see, e.g., Huse et al., Science 246:1275-1281 (1989); and Ward, et al., Nature 341:544-546 (1989); and Vaughan et al., Nature Biotechnology, 14:309-314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech., 14:845-851 (1996). Also, recombinant immunoglobulins may be produced. See, Cabilly, U.S. Pat. No. 4,816,567 (herein incorporated by reference in its entirety); and Queen et al., Proc. Nat'l Acad. Sci. 86:10029-10033 (1989).

The antibodies of this invention can be used for affinity chromatography in isolating proteins of the present invention, for screening expression libraries for particular expression products such as normal or abnormal protein, for raising anti-idiotypic antibodies which are useful for detecting or diagnosing various pathological conditions related to the presence of the respective antigens, for detecting expression of the PPO or shikimate dehydrogenase protein or allelic variants when breeding plants, and for down regulating or up regulating the activity of the PPO or shikimate dehydrogenase protein.

Kits

The present invention also includes kits useful for detecting the presence of the PPO and shikimate dehydrogenase nucleic acids and proteins of the present invention. Such kits may include molecules for the detection of the PPO or shikimate dehydrogenase genes and nucleic acids of the present invention such as nucleic acid probes for hybridization or primers for amplification and detection of PPO or shikimate dehydrogenase. Alternatively, such kits may include molecules for the detection of the dehydrogenase proteins of the present invention such as the antibodies and ligands described above. Such kits could be directed to plant breeders for use in breeding non-naturally occurring plants with elevated levels of gallic acid.

The present invention further includes kits useful in generating transgenic plants expressing PPO or the shikimate dehydrogenase protein. Such kits will include the constructs or vectors described above. In addition, the kits may contain additional materials useful for plant transformation as described above under methods.

Gallic Acid Compositions

The present invention is additionally directed to use of gallic acid to inhibit synthesis of aflatoxin. Gallic acid may be applied externally to plants and plant parts to inhibit aflatoxin production. Such gallic acid would be applied at a concentration sufficient to inhibit aflatoxin production. Gallic acid may be applied by itself or in combination with other compounds such as pesticides, herbicides, fungicides and fertilizers. Examples of common pesticides may be found in U.S. Pat. Nos. 6,660,770 and 6,667,326, both of which are hereby incorporated by reference in their entirety. Examples of common herbicides may be found in U.S. Pat. Nos. 6,660,692 and 6,642,176, both of which are incorporated by reference in their entirety. Gallic acid may be applied to plants in crops or to plants or plant parts after harvest, including fruits, vegetables, grains, nuts, berries, and leaves. Such gallic acid applied externally may be washed off such plants or plant part prior to distribution and/or sale or left on since it is found naturally in certain plants. Gallic acid may be applied as a liquid formulation or a solid formulation. The solid formulation would be well suited for application to the soils that the crop plants such as corn, cotton, peanut, and walnut are grown. The liquid formulations would be well suited for application to the crops or the harvested products.

Liquid formulations may be aqueous-based or non-aqueous (i.e., organic solvents), or combinations thereof, and may be employed as foams, gels, suspensions, emulsions, microemulsions or emulsifiable concentrates or the like. The ingredients may include theological agents, surfactants, emulsifiers, dispersants or polymers.

As would be appreciated by a person skilled in the art, the gallic acid concentration will vary widely depending upon the nature of the particular formulation, particularly whether it is a concentrate or to be used directly. Gallic acid will be present in the composition by at least about 1.0% by weight and may be 99 or 100% by weight of the total composition. The gallic acid carrier may be from 0.1% to 99% by weight of the total composition. The dry formulations will have from about 1.0-95% by weight of gallic acid while the liquid formulations will generally be from about 1.0-60% by weight of the solids in the liquid phase. These formulations will be administered at about 50 mg (liquid or dry) to 1 kg or more per hectare.

The formulations can be applied to the crop, the surrounding environment of the crop or the products harvested from the crop, e.g., soil, foliage, fruits, grain, or nuts, by spraying, dusting, sprinkling or the like.

PPO Compositions

Plant material expressing high levels of PPO can be added to silage to improve their protein content. Different concentration can be applied to enhance the protein content. Also, phenolic substrates for the PPO reaction can be blended into silage to enhance the action of PPO.

DESCRIPTION OF PREFERRED EMBODIMENTS

EXAMPLE 1

Gallic Acid Detection in Tulare Pellicle

Chemicals: Gallic acid, gallic acid methyl ester (methyl gallate), ellagic acid, and tannic acid were purchased from Sigma Chemical Co., USA. Rhodanine was purchased from Fluka AG, Germany. All chemicals were of analytical grade.

Extraction of Gallic Acid: Tulare pellicle tissue was harvested at two week intervals over the growing season (June 15, July 1, July 15, August 1, August 15, and September 1), immediately flash frozen in liquid $N_2$, and stored at $-80°$ C. until use. 100 mg of each tissue sample was incubated in boiling 80% EtOH (1 mL for 10 min). After a quick chill on ice, the tissue was pelleted (13,415 g for 20 min at 4° C.) and the supernatant was subsequently transferred to a fresh tube. The liquid was then evaporated off in a vacuum overnight. Citrate buffer (0.5 mL of 0.05M, pH5.0) was added to each tube and used to resuspend the gallic acid.

Detection of Gallic Acid: Levels of gallic acid were measured using the rhodanine assay as described by Sharma, 2000 with minor modifications. Briefly, methanolic rhodanine (0.3 mL of 0.667%) was added to each tube containing the 0.5 mL citrate buffer+sample. The blank contained 0.5 mL citrate buffer+0.001 mL water. The tubes were incubated at 28° C. for 5 min. Potassium hydroxide (0.2 mL of 0.5M) was then added to each tube and incubated at 28° C. for 10 min. Absorbance was read at 520 nm. FIG. 2A shows rhodanine staining of gallic acid and various structurally related compounds. Gallic acid shows the highest signal at 520 nm. FIG. 2A shows the rhodanine staining of gallic acid extracted from the pellicle samples as described above.

EXAMPLE 2

Isolation of the Gallic Acid Anabolic Activity from Tulare

Extraction of Total Soluble Proteins: Tulare pellicle tissue was harvested on August 1, flash frozen in liquid $N_2$, and stored at $-80°$ C. until use. One gram of sample was homogenized in 2 mL of cold extraction buffer (0.05 M Tris, 0.007M citric acid monohydrate, 0.006 M cysteine HCl monohydrate, 0.01 M ascorbic acid, 0.001M polyethylene glycol 8000; pH 8.3). The slurry was centrifuged at 13,000 g for 25 min at 4° C. The supernatant containing the proteins was transferred to a fresh tube.

Fractionation and Detection: The protein sample was loaded onto two consecutive lanes of a native polyacrylamide TBE gel. The gel was run for 2 hrs at 110V in the cold. Following fractionation, the two lanes were separated and stained as follows: 1) proteins from one lane were incubated in the presence of shikimic acid, NADP, MTT, and PMS, as described by Tanksley et al., 2) the second lane was divided into eight sections and stained with rhodanine as described above. FIG. 3A shows the levels of gallic acid produced in the eight gel sections as measured by rhodanine staining. FIG. 3B shows the gel stained with MMT/PMS, indicating the presence of shikimate dehydrogenase activity. In addition, FIG. 3B indicates the gel slices used for FIG. 3A. The shikimate dehydrogenase activity and the gallic acid production co-localize to slice five indicating that shikimate dehydrogenase is the enzyme responsible for gallic acid production in plants.

EXAMPLE 3

Cloning the Shikimate Dehydrogenase Gene from Tulare

Degenerate Primers: The nucleic acid sequences of shikimate dehydrogenase from *Arabidopsis*, tomato, tobacco, rice, and pea were aligned using the program DNAstar. Conserved regions were identified and used to design two sense and two antisense degenerate primers. The sequences of the 5' primers were: 1)

(5'ShDe-1) 5'-CAC(C/T)TACAG(A/G)CC(A/C)A(A/C)(A/T)TGGGAAG(A/G)GG(C/T)CA(A/G)TATG(A/C)(A/T)GGTGATGA-3' (SEQ ID NO: 61) and 2) (5'ShDe-2) 5'-GT(C/T)ATGGG(A/C/T)GA(A/G)A(A/G)(A/G)GGTTT(A/G)ATGTC-3' (SEQ ID NO: 62).

The sequences of the 3' primers were:

1) (3'ShDe-1) 5'-
TAAGCAA(T/G)(A/T)GCCTTGCC(A/T)GC(T/G)CCACCAGCACC-3'
(SEQ ID NO:63)

and 2) (3'ShDe-2) 5'-
GC(A/C)CCCTT(C/T)TC(C/T)TTTGC(A/C)CC(A/G)TAAGCAA(T/G)(A/T)GCCTTGCC-3'.
(SEQ ID NO:64)

Amplification and Cloning: RNA isolated from Tulare pellicle, harvested May 29, was converted into single stranded cDNA using the ProSTAR First-Strand RT-PCR Kit (Invitrogen). The cDNA was then used as the template in amplification reactions with each combination of the 5' and 3' degenerate primers. Amplification was performed on a GeneAmp PCR System 9700 thermal cycle (PE Applied Biosystems). The final volume of each reaction was 50 µL as described by the ProSTAR First-Strand RT-PCR Kit protocol. The cycling parameters were as follows: 30 cycles of 94° C. for 1 min, 52° C. for 1 min, 68° C. for 2 min, followed by a final extension of 68° C. for 10 min. The consensus sequence generated was used to design sense and antisense primers. These primers were used in subsequent RACE reactions (Marathon cDNA Amplification Kit, Clontech Laboratories, Inc.) according to the manufacturers' instructions. The nucleotide sequence of the cDNA for shikimate dehydrogenase from *J. regia* cv. Tulare is shown in FIG. 6. The protein encoded by the cDNA is shown in FIG. 7.

Expression Analysis: The levels of shikimate dehydrogenase activity were measured in Tulare pellicle samples harvested at two week intervals over the growing season from May through September. Equal amounts of total protein from each time point was fractionated on a native polyacrylamide TBE gel and stained for shikimate dehydrogenase activity as described above in Example 2 (FIG. 5A). The relative levels of enzyme activity were compared with the corresponding levels of gallic and ellagic acid in the Tulare pellicle (FIG. 5B).

EXAMPLE 4

Plant Transformation

Expression Construct: Shikimate dehydrogenase had been cloned from *J regia* cv. Tulare. The clone, designated pTP-.ShikimateDehyd was transformed into TOP10 chemically competent *E. coli* cells (Invitrogen, Carlsbad, Calif.). Plasmid DNA was isolated and sequenced.

A full-length transit peptide from the pea ferrodoxin gene, designated pTP12, was kindly provided by Kentaro Inoue (University of California, Davis). PCR based cloning was performed. The sequence of the 5' primer (5'PeaTPXho2) was 5'-gcactcgagatggcttcta-cactctctacc -3' (SEQ ID NO: 65) and the 3' primer (3'PeaTPBam2) was 5'-gcaggatccaaccttgtatgtg-gccattgc -3' (SEQ ID NO: 66). The amplification parameters were as follows: 25 cycles of 94° C. for 1 min, 60° C. for 2 min, 68° C. for 4 min, followed by a final extension of 68° C. for 10 min. 300 ng of pTP12 DNA was used as the template. The PCR product was ligated to the pCR2.1-TOPO vector according to the manufacturers' instructions (TA TOPO Cloning Kit, Invitrogen). Single colonies were screened for growth on LB agar plates supplemented with ampicillin (100 ug/mL). Plasmid DNA designated pTP.PeaTP was isolated and sequenced.

Figure 8:
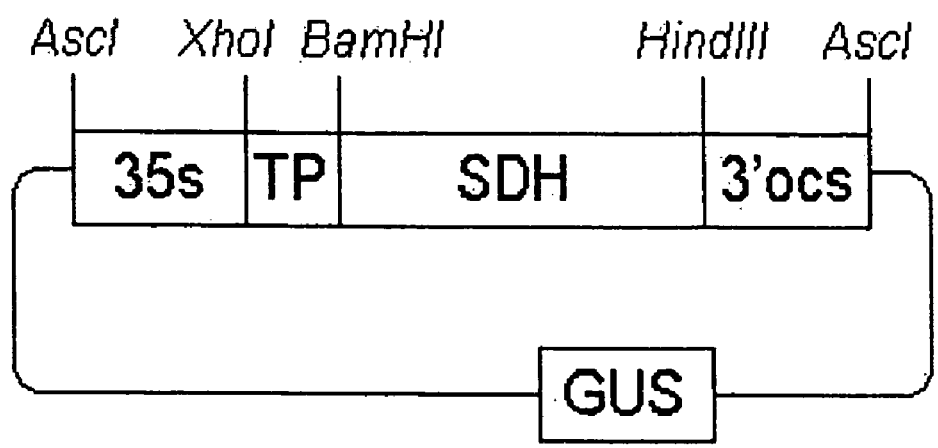
FIG. 8 shows a schematic of Expression Construct pDU04.2601. AscI, XhoI, BamHI and HindIII, restriction enzyme sites used for cloning; 35s, 35s promoter; TP, transit peptide from pea ferrodoxin; SDH, shikimate dehydrogenase from *J. regia* cv. Tulare; 3'ocs, terminator sequence from octopine synthase gene; GUS, β-glucuronidase.

An intermediary cassette, pDEE00.0113, contained a 35S promoter sequence and octopine synthase terminator sequence flanking a multiple cloning site. pDEE00.0113 and pTP.PeaTP were digested with BamHI and XhoI. T4 DNA ligase (Invitrogen) was used to ligate the transit peptide to the vector. The resulting construct, designated pDU04.1706, was digested with BamHI to confirm the orientation of the transit peptide. pDU04.1706 and pTP.ShikimateDehyd were digested with BamHI and HindIII. T4 DNA ligase (Invitrogen) was used to ligate the digestion products to generate pDU04.2327. pDU04.2327 and pDU99.2215, a binary vector for expression in *Agrobacterium*, were digested with AscI T4 DNA ligase (Invitrogen) was used to ligate the digestion products to generate the pDU04.2601 expression construct (FIG. 8).

Transformation: *Agrobacterium* strain EHA105 containing pCH32 and pTiB0542 was used to inoculate 20 mL of 523 liquid media [30 mM sucrose, 14 mM $K_2HPO_4$, 0.6 mM $MgSO_4$, 0.8% casein hydrolysate (w/v), and 0.4% yeast extract (w/v)] (Hamilton 1997; Hood et al. 1993). The cells were grown at room temperature at 225 rpm. 20 µg/mL genticycin and 50 µg/mL kanamycin was added after 2 hrs. When the culture was turbid (~24 hrs), the absorbance at 420 nm was measured and recorded. 25 mL of culture, diluted to $2.5 \times 10^8$ bacteria/mL, was added to 50 mL conical tubes and centrifuged for 10 min at 5000×g. The pellet was resuspended in liquid 003 media supplemented with 100 uM acetosyringone and 1 mM betaine phosphate (pH=5.2) and was used for all subsequent transformations (Dandekar et al. 1989).

Actively growing, non-transformed somatic embryos from *J. regia* cv. Chandler were selected from minimal media plates. Transformation/co-cultivation of the embryos with the *Agrobacterium* was performed as described by Dandekar et. al, 1989. The transformed $E_2$ embryos were screened using the GUS marker from the pDU04.2601 vector (Dandekar et al. 1989). Positive transformants were identified and designated Y2H1, Y2G7, Y2H5, Y2G5, G2D12, G2F8, G2F1, G2G2.

In planta gallic acid production and expression analysis: Total soluble protein was extracted from each of the transformed embryo lines and from a non-transformed somatic embryo line designated CR-1 which had been propagated from *J. regia* cv. Chandler. Protein concentration was measured using the Bradford reagent according to the manufacturers instructions (Bio-Rad Protein Assay, Bio-Rad, Hercules, Calif.). 2 µg protein from each sample was fractionated on a native polyacrylamide TBE gel and stained for shikimate dehydrogenase activity (Diaz et al. 1997; Diaz et al. 2001; Walker 1994).

Figure 9:
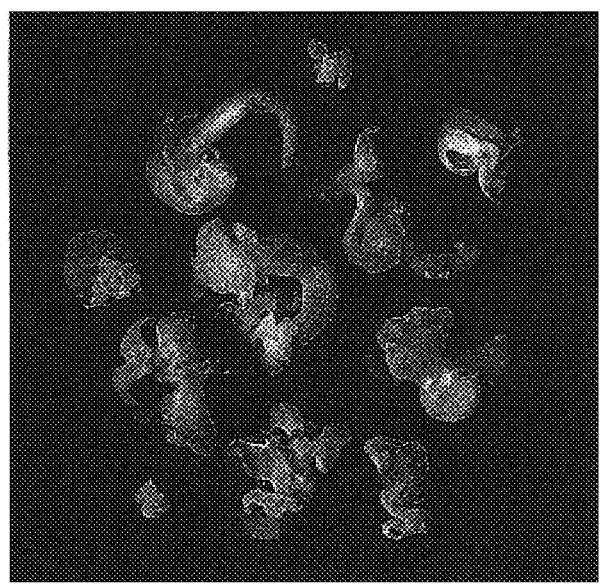
FIG. 9 shows transformed somatic embryos from line Y2H1.

Actively growing, fresh embryo tissue from lines Y2H1, Y2G7, Y2H5, Y2G5, G2D12, G2F8, G2F1, G2G2, and CR-1 was measured and recorded (FIG. 9). The tissue was placed into an eppendorf tube containing 1 mL of buffer (10 mM Tris, pH=8.5). The tissue was macerated (~3 min of grinding/sample) and the tubes were centrifuged to pellet the cellular debris (16,000×g, 5 min). 300 uL of the supernatant was transferred to a fresh tube and measured for gallic acid content using rhodanine (Sharma 2000).

Levels of Shikimate Dehydrogenase Activity:

In planta shikimate dehydrogenase activity and gallic acid production was determined. Levels of shikimate dehydrogenase activity were measured and compared from protein isolated from the transformed lines Y2H1, Y2G7, Y2H5, Y2G5, G2D12, G2F8, G2F1, G2G2 and the non-transformed CR-1 negative control. Lines Y2H1, Y2G7, Y2G5, G2D12, G2F8, G2F1 and G2G2 exhibited increased activity relative to the non-transformed control. Y2H5 exhibited approximately equal levels of activity relative to CR-1 (FIG. 10A).

Non-transformed somatic embryos produced 1.26 µg gallic acid/mg tissue. The lines Y2H1, Y2G5, G2F1, and G2G2 exhibited increased gallic acid production relative to the negative control, accumulating 1.54, 1.51, 1.52 and 1.49 µg gallic acid/mg tissue respectively (FIG. 10B). This conclusively demonstrates that over-expression of shikimate dehydrogenase from *J. regia* cv. Tulare can result in an increased production/accumulation of gallic acid in plant tissues. Position of the heterologous shikimate dehydrognease gene within the genome could potentially account for the variability in gallic acid accumulation within the different transformed lines.

EXAMPLE 5

In Vitro Evaluation of the Rate and Extent of Alfalfa Protein Degradation, Effciency of Protein Utilization and Microbial Protein Synthesis A preliminary in vitro study was conducted to evaluate GA and TA (tannic acid) and to compare this with CT (a source of condensed tannins). The study utilized an in vitro gas production technique that has been established and validated at UC Davis. This system uses canulated cows as a rumen fluid donor. Our preliminary results indicate that the addition of tannins into the in vitro system reduced protein degradation and ammonia-N content by about 50% (see Table 1 below). The reduction in protein degradation and ammonia nitrogen accumulation was dependant on type of tannins and levels used in each of the experiments. In this study, tannic acid (TA) and quebracho tannin (QT) were effective in reducing ammonia-N whereas, GA did not show any affect indicating that it may need to be incorporated into HT to stabilize proteins in the rumen.

TABLE 1

Net ammonium-N (mg) in supernatant after 72 h incubation of 200 mg of two varieties of alfalfa hays in 30 ml buffered rumen fluid with different sources and levels of tannins

| | | | Alfalfa varieties | | | |
|---|---|---|---|---|---|---|
| | Tannins | n | Sutter | % Difference from control | CUF101 | % Difference from control |
| Experiment 1 | Control | 4 | 3.523 (0.524) | — | 3.498 (0.589) | — |
| | GA2 | 4 | 3.540 (0.432) | +0.48 | 3.610 (0.338) | +3.20 |
| | GA4 | 4 | 3.608 (0.564) | −2.41 | 3.670 (0.404) | +4.92 |
| | GA6 | 4 | 3.575 (0.431) | +1.48 | 3.695 (0.305) | +5.63 |
| | QT2 | 4 | 3.363 (0.308) | −4.54 | 3.488 (0.256) | −0.29 |
| | QT4 | 4 | 3.148 (0.368) | −10.54 | 3.353 (0.257) | −4.15 |
| | QT6 | 4 | 2.983 (0.218) | −15.33 | 3.175 (0.270) | −9.23 |
| | TA2 | 4 | 3.168 (0.737) | −10.08 | 3.475 (0.269) | −0.66 |
| | TA4 | 4 | 3.250 (0.424) | −7.75 | 3.358 (0.231) | −4.00 |
| | TA6 | 4 | 2.998 (0.310) | −14.90 | 3.200 (0.308) | −8.52 |
| Experiment 2 | Control | 4 | 3.408 (0.214) | — | 3.393 (0.334) | — |
| | GA5 | 4 | 3.415 (0.191) | +0.21 | 3.450 (0.240) | +1.68 |
| | GA10 | 4 | 3.348 (0.206) | −1.76 | 3.348 (0.254) | −1.33 |
| | GA15 | 4 | 3.298 (0.177) | −3.23 | 3.273 (0.234) | −3.54 |
| | QT5 | 4 | 3.045 (0.204) | −10.65 | 2.943 (0.151) | −13.26 |
| | QT10 | 4 | 2.288 (0.239) | −32.86 | 2.403 (0.065) | −29.03 |
| | QT15 | 4 | 1.620 (0.203) | −52.46 | 1.703 (0.083) | −49.83 |
| | TA5 | 4 | 3.030 (0.167) | −11.09 | 2.830 (0.435) | −16.23 |

TABLE 1-continued

Net ammonium-N (mg) in supernatant after 72 h incubation of 200 mg of two varieties of alfalfa hays in 30 ml buffered rumen fluid with different sources and levels of tannins

| | | Alfalfa varieties | | | |
|---|---|---|---|---|---|
| Tannins | n | Sutter | % Difference from control | CUF101 | % Difference from control |
| TA10 | 4 | 2.543 (0.208) | −25.38 | 2.503 (0.177) | −26.23 |
| TA15 | 4 | 1.888 (0.139) | −44.60 | 1.745 (0.204) | −48.57 |

Concel alfalfa hay withcu: added tannins; Values in paranihesis are standard deviations: GA2, GA4, and GA6 are Gallic acid added at 1.4 and 6% DM: QT2, QT4 and QT6. qnebrachonimic added at 1.4, and 6% DM respectively: A2, TA4, and TA6, umnic acid added at 2. 4, and 6% DM respectively, GA5, GA10, and GA15. Gallic acid added at 5.10 and 15% DM: QA5, QA10, and QA15, quebracho
tannin added at 5.10, and 15% DM respectively: TA5, TA10, and TA15 more tannic acid added at 5.10, and 15% DM respectively In order to determine the role of SKDH in the synthesis of gallic acid and shikimic acid, AroE was cloned from *E. coli* (AroE-3, accession number AY736473) and 3-dehydroquinase dehydratase/shikimate 5-dehydrogenase from *A. thaliana* (SD.38F11-1, accession number AY36474) and *J. regia* (Bam.pB-1, SY738109). To eliminate any affects from the transit peptide on protein expression and enzyme activity, the 5' ends of the complete cDNA sequence were deleted in the plant clones. It is estimated the transit peptide to include the first 76aa of the immature *A. thaliana* protein, based on its reduced sequence homology with SDH from *O. sativa*, *N. tabacum*, and *L. esculentum*. The predicted, average hydrophobicity of SDH residues 1-76 from *A. thaliana* was 0.12, compared with 0.04 for the remainder of the protein. Similiarly, a truncated version of the *J. regia* SKDH clone (Bam.pB-1) that lacked a transit peptide was generated, based on its sequence homology with the predicted transit peptide from *A. thaliana*. The 5' ends of the *J. regia* and *A. thaliana* clones corresponded to approximately the same region of SKDH. Because of the absence of targeting sequences in bacteria, AroE-3 represented the full length SKDH message obtained from GenBank (accession number D90811). Vectors were designed and the JrSKDH (Bam.pB-1, SY738109) was expressed in plants using the CaMV35S regulatory sequences. As can be seen in Table 2, 14 lines were obtained of these 4 expressed GA that was obtained after hydrolysis of the HTs extracted from these plants.

EXAMPLE 6

Creation of Transgenic Plants Expressing Polyphenol Oxidase (PPO)

It was decided to use the JrPPO from walnut that shows a very strong PPO activity in the fruit (hull tissue) from a variety of commercially grown walnut cultivars. All of the examined cultivars were found to display substantial PPO activity. A cDNA library was constructed from RNA isolated from hull tissue of the predominant commercial walnut cultivar in California (Chandler), and this library was screened with a probe derived from the previously published PPO sequence from apple (Boss et al., 1995). A single unique cDNA was identified displaying >50% amino acid sequence identity to PPOs from apple, pear, banana, pineapple, and aspen. The putative PPO gene, denoted JrPPO, possesses clear PPO sequence motifs, including the CuA and CuB copper binding sites and a putative chloroplast transit peptide. The JrPPO open reading frame was subcloned into a plant transformation vector, and Agrobacterium-mediated transformation of alfalfa plants was performed. Shown in Table 2 below is the initial analyses of the transgenic alfalfa plants expressing JrPPO encodes an enzymatically active PPO with both monophenol oxidase and diphenol oxidoreductase activities with at least 4 lines showing activity with a monophenol.

TABLE 2

Preliminary analysis of transgenic alfalfa lines expressing JrSKDH or JrPPO that will be used in this study.

| Transgenic line designation | Gene | Pot# | Total GA pg/mg FW | Crude PPO Activity | Transgenic line designation | Gene | Pot# | Total GA pg/mg FW | Crude PPO Activity |
|---|---|---|---|---|---|---|---|---|---|
| 041328-014 | JrSKDH | 3 | 1336 | − | 041362-013 | JrPPO | 18 | NF | − |
| 041328-008 | JrSKDH | 14 | 5820 | − | 041362-025 | JrPPO | 19 | NF | ++ |
| 041308-013 | JrSKDH | 11 | NF | − | 041362-021 | JrPPO | 20 | NF | − |
| 041328-011 | JrSKDH | 8 | NF | − | 041362-033 | JrPPO | 21 | NF | − |
| 041328-004 | JrSKDH | 5 | NF | − | 041362-026 | JrPPO | 22 | NF | − |
| 041328-012 | JrSKDH | 1 | NF | − | 041362-047 | JrPPO | 23 | NF | − |
| 041328-003 | JrSKDH | 16 | NF | − | 041362-046 | JrPPO | 24 | NF | − |
| 041308-005 | JrSKDH | 12 | NF | − | 041362-064 | JrPPO | 25 | NF | ++++ |
| 041307-005 | JrSKDH | 7 | NF | − | 041362-079 | JrPPO | 26 | NF | − |
| 041307-009 | JrSKDH | 6 | 2984 | − | 041362-052 | JrPPO | 27 | NF | − |
| 041308-009 | JrSKDH | 10 | 1852 | − | 041362-008 | JrPPO | 28 | NF | − |
| 041328-001 | JrSKDH | 13 | NF | − | 041362-048 | JrPPO | 29 | NF | − |

TABLE 2-continued

Preliminary analysis of transgenic alfalfa lines expressing JrSKDH or JrPPO that will be used in this study.

| Transgenic line designation | Gene | Pot# | Total GA pg/mg FW | Crude PPO Activity | Transgenic line designation | Gene | Pot# | Total GA pg/mg FW | Crude PPO Activity |
|---|---|---|---|---|---|---|---|---|---|
| 041328-007 | JrSKDH | 9 | NF | – | 041362-056 | JrPPO | 30 | NF | – |
| 041308-002 | JrSKDH | 2 | NF | – | 041362-055 | JrPPO | 31 | NF | – |
| 041308-003 | NT | 34 | NF | – | 041362-061 | JrPPO | 32 | NF | + |
| Control 1 | NT | 35 | NF | – | 041362-043 | JrPPO | 33 | NF | – |
| Control 2 | NT | 36 | NF | – | | | | | |

JrSKDH-Walnut shikimate dehyrogenase that makes Gallic Acid the precursor for HT synthesis;
NT-Not Transformed;
JrPPO-Walnut polyphenol oxidase

REFERENCES

The following references are hereby incorporated by reference in their entirety.

Aerts, R. J. et al. (1999) Ag. Eco. Env. 75:1-12.
Aerts, R. J. et al. (1999a) J. Sci. Food Ag. 79:79-85.
Aerts, R. J., Barry, T. N., McNabb, W. C. (1999a) Polyphenols and agriculture: beneficial effects of proanthocyanidins in forages. Agricultre, Ecosystems and Environment 75, 1-12
Aerts, R. J., McNabb, W. C., Molan, A., Brand, A., Barry, T. N., Peters, J. S. (1999b) Condensed tannins from *Lotus corniculatus* and *Lotus pedunculatus* exert different effects on the in vitro rumen degradation of ribulose-1,5-bisphosphate carboxylase/oxygenase (Rubisco) protein. Journal of Science and Food Agriculture 79, 79-85.
Altschul, S. F. et al. (1990) J. Mol. Bio. 215:403-410.
Altschul, S. F. et al. (1994) Nat. Genet. 6(2):119-29.
Amakura, Y., Umino, Y., Tsuji, S., Ito, H., Hatano, T., Yoshida, T., Tonogai, Y. 2002. Constituents and their antioxidative effects in eucalyptus leaf extracts used as a natural food additive. Food Chemistry 77, 47-56.
Barry, T. N. and Manley, T. R. (1986) Interrelationships between the concentrations of total condensed tannin, free condensed tannin and lignin in *Lotus* sp. and their possible consequences in ruminant nutritrion. Journal of Science and Food Agriculture 37, 248-254
Barry, T. N. and McNabb, W. C. (1999) Brit. J. Nut. 81:263-272.
Barry, T. N. and McNabb, W. C. (1999) The implications of condensed tannins on the nutritive value of temperate forages fed to ruminants. British Journal of Nutrition 81, 263-272.
Benach 3, Lee I, Edstrom W, Kuzin A P, Chiang Y, Acton T B, Montelione G T, Hunt J F (2003). The 2.3-Å crystal structure of the shikimate 5-dehydrogenase orthologue YdiB from *Escherichia coli* suggests a novel catalytic environment for an NAD-dependent dehydrogenase. J Biol Chem. 278:19176-82.
Bhat, T. K. et al. (1998) Microbial degradation of tannins—A current perspective. Biodegradation 9 (5), 343-357.
Bonner C A, Jensen R A (1994). Cloning of cDNA encoding the bifunctional dehydroquinase shikimate dehydrogenase of aromatic-amino-acid biosynthesis in *Nicotiana tabacum*. Biochem J. 302:11-14.
Boss P K, Gardner R C, Janssen B-J, and Ross G S. 1995. An apple polyphenol oxidase cDNA is upregulated in wounded tissues. Plant Mol. Biol. 27: 429-433.
Broderick, G. 2002 Maximizing utilization of alfalfa protein; the example of the lactating dairy cow.
Broderick, G., J. H. Yang, and R. G. Koegel. 1993. Effect of steam heating alfalfa hay on utilization by dairy cows. J. Dairy Sci. 76:165-174.
Burkart, M. R., and D. E. James. 1999. Agricultural nitrogen contributions to hypoxia in the Gulf of Mexico. J. Environ. Qual. 28:850-859.
Campbell, B. and Molyneux, R. J. (2003) Journal of Toxicology-Toxin Reviews 22(2-3): 225-266.
Chariton, A. J., Baxter, N. J., Lilley, T. H., Haslam, E., McDonald, C. J. and Williamson, M. P. (1996) Tannin interactions with a full-length human salivary proline-rich protein display a stronger affinity than with single proline-rich repeats. FEBS Letters 382 (3), 289-292.
Chaudhuri S, Duncan K, Graham L D, Coggins J R. (1991). Identification of the active-site lysine residues of two biosynthetic 3-dehydroquinases. Biochem J. 275:1-6.
Chung, K.-T. et al. (1998) Mechanism of inhibition of tannic acid and related compounds on the growth of intestinal bacteria. Food and Chemical Toxicology (36), 1053-1060.
Clauss, M. et al. (2003) Captive roe deer (*Capreolus capreolus*) select for low amounts of tannic acid but not quebracho: Fluctuation of preferences and potential benefits. Comparative Biochemistry & Physiology. Part B, Biochemistry & Molecular Biology 136B (2), 369-382.
Corpet, F. (1988) Nucleic Acids Res. 16:10881-10890.
Dandekar, A. M. et al. (1989) *Agrobacterium*-mediated transformation of somatic embryos as a method for the production of transgenic plants. Journal of Tissue Culture Methods 12: 145-150.
Deka R K, Kleanthous C, and Coggins J R (1992). Identification of the essential histidine residue at the active site of *Escherichia coli* dehydroquinase. J. Biol. Chem., 267: 22237-42
Desgagnes, R. et al. (1995) Pl. Cell Tis. Org. Cul. 42:129-140.
Diaz, J. et al. (1997) Changes in shikimate dehydrogenase and the end products of the shikimate pathway, chlorogenic acid and lignins, during the early development of seedlings of *Capsicum annuum*. New Phytologist 136: 183-188.
Diaz, J. et al. (2001) Induction of shikimate dehydrogenase and peroxidase in pepper (*Capsicum annuum* L.) seedlings in response to copper stress and its relation to lignification. Plant Science (Shannon) 161: 179-188.
Douglas, J. H. et al. (1990) Nutrient composition and metabolizable energy values of selected grain sorghum varieties and yellow corn. Poultry Science 69 (7), 1147-1155.
Eaton, D. L. and Gallagher, E. P. (1994) Annu. Rev. Pharmacol. Toxicol. 1994:135-172.

Elkin, R. G. et al. (1990) Comparative effects of dietary tannins in ducks, chicks and rats. Poultry Science 69 (10), 1685-1693.

Elrod, C. C. and Butler, W. R. 1993. Reduction of fertility and alteration of uterine pH in heifers fed excess ruminally degradable protein. J. Anim Sci. 71: 694-701

Eyles, A. et al. (2004) Role of *Eucalyptus globulus* wound wood extractives: evidence of superoxide dismutase-like activity. Forest Pathology 34 (4), 225-232.

Fahn A. in Plant Anatomy, 4$^{th}$ Edition. Pergamon Press Ltd., Oxford, pp 11-49.

Feldman, K. S. et al. (1999) Binding affinities of gallotannin analogs with bovine serum albumin: ramifications for polyphenol-protein molecular recognition. Phytochemistry 51, 867-872.

Frohlich, B. et al. (2002) Gallotannin biosynthesis: two new galloyltransferases from *Rhus typhina* leaves preferentially acylating hexa- and heptagalloylglucoses. Planta 216 (1), 168-172.

Gerdemann C, Eicken C, Magrini A, Meyer H E, Rompel A, Spener F, Krebs B. (2001). Biochimica et Biophysica Acta 1548: 94-105.

Getachew, G., DePeters, E. J., Robinson, P. H., Taylor, S. J., 2001. In vitro rumen fermentation and gas production: influence of yellow grease, tallow, corn oil and their potassium soaps. Anim. Feed Sci. Technol. 93, 1-15.

Getachew, G., Makkar, H. P. S. and Becker, K. 2000. Effect of polyethylene glycol on in vitro degradability of nitrogen and microbial protein synthesis from tannin-rich browses and herbaceous legumes. British Journal of Nutrition 84: 73-83.

Getachew, G., Robinson, P. H., DePeters, E. J., Taylor, S. J., Gisi, D. D., Higginbotham, G. E. and Riordan, T. J. (2005) Methane production from commercial dairy rations estimated using an in vitro gas technique. Animal Feed Science and Technology, 123-124, 391-402

Gourama, H. and Bullerman, L. B. (1995) J. Food Protect. 58(12):1395-1404.

Goyal, S. S., D. W. Rains and R. C. Huffaker. 1988. Determination of ammonium ion by fluorometry or spectrophotometry after on line derivatization with o-phthalaldehyde. Analytical Chemistry 60:175 179.

Gross, G. G. (2000) Biosynthesis and immunolocalization of gallotannins and ellagitannins. Abstracts of Papers American Chemical Society 219 (1-2), CELL 141.

Grundhoefer, P. et al. (2001) Biosynthesis and subcellular distribution of hydrolyzable tannins. Phytochemistry (Oxford) 57 (6), 915-927.

Hagerman, A. E. and Butler, L. G. (1991) Tannins and Lignins. In Herbivores: Their Interactions with Secondary Metabolites, 2nd Edition (Vol. 1), Academic Press, Inc.

Hagerman, A. E. et al. (1998) High molecualr weight plant polyphenolics (tannins) as biological antioxidants. Journal of Agricultural and Food Chemistry 46, 1887-1892.

Hamilton, C. M. (1997) A binary-BAC system for plant transformation with high-molecular-weight DNA. Gene 200: 107-116.

Haslam E., C. Y. (1994) Plant polyphenols (vegetable tannins*): gallic acid metabolism. Natural Product Reports 11, 41-66

Haslam, E. (1998a) Gallic acid metabolism. In Practical Polyphenolics: From Structure to Molecular Recognition and Physiological Action, pp. 51-83, Cambridge University Press Haslam, E. (1998b) Che Faro Senza Poliferoli. In Polyphenols 2, Chemistry, Biology, Pharmacology, Ecology (Vol. 66) (Gross, G. G. et al., eds.), pp. 15-40, Kluwer Academic/Plenum Publishers.

Hernandez-Romero D, Sanchez-Amat A, Solano F. (2006). A tyrosinase with an abnormally high tyrosine hydroxylase/dopa oxidase ratio. The FEBS Journal 273: 257-270.

Higgins, D. G. and Sharp, P. M. (1988) Gene 73(1):237-44.

Higgins, D. G. and Sharp, P. M. (1989) Comput Appl Biosci. 5(2):151-3.

Hood, E. E. et al. (1993) New Agrobacterium helper plasmids for gene transfer to plants. Transgenic Research 2: 208-218.

Huang X. et al. (1992) Comput. Appl. Biosci. 8(2):155-65.

Hussain, S. et al. (1994) Oncogene 9(8):2277-2281.

Hvelplund, T., and J. Madsen. 1996. Protein utilization in ruminants. Pages 83-93 in Proc. 7th Intl. Symp. Prot. Met. Nutr. Vale deSantarem, Portugal. EAAP, The Netherlands. National Institue of Animal Science, Foulum, Denmark.

Irwin, J. A. G., Lioyd, D. L., and Lowe, K. F. (2001). Lucerne biology and genetic improvement—an analysis of past activities and future goals in Australia. Australian Journal of Agricultural Research 52, 69-712.

Jacob, J. P. et al. (1996) The effect of substituting Kenyan Serena sorghum for maize in broiler starter diets with different dietary crude protein and methionine levels. Animal Feed Science & Technology 61, 27-39.

Jones, W. T. et al. (1973) Bloat in cattle, XXXIX. Detection of protein precipitants (flavolans) in legumes. New Zealand Journal of Agricultural Research 16, 441-446.

Jones, W. T. et al. (1973) New Zea. J. Ag. Res. 16: 441-446.

Julier, B., C. Huyghe, J. C. Emile, P. Morris, G. Allison, and M. Robbins. 2002 Variation in protein degradability in three forage legume species.

Julier, B., F. Guines, J. Emile, and C. Huyghe. 2003. Variation in protein degradability in dried forage legumes. Anim. Res. 52 (2003) 401-412 DOI: 10.1051/animres:2003029

Kim, Y.-J., and Umaya, H. (2005) Tyrosinase inhibitors from natural and synthetic sources: structure, inhibition mechanism and perspective for the future. CMLS, Cell. Mol. Life Sci. 62:1707-1723.

Kathuria, P. C. et al. (1993) Indian Veterinary Journal 70(12): 1093-1096.

Kawamoto, H. and Nakatsubo, F. (1997a) Solubility of protein complexed with galloylglucoses. Phytochemistry 46 (3), 485-488.

Kawamoto, H. and Nakatsubo, F. (1997b) Effects of environmental factors on two-stage tannin-protein co-precipitation. Phytochemistry 46 (3), 479-483.

Kawamoto, H. et al. (1995) Quantitative determination of tannin and protein in the precipitates by highperformance liquid chromatography. Phytochemistry 40 (5), 1503-1505

Kawamoto, H. et al. (1996) Stoichiometric studies of tannin-protein co-precipitation. Phytochemistry (Oxford) 41 (5), 1427-1431.

Kawamoto, H. et al. (1997) Binding nature and denaturation of protein during interaction with galloylglucose. Phytochemistry 46 (3), 473-478.

Khanbabaee, K. and van Ree, T. (2001) Tannins: Classification and definition. Natural Product Reports 18 (6), 641-649.

Klabunde T, Eicken C, Sacchettini J C, and Krebs B. 1998. Crystal structure of a plant catechol oxidase containing a dicopper center. Nat. Struct. Biol. 5: 1084-1090.

Kohn, R. A., Z. Dou, J. D. Ferguson, and R. C. Boston. 1997. A sensitivity analysis of nitrogen losses from dairy farms. J. Environ. Manage. 50:417-428.

Lee, K. W. (2002) Mole. Cells 14:388-397.

Leelavanthi, S. et al. (2004) Pl. Cell Rep. 22:465-470.

Lobley, G. E. 2002. Protein turnover—What does it mean for animal production? Pages 1-15 in Proc. Symp. Amino Acids: Meat, Milk and More. H. Lapierre and D. R. Ouellet, ed. Quebec, Canada. Can. Soc. Anim. Sci.

Madacsi, J. P. et al. (1988) Treatment of low-tannin sorghum grain for broiler feed. Animal Feed Science & Technology 20 (1), 69-78.

Mahoney, N. and Molyneux, R. J. (2004) Phytochemical inhibition of Aflatoxigenicity in *Aspergillus flavus* by constituents of walnut (*Juglans regia*). J. Agric. Food Chem. 52, 1882-1889.

Makkar, H. P. S. and K. Becker. 1999. Purine quantification in digesta from ruminants by spectrometric and HPLC methods. British Journal of Nutrition. 81: 107-112.

Makkar, H. P. S. et al. (1995) In vitro effects of and interactions between tannins and saponins and fate of tannins in the rumen. Journal of Science and Food Agriculture 69, 481-493.

Mansur E. et al. in *Agrobacterium* Protocols. Humana Press Inc., Totowa, N.J., pp 87-100.

Martin, N., R. Hatfield and D. Mertens. 2005. Reinventing Alfalfa—Dairy Cattle and Novel Uses. IN 35th California Alfalfa Symposium Proceedings. 12-15th December, Visalia, Calif., 2005. University of California Cooperative Extension McSweeney, C. S. et al. (2001) An. Feed Sci. Tech. 91: 83-93.

McSweeney, C. S. et al. (2001) Microbial interactions with tannins: Nutritional consequences for ruminants. Animal Feed Science & Technology 91 (1-2), 83-93.

Michel G, Roszak A W, Sauve V, Maclean J, Matte A, Coggins J R, Cygler M, Lapthorn A J (2003). Structures of shikimate dehydrogenase AroE and its Paralog YdiB. A common structural framework for different activities. J Biol Chem. 278:19463-72.

Moreno, O. J. and Kang, M. S. (1999) Plant Breeding 118(1): 1-16.

Murata M, Nishimura M, Murai N, Haruta M, Homma S, and Itoh Y. 2001. A transgenic apple callus showing reduced polyphenol oxidase activity and lower browning potential. 65: 383-388. Niemetz R, N. J., Gross G. (1998) Biosynthesis and biodegradation of complex gallotannin: In Plant Polyphenols 2.

Nakrieko K. A. et al. (2004) Eur. J. Biochem. 271:509-516.

Needleman, S. B. and Wunsch, C. D. (1970) J. Mol. Biol. 48:443-453.

Nga, L. T. et al. (1999) Pl. J. 20:519-527.

Nichols, C. E., Lockyer, M. Hawkins, A. R. and Stammers, D. K. (2004). Crystal Structures of *Staphylococcus aureus* Type I Dehydroquinase from Enzyme Turnover Experiments. Proteins: Structure, Function, and Bioinformatics. 56:625-628.

O'Donovan, L. and Brooker, J. D. (2001) Effect of hydrolysable and condensed tannins on growth, morphology and metabolism of *Streptococcus galloylticus* (*S. caprinus*) and *Streptococcus bovis*. Microbiology 147, 1025-1033.

Okamura, H. et al. (1993) Antioxidant activity of tannins and flavonoids in *Eucalyputs Rostrata*. Phytochemistry 33 (3), 557-561

Ornatowski, W. et al. (2004) In Vit. Cell. Dev. Bio. Pl. 40:260-265.

Parr, A. J. and Bolwell, G. P. (2000) Phenols in the plant and in man. The potential for possible nutritional enhancement of the diet by modifying the phenols content or profile. Journal of the Science of Food and Agriculture 80 (7), 985-1012.

Pearson, W. R., Lipman, D. J., (1988) Proc Natl Acad Sci U.S.A. 85:2444-8.

Perez-Maldonado, R. A. et al. (1995) Factors affecting in vitro formation of tannin-protein complexes. Journal of Science and Food Agriculture 69, 291-298.

Perez-Maldonado, R. A. et al. (1995) J. Sci. Food Ag. 69:291-298.

Rasco-Gaunt, S. et al. (2003) Plant Cell Rep. 21:569-576.

Riday & Brummer, (2002)

Rotz, C. A., L. D. Satter, D. R. Mertens, and R. E. Muck. 1999. Feeding strategy, nitrogen cycling, and profitability of dairy farms. J. Dairy Sci. 82:2841-2855.

Sharma, R. et al. (1999) Physio. Planta. 105(4):739-745.

Sharma, S. B. et al. (2000) A spectrophotometric method for assay of tannase using rhodanine. Analytical Biochemistry 279: 85-89.

Sliwinski, B. J. et al. (2002) Efficacy of plant extracts rich in secondary constituents to modify rumen fermentation. Animal Feed Science & Technology 101 (1-4), 101-114.

Smela, M. E. et al. (2001) Carcinogenesis 22(4):535-545.

Smith, R. L. et al. (1989) Use of pearl millet sorghum and triticale grain in broiler diets. Journal of Production Agriculture 2 (1), 78-82.

Smith, T. F. and Waterman, M. S. (1981) J. Mol. Biol. 147: 195-197.

Steffens J C, Harel E, and Hunt M D. 1994. Polyphenol oxidase. In: Ellis BE (Ed.) Genetic Engineering of Plant Secondary Metabolism. Plenum Press, New York. pp. 275-312.

Stemmer, W. P. (1994a) Nature 370:389-91.

Stemmer, W. P. (1994b) Proc Natl Acad Sci USA. 91:10747-51.

Tanksley, S. D. and Orton T. J. (1983) Isozymes in Plant Genet. Breed. Elsevier Science Publishers, B. V. Amsterdam p492.

Terada, R. (2004) Pl. Cell Rep. 22:653-659.

Tiemersma E. W. et al. (2001) Cancer Epidemio. Biomark. and Prev. 10(7):785-791.

Trail, F. et al (1995) Microbiology 141(4):755-765.

Van Gelder C W G, Flurkey W H, and Wichers H J. 1997. Sequence and structural features of plant and fungal tyrosinases. Phytochem. 45: 1309-1323.

van Horn, H. H., G. L. Newton, R. A. Norstedt, G. Kidder, E. C. French, D. A. Graetz, and C. F. Chambliss. 1996. Dairy manure management: strategies for recycling nutrients to recover fertilizer value and avoid environmental pollution. Circ. 1016 (revised). Florida Coop. Ext. Serv., Gainesville, Fla.

Viquez, O. M. (2003) Mol. Immunol. 40(9):565-571.

Waghorn, G. C. (1990) Effect of condensed tannin on protein digestion and nutritive value of fresh herbage. Proceedings of the Australian Society of Animal Productivity 18, 412-415.

Walker J R L and Ferrar P H. 1998. Diphenol oxidases, enzyme-catalyzed browning and plant disease resistance. Biotech. Gen. Eng. Rev. 15: 457-498.

Walker, J. M. (1994) Nondenaturing Polyacrylamide Gel Electrophoresis of Proteins. In: Walker, J. M. in Basic Protein and Peptide Protocols. Humana Press Inc., Totowa, N.J., pp 17-22.

Wang, C. et al. (2000) Toxicolog. Sci. 56(1) 26-36.

Woloshuck, C. P. and Prieto, R. (1998) FEMS Lett. 160(2): 169-176.

Yan-Yun, L. et al. (2000) Biochem. J. 351:377-384.

Ye S, Von Delft F, Brooun A, Knuth M W, Swanson R V, and McRee D E (2003). The crystal structure of shikimate dehydrogenase (AroE) reveals a unique NADPH binding mode. J. Bacteriol. 185:4144-51.

Yilmaz, Y. and Toledo, R. T. (2004) Major flavonoids in grape seeds and skins: antioxidant capacity of catechin, epicatechin, and gallic acid. Journal of Agricultural and Food Chemistry 52, 255-260

Zhang, X. P. and Glaser E. (2002) Tr. Pl. Sci. 7:14-21.

Zhao, J. et. al. (2002) Planta 216:180-186.

Zhu, Y. Q. et al. (2003) Plant. Phys. 133:580-588.

Cho M-H, Moinuddin S G A, Helms G L, Hishiyama S, Eichinger D, Davin L B, and Lewis N G. 2003. (+)-Larreatricin hydroxylase, an enantio-specific polyphenol oxidase from the creosote bush (*Larrea tridentata*). Proc. Natl. Acad. Sci. USA. 100: 10641-10646.

Constabel C P and Ryan C A. 1998. A survey of wound- and methyl jasmonate-induced leaf polyphenol oxidase in crop plants. Phytochem. 47: 507-511.

Constabel C P, Yip L, Patton J J, and Christopher M E. 2000. Polyphenol oxidase from hybrid poplar. Cloning and expression in response to wounding and herbivory. 124: 285-295.

Dry I B and Robinson S P. 1994. Molecular cloning and characterization of grape berry polyphenol oxidase. Plant Mol. Biol. 26: 495-502.

Felton G W, Donato K K, Broadway R M, and Duffey S S. 1992. Impact of oxidized plant phenolics on the nutritional quality of dietary protein to a noctuid herbivore, *Spodoptera exigua*. J. Insect Physiol. 38: 277-285.

Gandía-Herrero F, Escribano J, and García-Carmona F. 2005. Betaxanthins as substrates for tyrosinase. An approach to the roles of tyrosinase in the biosynthetic pathway of betalins. Plant Physiol. 138: 421-432.

Gooding P S, Bird C, and Robinson S P. 2001. Molecular cloning and characterization of banana fruit polyphenol oxidase. Planta. 213: 748-757.

Joy R W, Sugiyama M, Fukuda H, and Komamine A. 1995. Cloning and characterization of polyphenol oxidase cDNAs of *Phytolacca americana*. Plant Physiol. 107: 1083-1089.

Klabunde T, Eicken C, Sacchettini J C, and Krebs B. 1998. Crystal structure of a plant catechol oxidase containing a dicopper center. Nat. Struct. Biol. 5: 1084-1090.

Kosuge T. 1969. The role of phenolics in host response to infection. Ann. Rev. Phytopathol. 7: 195-222.

Li L, and Steffens J C. 2002. Overexpression of polyphenol oxidase in transgenic tomato plants results in enhanced bacterial disease resistance. Planta. 215: 239-247.

Mayer A M and Harel E. 1979. Polyphenol oxidases in plants. Phytochem. 18: 193-214.

Murata M, Nishimura M, Murai N, Haruta M, Homma S, and Itoh Y. 2001. A transgenic apple callus showing reduced polyphenol oxidase activity and lower browning potential. 65: 383-388.

Nakayama T, Sato T, Fukui Y, Yonekura-Sakakibara K, Hayashi H, Tanaka Y, Kusumi T, and Nishino T. 2001. Specificity analysis and mechanism of aurone synthesis catalyzed by aureusidin synthase, a polyphenol oxidase homolog responsible for flower coloration. FEBS Lett. 499: 107-111.

Steffens J C, Harel E, and Hunt M D. 1994. Polyphenol oxidase. In: Ellis B E (Ed.) Genetic Engineering of Plant Secondary Metabolism. Plenum Press, New York. pp. 275-312.

Sullivan M L, Hatfield R D, Thoma S L, and Samac D A. 2004. Cloning and characterization of red clover polyphenol oxidase cDNAs and expression of active protein in *Escherichia coli* and transgenic alfalfa. Plant Physiol. 136: 3234-3244.

Thipyapong P and Steffens J C. 1997. Tomato polyphenol oxidase. Plant Physiol. 115: 409-418.

Thipyapong P, Melkonian J, Wolfe D W, and Steffens J C. 2004. Suppression of polyphenol oxidases increases stress tolerance in tomato. Plant Sci. 167: 693-703.

Van Gelder C W G, Flurkey W H, and Wichers H J. 1997. Sequence and structural features of plant and fungal tyrosinases. Phytochem. 45: 1309-1323.

Vaughn K C, Lax A R, and Duke S O. 1988. Polyphenol oxidase: the chloroplast oxidase with no established function. Physiol. Plant. 72: 659-665.

Walker J R L and Ferrar P H. 1998. Diphenol oxidases, enzyme-catalyzed browning and plant disease resistance. Biotech. Gen. Eng. Rev. 15: 457-498.

Wang J and Constabel P. 2004. Polyphenol oxidase overexpression in transgenic Populus enhances resistance to herbivory by forest tent caterpillar (*Malacosoma disstria*). 220: 87-96.

We claim:

1. A transgenic plant comprising an elevated level of gallic acid, wherein the transgenic plant is produced by introducing into a plant one or more transgenes encoding a shikimate dehydrogenase protein, wherein the one or more transgenes comprise a nucleic acid selected from the group consisting of:
   a) a nucleic acid having at least about 95% sequence identity to SEQ ID NO: 1or its complement, and
   b) a nucleic acid encoding a protein comprising an amino acid sequence having at least about 95% sequence identity to SEQ ID NO: 2.

2. The transgenic plant of claim 1 wherein the one or more transgenes are operably linked to a promoter functional in plants.

3. The transgenic plant of claim 2 wherein the promoter directs tissue specific expression of the one or more transgenes to a tissue selected from the group consisting of testa, seed hairs, hull epidermis, hull cortex, shell, pellicle, husk, kernel, embryo, pod, seed, and seed coat.

4. A method of producing a transgenic plant with elevated levels of gallic acid, the method comprising: transforming a plant with a recombinant nucleic acid encoding a shikimate dehydrogenase protein operably linked to a transit peptide to produce a transgenic plant with elevated levels of gallic acid compared to the gallic acid levels of a comparable non-transgenic plant, wherein the recombinant nucleic acid is selected from the group consisting of:
   a) a nucleic acid having at least about 95% sequence identity to SEQ ID NO: 1or its complement, and
   b) a nucleic acid encoding a protein comprising an amino acid sequence having at least about 95% sequence identity to SEQ ID NO: 2.

5. The method of claim 4 wherein the recombinant nucleic acid is operably linked to a promoter functional in plants.

6. The method of claim 5, wherein the promoter directs tissue specific expression of the recombinant nucleic acid to a tissue selected from the group consisting of testa, seed hairs, hull epidermis, hull cortex, shell, pellicle, husk, kernel, embryo, pod, seed, and seed coat.

7. The method of claim 4, wherein the recombinant nucleic acid comprises a nucleotide sequence having at least about 95% sequence identity to SEQ ID NO: 1 or its complement.

8. The method of claim 4, wherein the recombinant nucleic acid comprises the nucleic acid sequence of SEQ ID NO: 1 or its complement.

9. The method of claim 4, wherein the recombinant nucleic acid encodes a polypeptide comprising an amino acid sequence having at least about 95% sequence identity to the amino acid sequence of SEQ ID NO: 2.

10. An isolated nucleic acid, wherein the nucleotide sequence consists of SEQ ID NO: 1.

11. An isolated nucleic acid, wherein the nucleic acid encodes a polypeptide consisting of SEQ ID NO: 2.

12. The transgenic plant of claim 1, wherein the plant is selected from the group consisting of walnut, cotton, peanut, rice, alfalfa, soybean, wheat and corn.

13. The transgenic plant of claim 1, wherein the elevated levels of gallic acid is localized to the pellicle of the plant seed or nut.

14. The transgenic plant of claim 1, wherein the elevated levels of gallic acid is localized to a tissue of said plant, said tissue selected from the group consisting of testa, seed hairs, hull epidermis, hull cortex, shell, pellicle, husk, kernel, embryo, pod, peg, seed, and seed coat.

15. A host cell transformed with nucleic acid of claim 11.

16. A vector comprising the isolated nucleic acid of claim 11.

17. A host cell comprising the vector of claim 16.

18. An offspring of the transgenic plant of claim 1, wherein the offspring comprises the one or more transgenes.

* * * * *